United States Patent
Levi et al.

(10) Patent No.: US 8,463,404 B2
(45) Date of Patent: Jun. 11, 2013

(54) ELECTRODE ASSEMBLIES, TOOLS, AND METHODS FOR GASTRIC WALL IMPLANTATION

(75) Inventors: Tamir Levi, Moshav Ein Haemek (IL); Paul Spehr, Medford, NJ (US); Offer Glasberg, Zichron Ya'akov (IL); Tami Harel, Haifa (IL); Lena Milman, Haifa (IL); Benny Rousso, Rishon LeZion (IL); Elazar Sonnenschein, Beer Sheva (IL); Yuval Elovici, Moshav Shetolim (IL); Minelu Sonnenschein, Meitar (IL); Amir Govrin, Tel Aviv (IL)

(73) Assignee: Metacure Limited, Hamilton (BM)

( * ) Notice: Subject to any disclaimer, the term of this patent is extended or adjusted under 35 U.S.C. 154(b) by 698 days.

(21) Appl. No.: 12/160,616

(22) PCT Filed: Jan. 14, 2007

(86) PCT No.: PCT/IL2007/000052
§ 371 (c)(1),
(2), (4) Date: Sep. 1, 2010

(87) PCT Pub. No.: WO2007/080595
PCT Pub. Date: Jul. 19, 2007

(65) Prior Publication Data
US 2010/0324644 A1    Dec. 23, 2010

Related U.S. Application Data

(63) Continuation-in-part of application No. PCT/US2006/010911, filed on Mar. 24, 2006, and a continuation-in-part of application No. PCT/IL2006/000644, filed on Jun. 4, 2006, and a continuation-in-part of application No. PCT/US2006/010911, filed on Mar. 24, 2006.

(60) Provisional application No. 60/758,937, filed on Jan. 12, 2006, provisional application No. 60/665,320, filed on Mar. 24, 2005, provisional application No. 60/687,099, filed on Jun. 2, 2005.

(51) Int. Cl.
*A61N 1/05* (2006.01)

(52) U.S. Cl.
USPC .............................. 607/133; 607/40; 128/898

(58) Field of Classification Search
USPC ............................ 607/133, 40, 116; 128/898
See application file for complete search history.

(56) References Cited

U.S. PATENT DOCUMENTS 3,411,507 A   11/1968   Wingrove
3,516,412 A   6/1970   Ackerman
(Continued)

FOREIGN PATENT DOCUMENTS

EP   0057048   8/1982
EP   0129483   12/1984
(Continued)

OTHER PUBLICATIONS

International Search Report and the Written Opinion Dated Sep. 2, 2011 From the International Searching Authority Re. Application No. PCT/IL 11/00116.

(Continued)

*Primary Examiner* — Christopher D Koharski
*Assistant Examiner* — Michael Carey
(74) *Attorney, Agent, or Firm* — William H. Dippert; Eckert Seamans Cherin & Mellott, LLC

(57) ABSTRACT

Apparatus (450) is provided including an electrode (460) and an implantation tool (458) configured to be passed into an abdominal cavity of a patient, and to insert the electrode into a gastric wall of the patient, generally in parallel to the gastric wall. Other embodiments are also described.

28 Claims, 35 Drawing Sheets

U.S. PATENT DOCUMENTS

| | | |
|---|---|---|
| 3,737,579 A | 6/1973 | Bolduc |
| 4,000,745 A | 1/1977 | Goldberg et al. |
| 4,010,758 A | 3/1977 | Rockland et al. |
| 4,133,315 A | 1/1979 | Berman et al. |
| 4,177,818 A | 12/1979 | De Pedro |
| 4,235,246 A | 11/1980 | Weiss |
| 4,280,503 A | 7/1981 | Ackerman |
| 4,313,448 A | 2/1982 | Stokes |
| 4,357,946 A | 11/1982 | Dutcher et al. |
| 4,369,791 A | 1/1983 | Friedman |
| 4,378,023 A | 3/1983 | Trabucco |
| 4,416,267 A | 11/1983 | Garren et al. |
| 4,452,254 A | 6/1984 | Goldberg et al. |
| 4,485,805 A | 12/1984 | Foster, Jr. |
| 4,592,339 A | 6/1986 | Kuzmak |
| 4,717,581 A | 1/1988 | Robblee |
| 4,823,808 A | 4/1989 | Clegg et al. |
| 4,975,682 A | 12/1990 | Kerr et al. |
| 5,074,868 A | 12/1991 | Kuzmak |
| 5,101,814 A | 4/1992 | Palti |
| 5,103,804 A | 4/1992 | Abel et al. |
| 5,105,812 A | 4/1992 | Corman |
| 5,188,104 A | 2/1993 | Wernicke et al. |
| 5,190,041 A | 3/1993 | Palti |
| 5,226,429 A | 7/1993 | Kuzmak |
| 5,234,454 A | 8/1993 | Bangs |
| 5,247,938 A | 9/1993 | Silverstein et al. |
| 5,263,480 A | 11/1993 | Wernicke et al. |
| 5,292,344 A | 3/1994 | Douglas |
| 5,314,461 A | 5/1994 | Borghi |
| 5,314,463 A | 5/1994 | Camps et al. |
| 5,368,028 A | 11/1994 | Palti |
| 5,423,872 A | 6/1995 | Cigaina |
| 5,449,368 A | 9/1995 | Kuzmak |
| 5,514,175 A | 5/1996 | Kim et al. |
| 5,540,730 A | 7/1996 | Terry et al. |
| 5,551,425 A | 9/1996 | Essen-Moller |
| 5,601,604 A | 2/1997 | Vincent |
| 5,654,030 A | 8/1997 | Munshi et al. |
| 5,690,691 A | 11/1997 | Chen et al. |
| 5,704,368 A | 1/1998 | Asano et al. |
| 5,716,385 A | 2/1998 | Mittal et al. |
| 5,741,211 A | 4/1998 | Renirie et al. |
| 5,792,210 A | 8/1998 | Wamubu et al. |
| 5,795,304 A | 8/1998 | Sun et al. |
| 5,836,994 A | 11/1998 | Bourgeois |
| 5,837,006 A | 11/1998 | Ocel et al. |
| 5,861,014 A | 1/1999 | Familoni |
| 5,868,141 A | 2/1999 | Ellias |
| 5,891,185 A | 4/1999 | Freed et al. |
| 5,919,216 A | 7/1999 | Houben et al. |
| 5,938,669 A | 8/1999 | Klaiber et al. |
| 5,979,449 A | 11/1999 | Steer |
| 5,991,649 A | 11/1999 | Garfield et al. |
| 5,995,872 A | 11/1999 | Bourgeois |
| 6,026,326 A | 2/2000 | Bardy |
| 6,041,258 A | 3/2000 | Cigaina et al. |
| 6,067,991 A | 5/2000 | Forsell |
| 6,083,249 A | 7/2000 | Familoni |
| 6,091,992 A | 7/2000 | Bourgeois |
| 6,092,528 A | 7/2000 | Edwards |
| 6,093,167 A | 7/2000 | Houben et al. |
| 6,104,955 A | 8/2000 | Bourgeois |
| 6,115,635 A | 9/2000 | Bourgeois |
| 6,129,685 A | 10/2000 | Howard |
| 6,132,372 A | 10/2000 | Essen-Moller |
| 6,135,978 A | 10/2000 | Houben |
| 6,185,452 B1 | 2/2001 | Schulman et al. |
| 6,216,045 B1 | 4/2001 | Black et al. |
| 6,243,607 B1 | 6/2001 | Mintchev |
| 6,249,697 B1 | 6/2001 | Asano et al. |
| 6,261,280 B1 | 7/2001 | Houben et al. |
| 6,270,455 B1 | 8/2001 | Brown |
| 6,321,124 B1 | 11/2001 | Cigaina |
| 6,334,073 B1 | 12/2001 | Levine |
| 6,363,937 B1 | 4/2002 | Hovda et al. |
| 6,381,495 B1 | 4/2002 | Jenkins |
| 6,405,732 B1 | 6/2002 | Edwards |
| 6,411,842 B1 | 6/2002 | Cigaina et al. |
| 6,415,178 B1 | 7/2002 | Ben-Haim et al. |
| 6,427,089 B1 | 7/2002 | Knowlton |
| 6,449,511 B1 | 9/2002 | Mintchev et al. |
| 6,454,699 B1 | 9/2002 | Forsell |
| 6,477,423 B1 | 11/2002 | Jenkins |
| 6,510,332 B1 | 1/2003 | Greenstein |
| 6,516,227 B1 | 2/2003 | Meadows et al. |
| 6,535,764 B2 | 3/2003 | Imran et al. |
| 6,571,127 B1 | 5/2003 | Ben-Haim et al. |
| 6,572,542 B1 | 6/2003 | Houben et al. |
| 6,584,348 B2 | 6/2003 | Glukhovsky |
| 6,591,137 B1 | 7/2003 | Fischell et al. |
| 6,600,953 B2 | 7/2003 | Flesler et al. |
| 6,606,523 B1 | 8/2003 | Jenkins |
| 6,609,025 B2 | 8/2003 | Barrett et al. |
| 6,612,983 B1 | 9/2003 | Marchal |
| 6,652,444 B1 | 11/2003 | Ross |
| 6,658,297 B2 | 12/2003 | Loeb |
| 6,684,104 B2 | 1/2004 | Gordon |
| 6,735,477 B2 | 5/2004 | Levine |
| 6,745,079 B2 | 6/2004 | King |
| 6,754,536 B2 | 6/2004 | Swoyer et al. |
| 6,826,428 B1 | 11/2004 | Chen et al. |
| 6,832,114 B1 | 12/2004 | Whitehurst |
| 6,852,110 B2 | 2/2005 | Roy et al. |
| 6,853,862 B1 | 2/2005 | Marchal et al. |
| 6,869,431 B2 | 3/2005 | Maguire et al. |
| 6,876,885 B2 | 4/2005 | Swoyer et al. |
| 6,895,279 B2 | 5/2005 | Loeb et al. |
| 6,918,871 B2 | 7/2005 | Schulze |
| 6,918,906 B2 | 7/2005 | Long |
| 6,939,349 B2 | 9/2005 | Fleischman et al. |
| 6,947,792 B2 | 9/2005 | Ben-Haim et al. |
| 6,952,613 B2 | 10/2005 | Swoyer et al. |
| 7,006,871 B1 | 2/2006 | Darvish et al. |
| 7,016,735 B2 | 3/2006 | Imran et al. |
| 7,043,295 B2 | 5/2006 | Starkebaum |
| 7,054,690 B2 | 5/2006 | Imran |
| 7,076,305 B2 | 7/2006 | Imran et al. |
| 7,076,306 B2 | 7/2006 | Marchal et al. |
| 2001/0011543 A1 | 8/2001 | Forsell |
| 2002/0026141 A1 | 2/2002 | Houben |
| 2002/0103424 A1 | 8/2002 | Swoyer et al. |
| 2002/0161414 A1 | 10/2002 | Flesler et al. |
| 2002/0165589 A1 | 11/2002 | Imran et al. |
| 2003/0045919 A1 | 3/2003 | Swoyer et al. |
| 2003/0055464 A1 | 3/2003 | Darvish |
| 2003/0055465 A1 | 3/2003 | Ben-Haim et al. |
| 2003/0055467 A1 | 3/2003 | Ben-Haim et al. |
| 2003/0066536 A1 | 4/2003 | Forsell |
| 2003/0114899 A1 | 6/2003 | Woods et al. |
| 2003/0135091 A1 | 7/2003 | Nakazawa et al. |
| 2003/0144708 A1 | 7/2003 | Starkebaum |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0220678 A1 | 11/2003 | Tronnes et al. |
| 2004/0044376 A1 | 3/2004 | Flesler et al. |
| 2004/0059393 A1 | 3/2004 | Policker et al. |
| 2004/0088023 A1 | 5/2004 | Imran et al. |
| 2004/0098068 A1 | 5/2004 | Carbunaru et al. |
| 2004/0106963 A1 | 6/2004 | Tsukamoto et al. |
| 2004/0107004 A1 | 6/2004 | Levine et al. |
| 2004/0147816 A1 | 7/2004 | Policker et al. |
| 2004/0158138 A1 | 8/2004 | Kilcoyne et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0236316 A1 | 11/2004 | Danitz et al. |
| 2004/0243195 A1 | 12/2004 | Imran et al. |
| 2004/0243211 A1* | 12/2004 | Colliou et al. ............... 607/133 |
| 2004/0249421 A1 | 12/2004 | Harel et al. |
| 2005/0021101 A1 | 1/2005 | Chen et al. |
| 2005/0055038 A1 | 3/2005 | Kelleher et al. |
| 2005/0065505 A1 | 3/2005 | Ryan |
| 2005/0075654 A1 | 4/2005 | Kelleher |
| 2005/0090873 A1 | 4/2005 | Imran |

| | | |
|---|---|---|
| 2005/0096514 A1 | 5/2005 | Starkebaum |
| 2005/0107829 A1 | 5/2005 | Edwards et al. |
| 2005/0143784 A1 | 6/2005 | Imran |
| 2005/0164925 A1 | 7/2005 | Jakubowski et al. |
| 2005/0183732 A1 | 8/2005 | Edwards |
| 2005/0192615 A1 | 9/2005 | Torre et al. |
| 2005/0203500 A1 | 9/2005 | Saadat |
| 2005/0209653 A1 | 9/2005 | Herbert et al. |
| 2005/0222638 A1 | 10/2005 | Foley et al. |
| 2005/0251219 A1 | 11/2005 | Evans |
| 2006/0064037 A1 | 3/2006 | Shalon et al. |
| 2006/0074459 A1 | 4/2006 | Flesler et al. |
| 2006/0085045 A1 | 4/2006 | Harel et al. |
| 2006/0089690 A1 | 4/2006 | Gerber |
| 2006/0142803 A1 | 6/2006 | Mintchev |
| 2006/0173238 A1 | 8/2006 | Starkebaum |
| 2006/0184207 A1 | 8/2006 | Darvish et al. |
| 2006/0247718 A1 | 11/2006 | Starkebaum |
| 2006/0264699 A1 | 11/2006 | Gartner |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0092446 A1 | 4/2007 | Haddad et al. |
| 2007/0156177 A1 | 7/2007 | Harel et al. |
| 2007/0179556 A1 | 8/2007 | Ben Haim et al. |
| 2007/0185540 A1 | 8/2007 | Ben-Haim et al. |
| 2007/0299320 A1 | 12/2007 | Policker et al. |
| 2008/0046062 A1* | 2/2008 | Camps et al. ............... 607/133 |
| 2008/0058889 A1 | 3/2008 | Ben-Haim et al. |
| 2008/0058891 A1 | 3/2008 | Ben-Haim et al. |
| 2008/0065168 A1 | 3/2008 | Bitton et al. |
| 2008/0178684 A1 | 7/2008 | Spehr |
| 2009/0062893 A1 | 3/2009 | Spehr et al. |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2010/0228105 A1 | 9/2010 | Policker et al. |
| 2010/0305468 A1 | 12/2010 | Policker et al. |
| 2010/0324644 A1 | 12/2010 | Levi et al. |

FOREIGN PATENT DOCUMENTS

| | | |
|---|---|---|
| EP | 1036545 | 9/2000 |
| EP | 1 447 052 | 8/2004 |
| JP | 2003/319945 | 11/2003 |
| WO | WO 94/01172 | 1/1994 |
| WO | WO 97/25098 | 7/1997 |
| WO | WO97/41921 | 11/1997 |
| WO | WO 98/10830 | 3/1998 |
| WO | WO 99/03533 | 1/1999 |
| WO | WO 00/53257 | 9/2000 |
| WO | WO 01/10375 | 2/2001 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 03/045493 | 6/2003 |
| WO | WO 2004/021858 | 3/2004 |
| WO | WO 2004/043280 | 5/2004 |
| WO | WO 2004/066903 | 8/2004 |
| WO | WO 2004/069330 | 8/2004 |
| WO | WO 2004/091361 | 10/2004 |
| WO | WO 2004/096337 | 11/2004 |
| WO | WO 2004/112563 | 12/2004 |
| WO | WO 2004/112883 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2006/018851 | 2/2006 |
| WO | WO 2006/035446 | 4/2006 |
| WO | WO2006/045075 | 4/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/118790 | 11/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

An Office Action dated Aug. 2, 2011 which issued during the prosecution of U.S. Appl. No. 11/915,647.

An International Search Report and a Written Opinion both dated Oct. 28, 2008 which issued during the prosecution of Applicant's PCT/IL08/00646.

A Supplementary Partial European Search Report dated Mar. 3, 2009 which issued during the prosecution of European Patent Application No. 02727012.

An Office Action dated Oct. 24, 2008 which issued during the prosecution of European Patent Application No. 02724592.

An Office Action dated Apr. 7, 2009 which issued during the prosecution of European Patent Application No. 06748690.

Jaremko, et al., "Advances toward the implantable artificial pancreas for treatment of diabetes", Diabetes Care, 21(3), Mar. 1998.

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II. Mitochondrial variables", American Journal of Physiology, 274(4 Pt 1): C1174-1184, Apr. 1998.

Yamada, "Effects of drugs on electromechanical activities of the stomach and duodenum of conscious dogs", Nippon Heikatsukin Gakkai Zasshi. Feb. 1983;19(1):25-35. (abstract only).

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

Shemerovskii KA, "Effect of feeding on the activity of duodenal smooth muscle in dogs", Biull Eksp Biol Med. Oct. 1978;86(10):394-7. (Abstract only).

Swain et al., in "An endoscopically deliverable tissue-transfixing device for securing biosensors in the gastrointestinal tract", Gastrointestinal Endoscopy 40(6): 730-734 (1994).

Kalloo AN et al. (2004) Flexible transgastric peritoneoscopy: a novel approach to diagnostic and therapeutic interventions. Gastrointest Endosc 60: 114-117.

Park PO et al. (2005) Experimental studies of transgastric gall bladder surgery: cholecystectomy and cholecystogastric anastomosis. Gastrointest Endosc 61: 601-606.

Kantsevoy SV et al. (2006) Transgastric endoscopic splenectomy: Is it possible? Surg Endosc 20:522-526.

Rattner D, Kalloo A, et al. (2006) White Paper: ASGE/SAGES Working Group on Natural Orifice Transluminal Endoscopic Surgery. Surg Endosc 20:329-333.

Stein et al., "Carrots and sticks: Impact of an incentive/disincentive employee flexible credit benefit plan on health status and medical costs", American Journal of Health Promotion, May/Jun. 1999, V5, 113, 5.

Giuffrida, "Should we pay the patient? Review of financial incentives to enhance patient compliance", Biomedical Journal, vol. 315, pp. 703-707, 1997.

An abstract entitled "Gastric myoelectrical pacing as therapy for morbid obesity: Preliminary results", by Cigaina, et al., Dec. 24, 2000.

An abstract entitled "Implantable gastric stimulator (IGS) as therapy for morbid obesity: Equipment, surgical technique and stimulation parameters", by Cigaina, et al., Dec. 24, 2000.

http://medical-dictionary.thefreedictionary.com/pyloric+antrum, within the Free Dictionary.com, downloaded on Jun. 5, 2012.

An Office Action dated Feb. 1, 2012, which issued during the prosecution of U.S. Appl. No. 11/915,647.

An Office Action dated May 10, 2012, which issued during the prosecution of U.S. Appl. No. 11/915,647.

An Office Action dated May 10, 2012, which issued during the prosecution of U.S. Appl. No. 10/599,015.

An Office Action dated Sep. 27, 2011, which issued during the prosecution of U.S. Appl. No. 10/599,015.

* cited by examiner

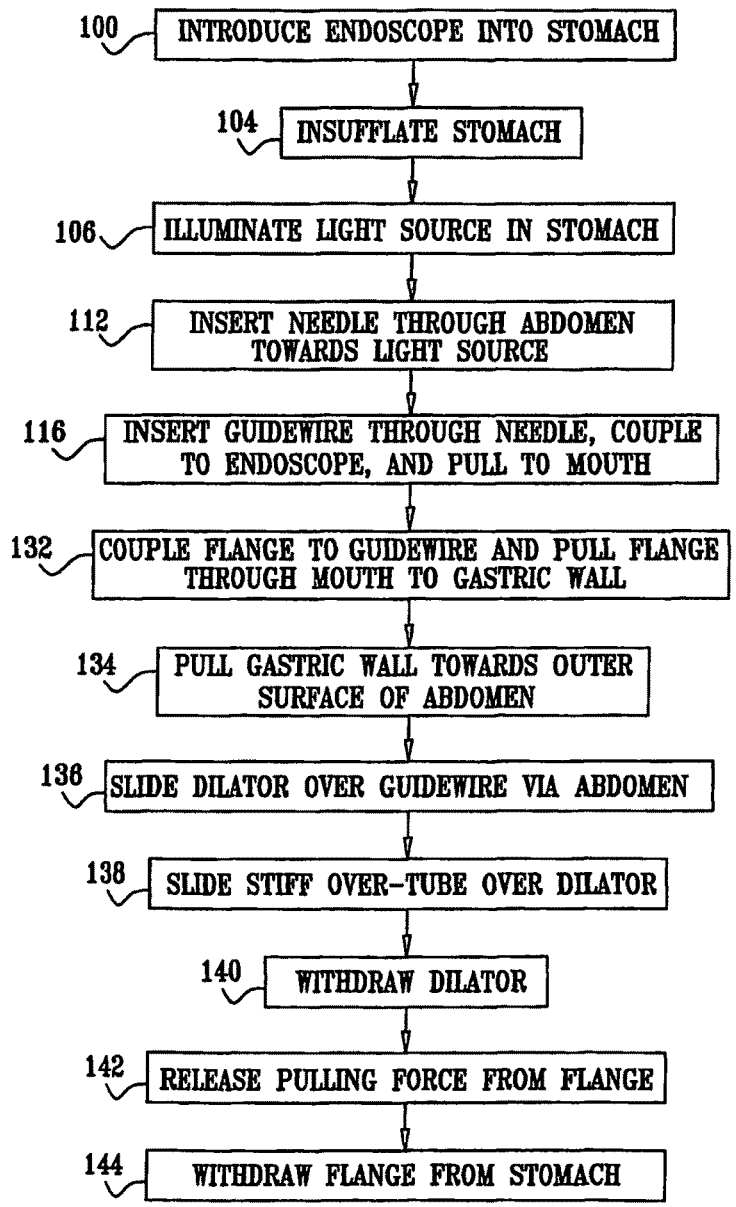

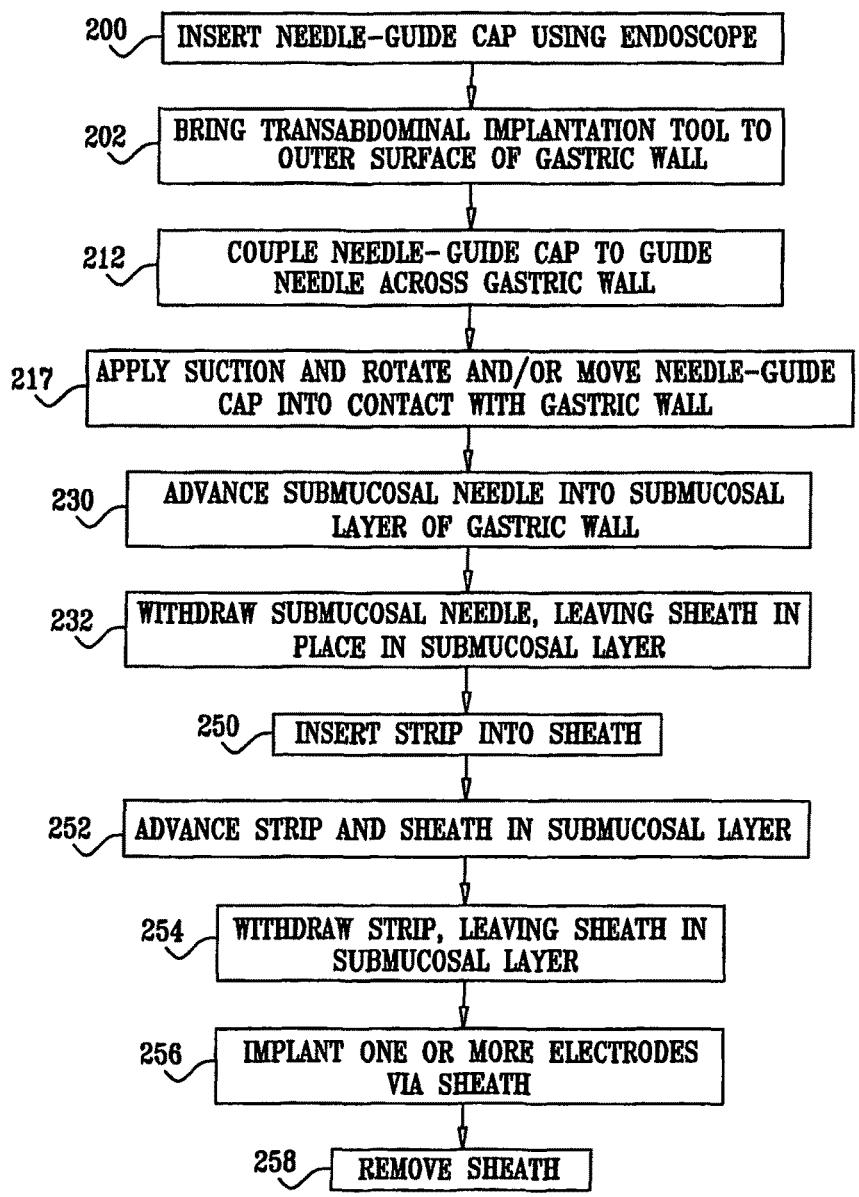

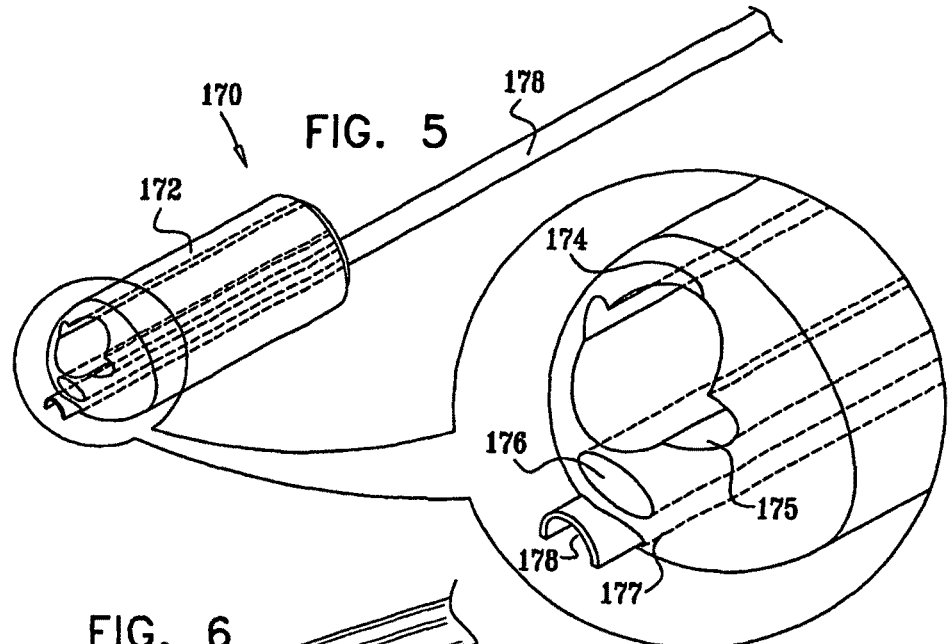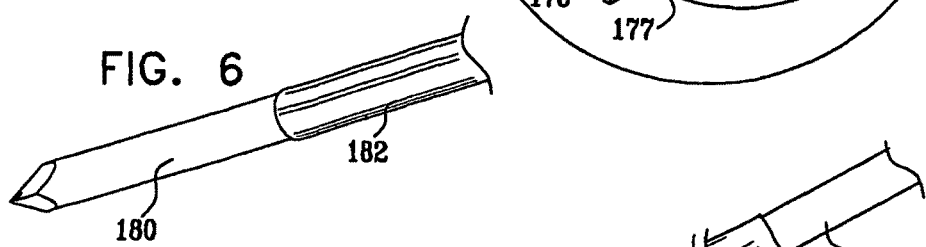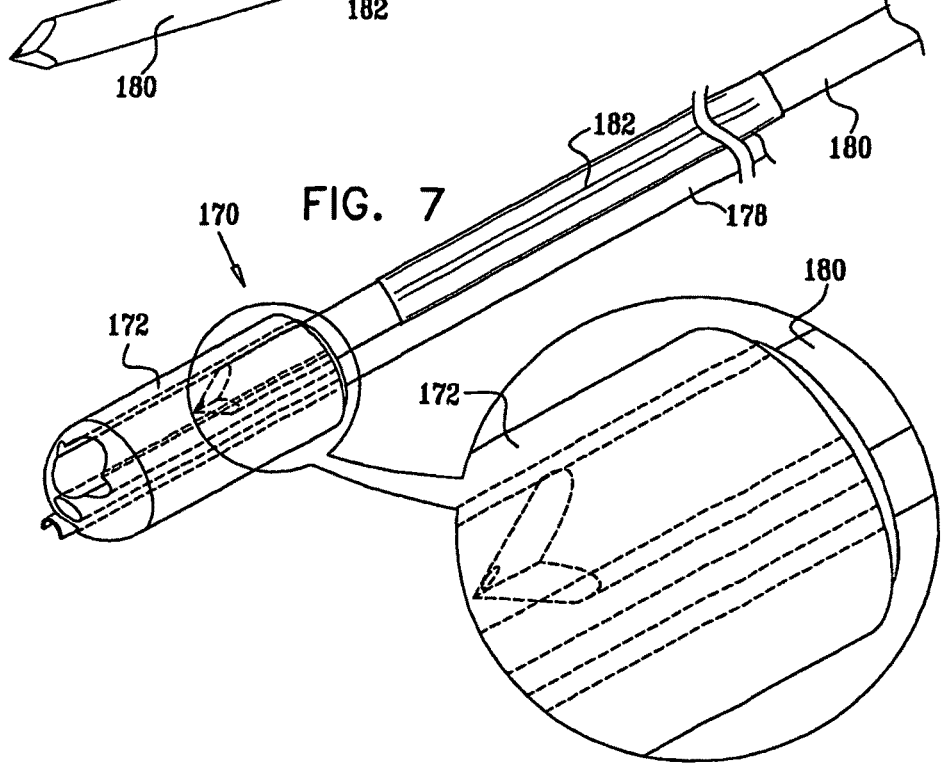

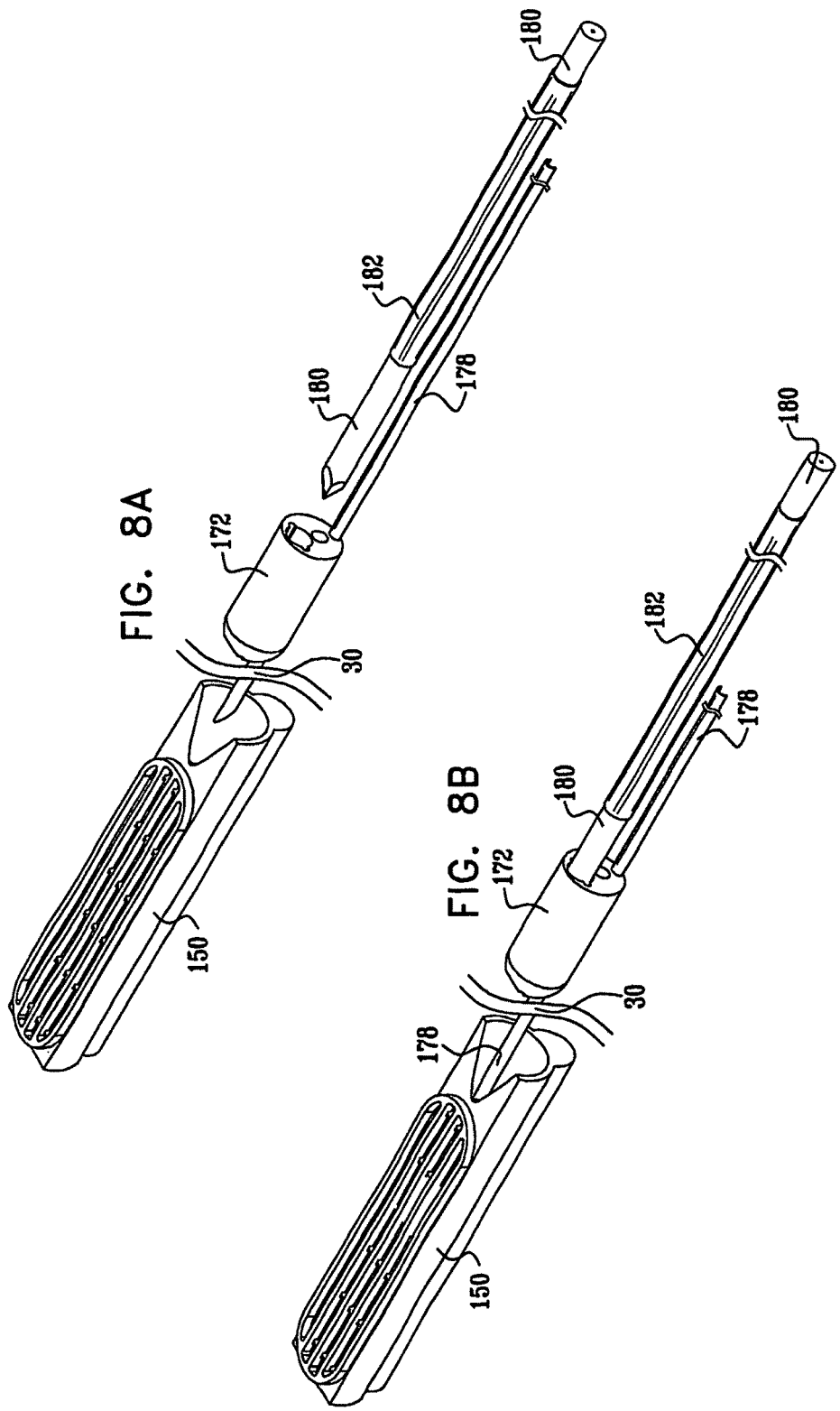

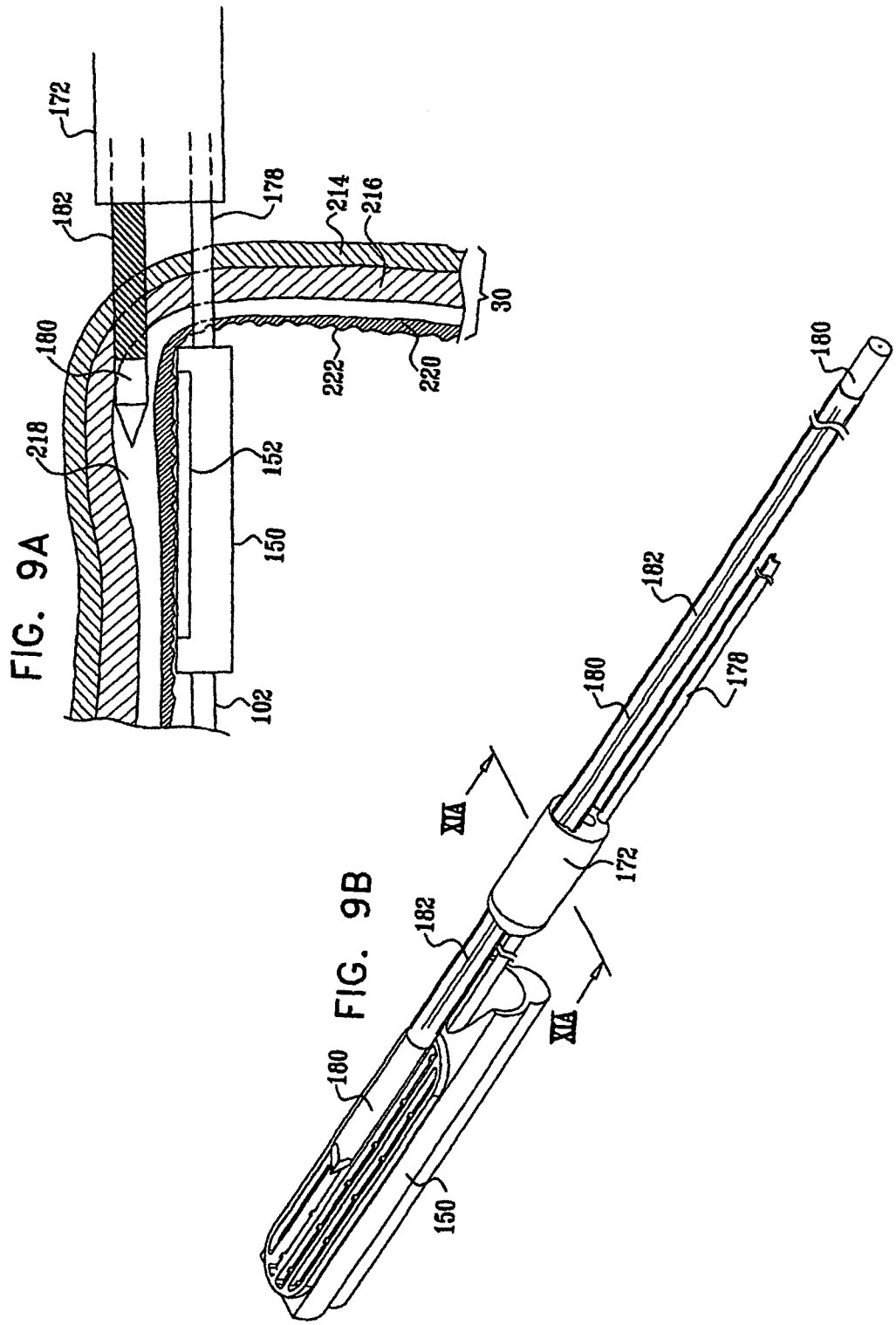

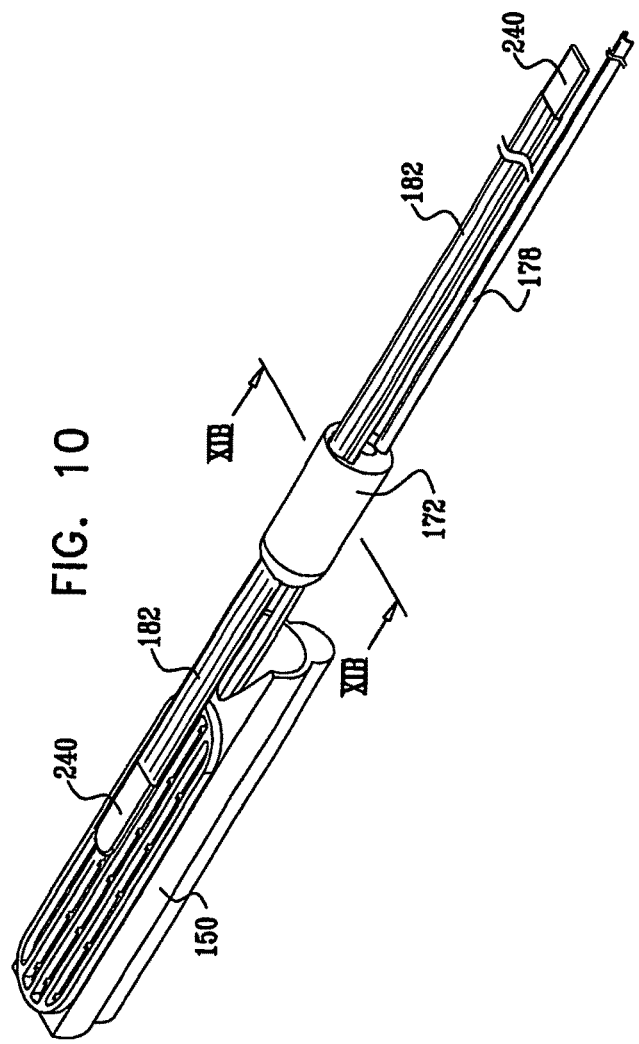

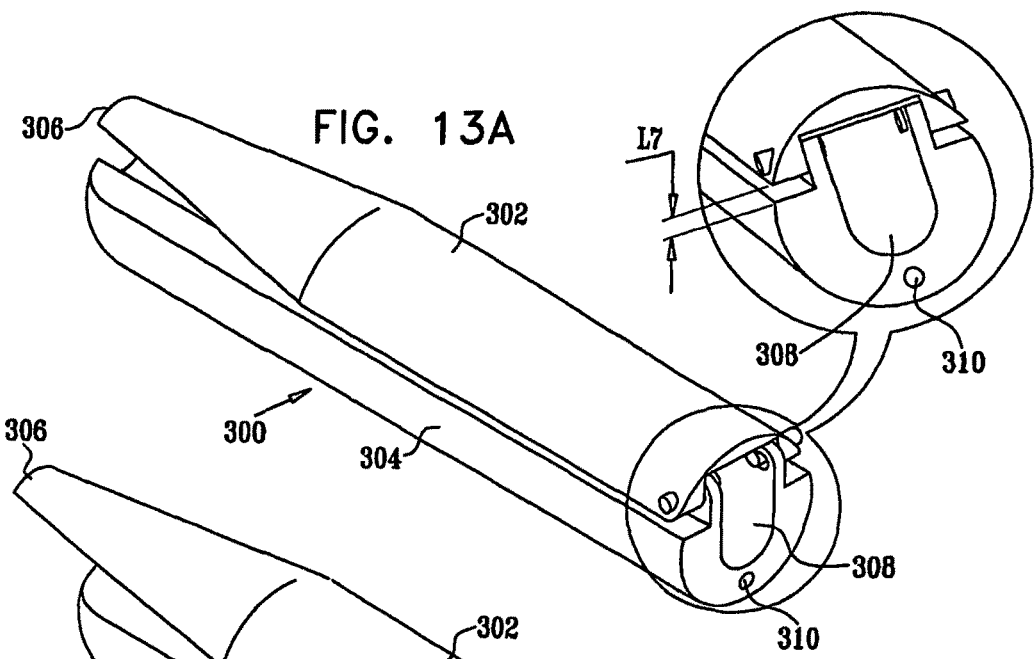
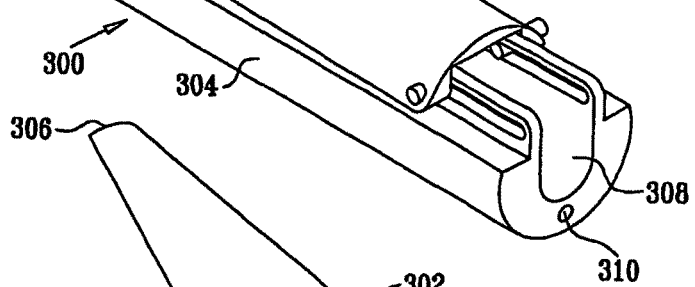
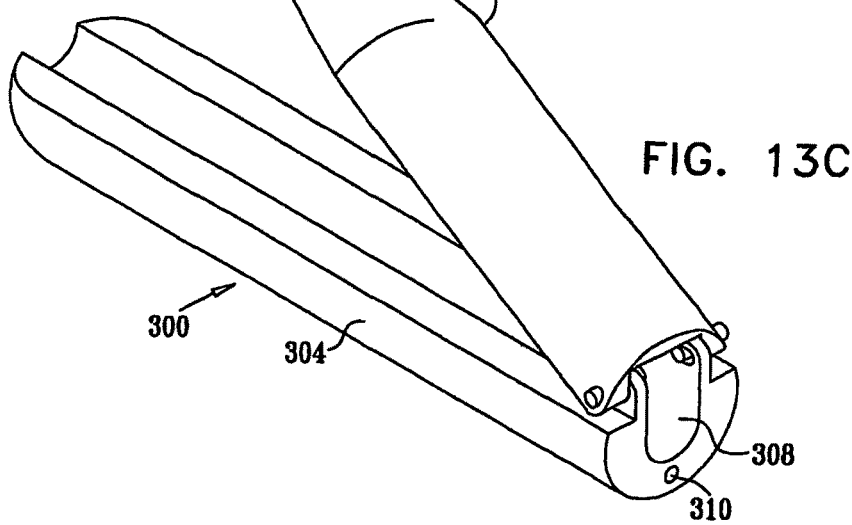

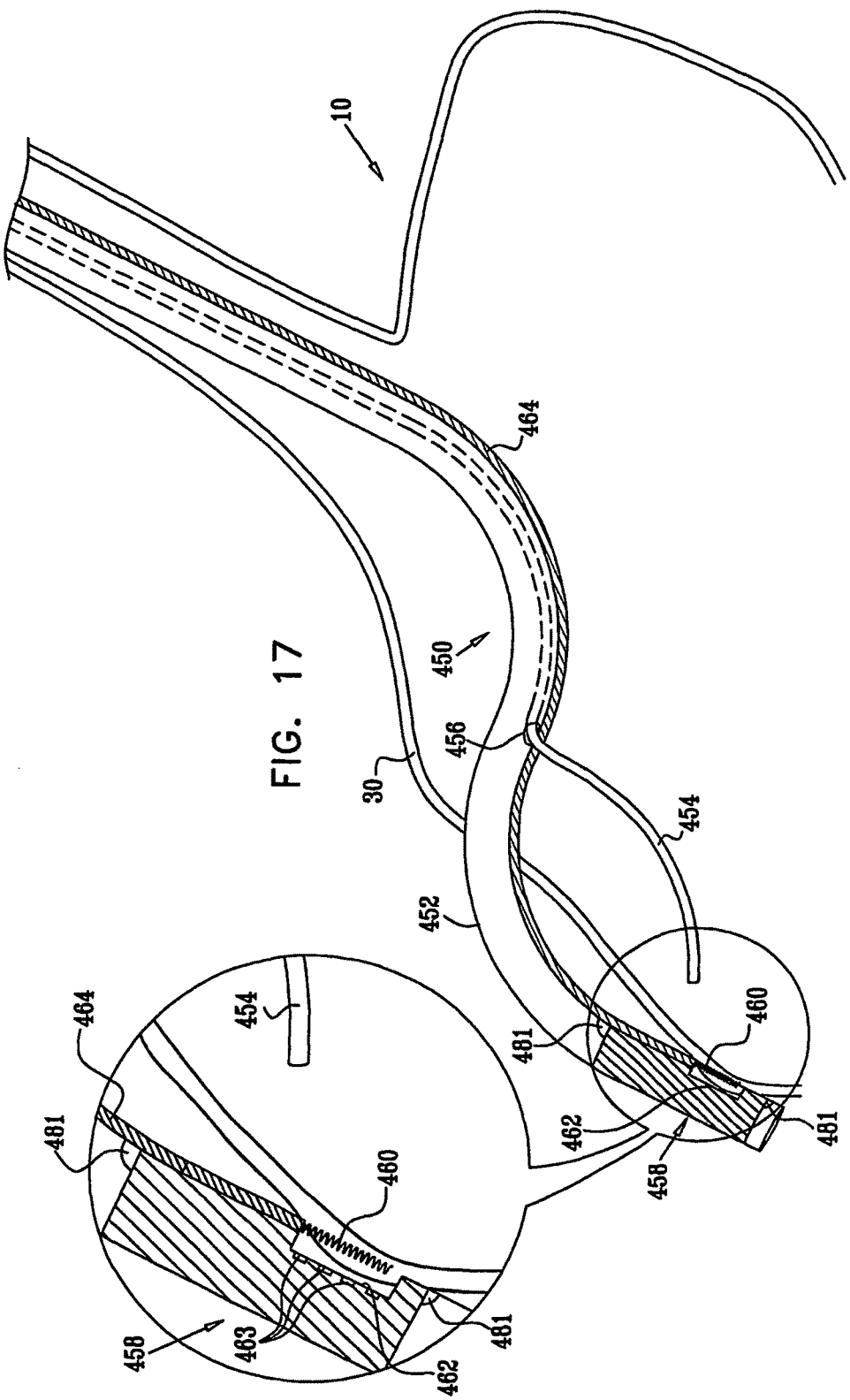

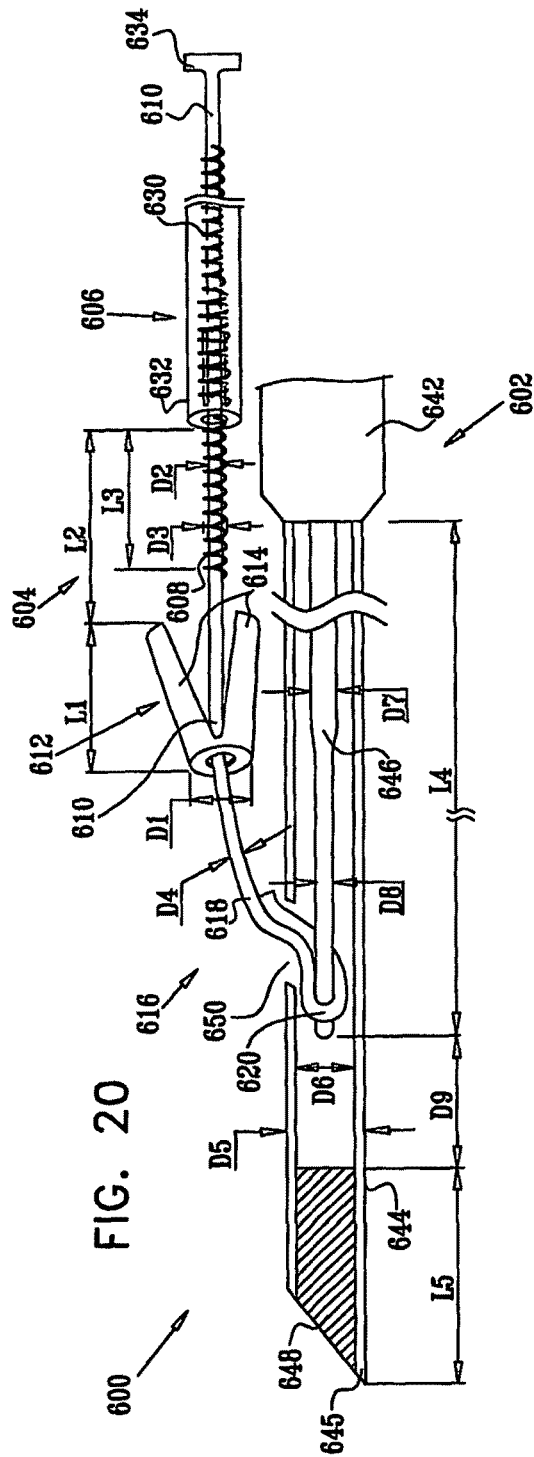
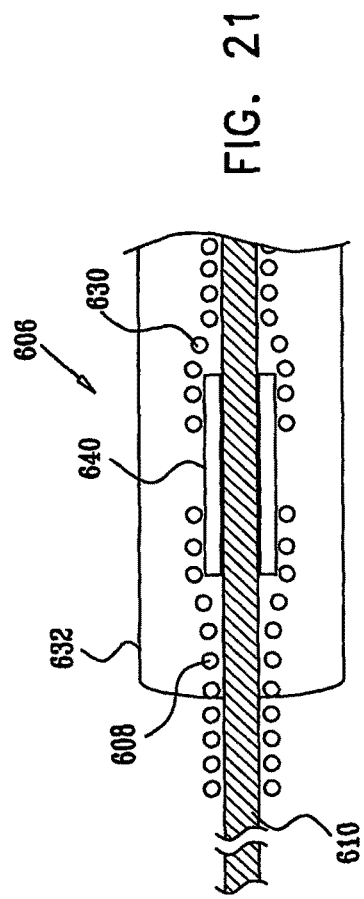
FIG. 20
FIG. 21

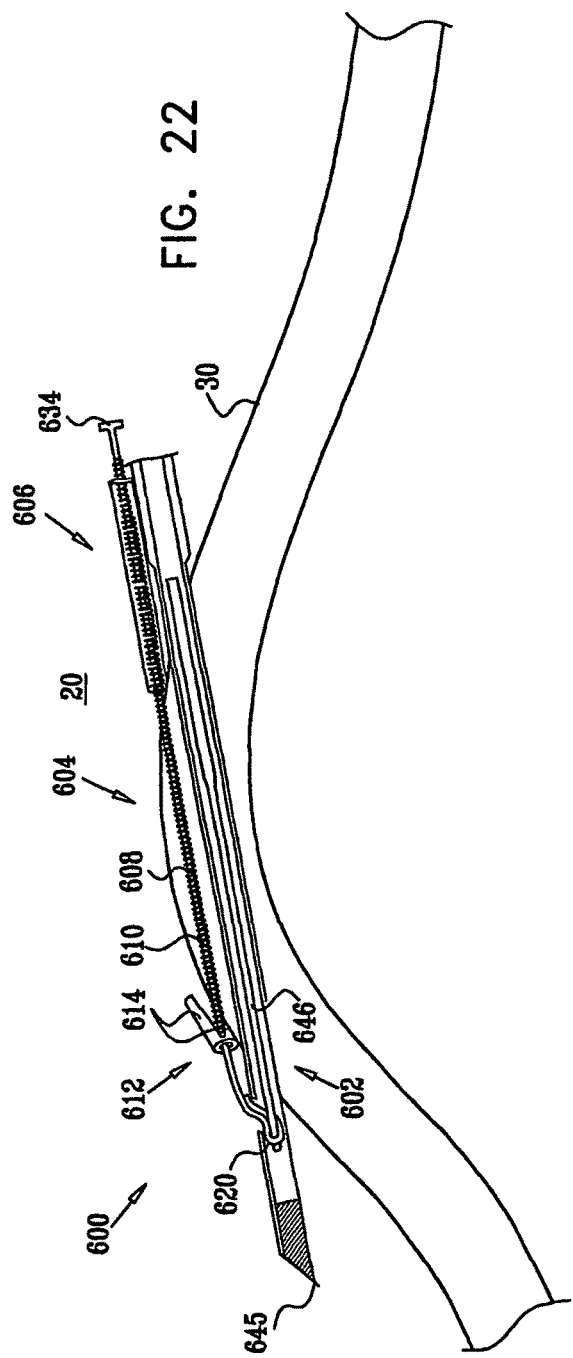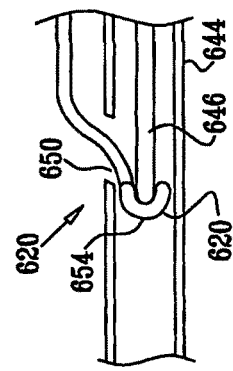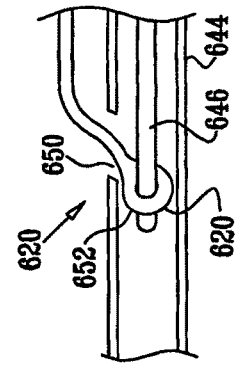

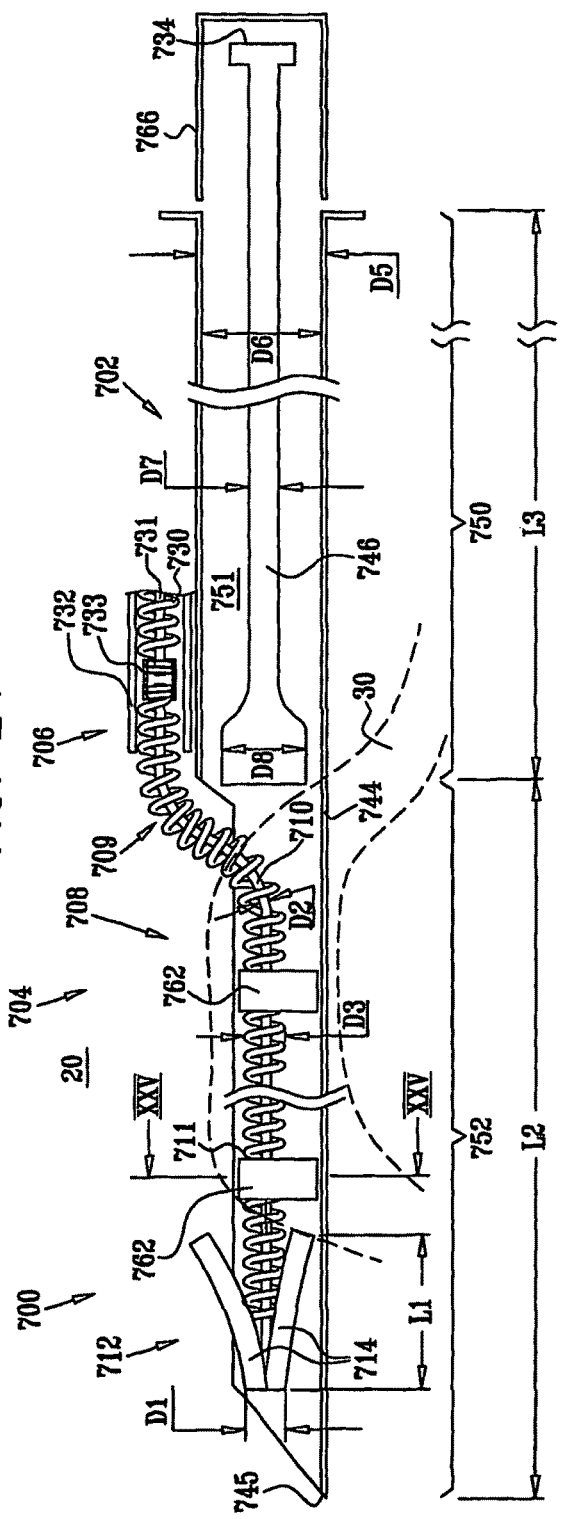
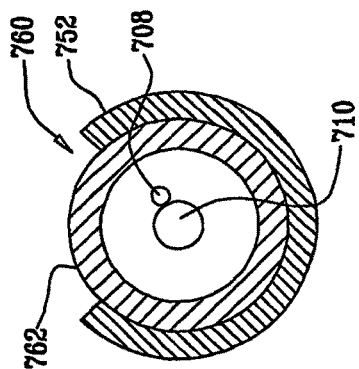
FIG. 24
FIG. 25

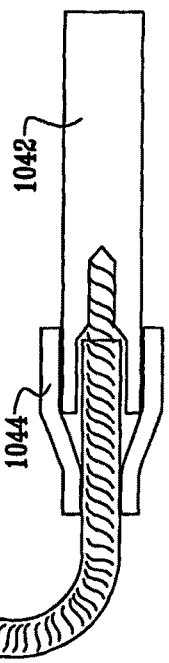
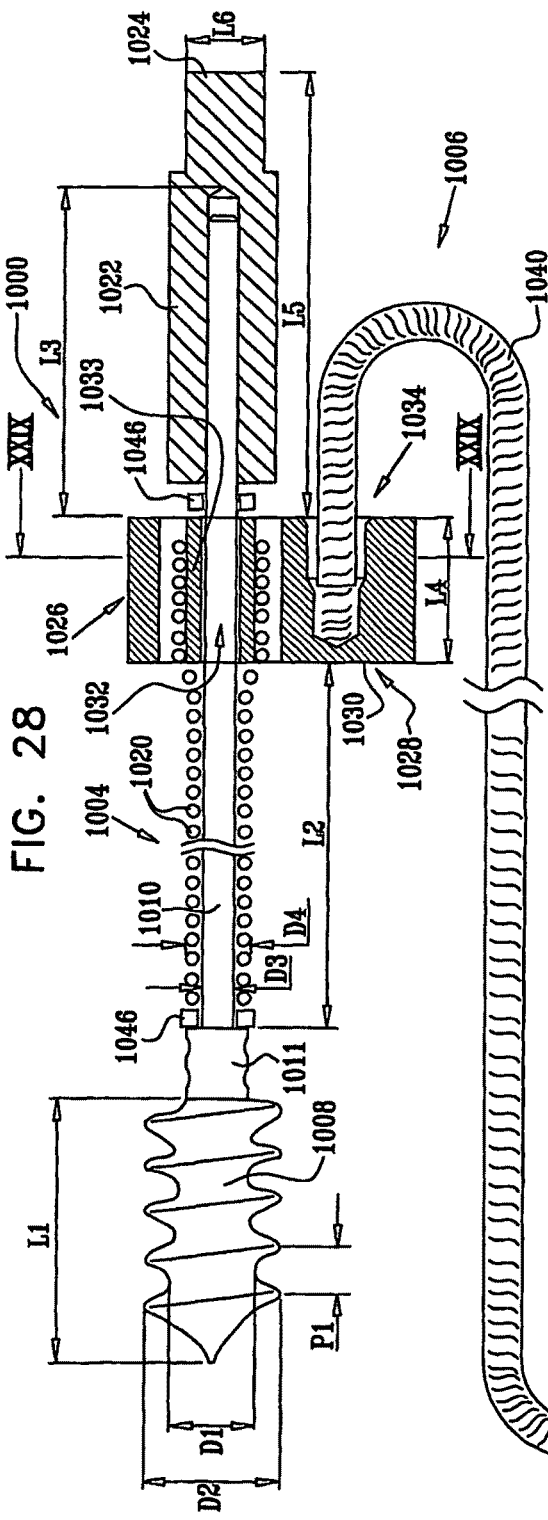
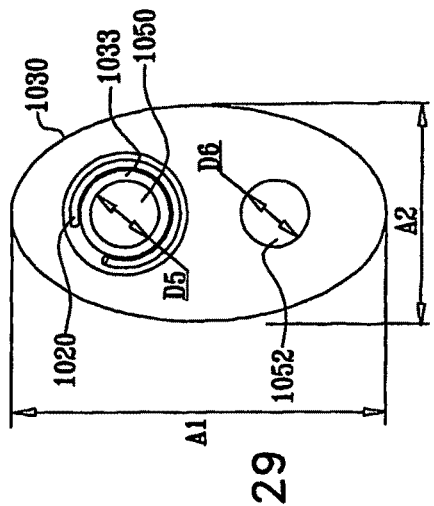
FIG. 28
FIG. 29

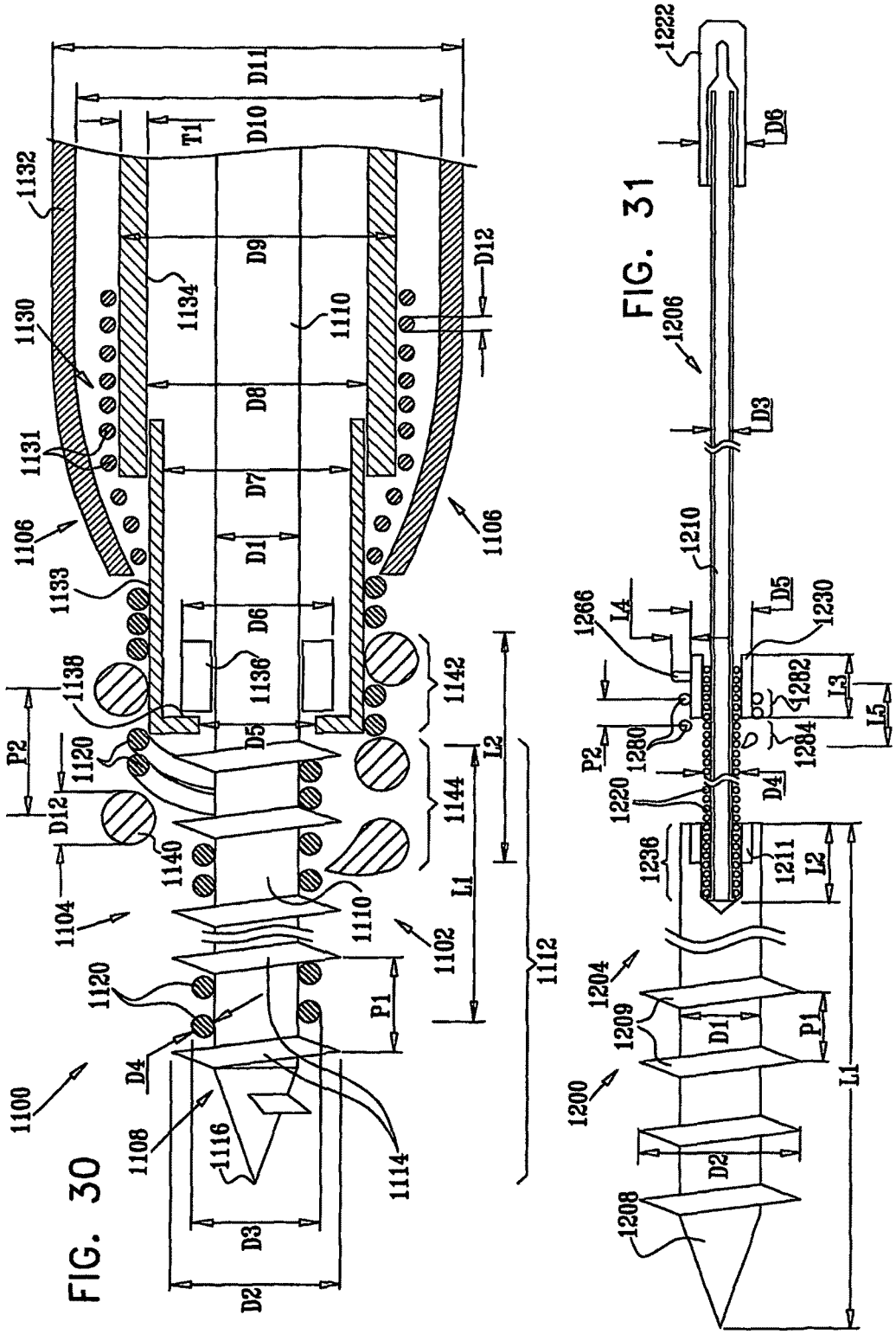

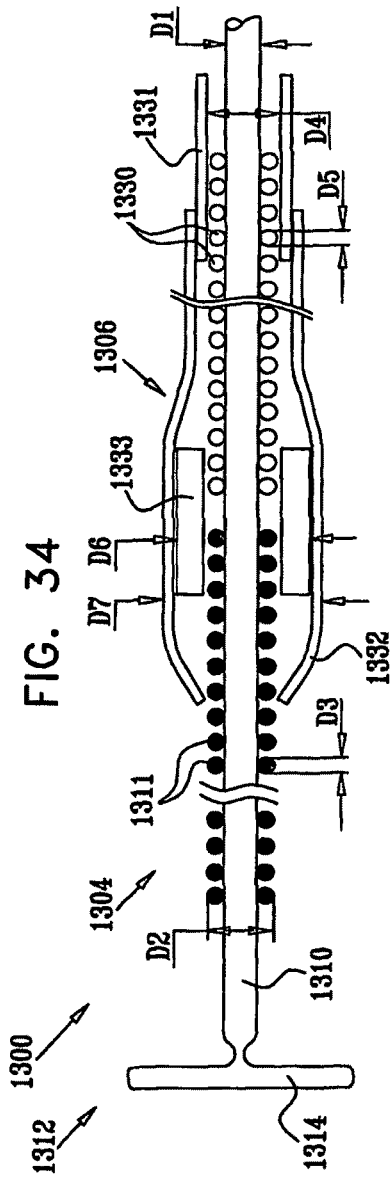
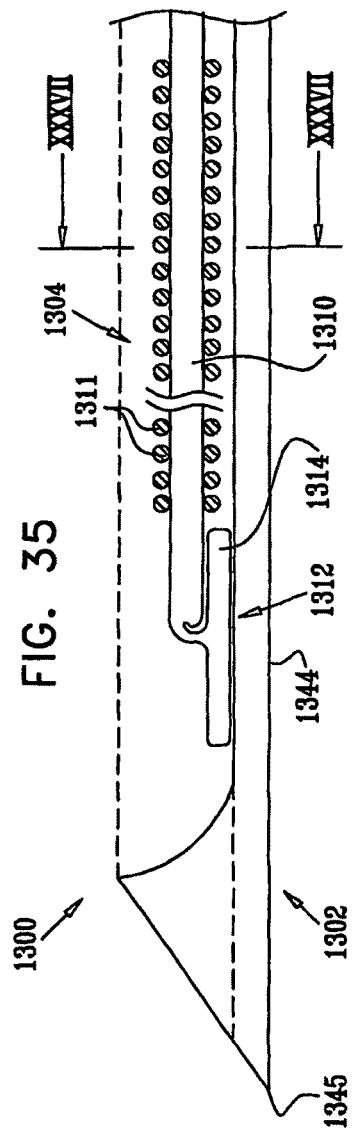

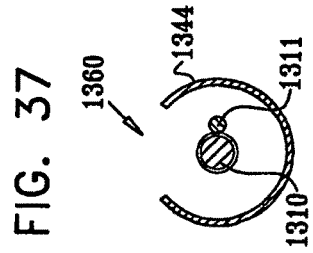
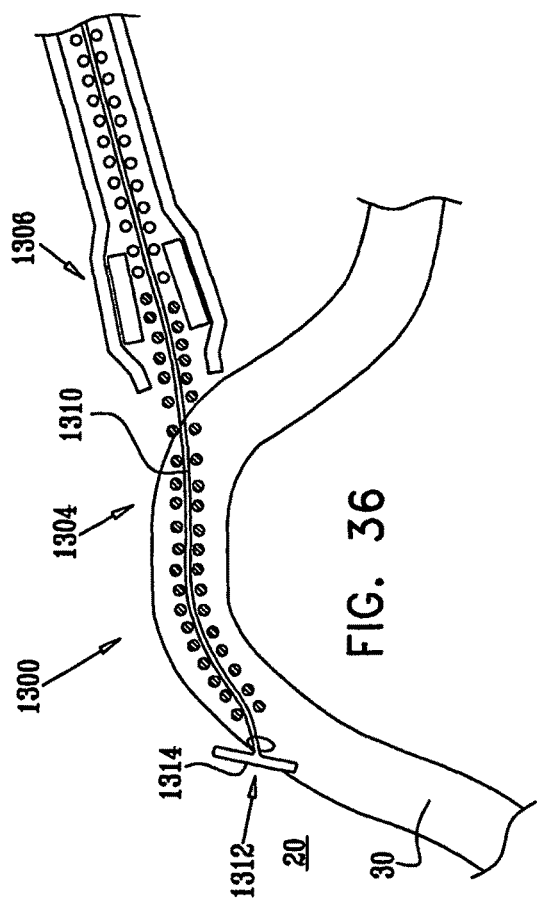
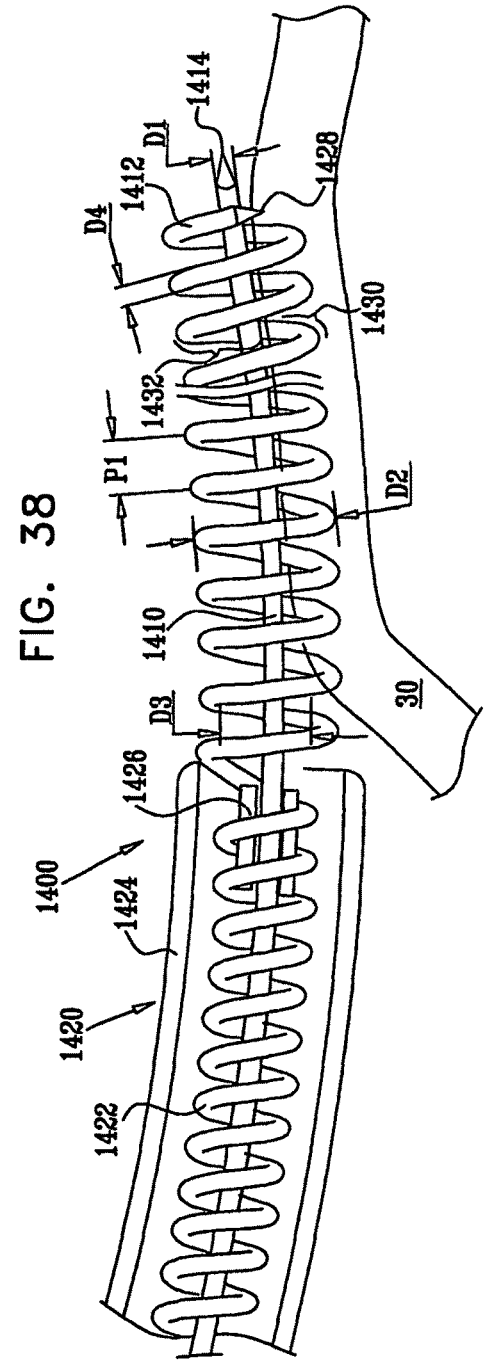

ELECTRODE ASSEMBLIES, TOOLS, AND METHODS FOR GASTRIC WALL IMPLANTATION

CROSS-REFERENCES TO RELATED APPLICATIONS

The present application is a U.S. national phase of PCT Application No. PCT/IL07/000,052 to Levi et al., filed Jan. 14, 2007, which:

(i) claims the benefit of U.S. 60/758,937 to Levi et al., filed Jan. 12, 2006, entitled, "Electrode assemblies, tools, and methods for gastric wall implantation,"

(ii) is a continuation-in-part of PCT Patent Application PCT/US2006/010911 (WO 06/102626) to Policker et al., filed Mar. 24, 2006, which claims priority from U.S. 60/665,320 to Policker et al., filed Mar. 24, 2005, and (iii) is a continuation-in-part of PCT Patent Application PCT/IL2006/000644 (WO 06/129321) to Policker et al., filed Jun. 4, 2006, entitled, "GI lead implantation," which (a) claims priority from U.S. 60/687,099 to Mika et al., filed Jun. 2, 2005, and (b) is a continuation-in-part of PCT Patent Application PCT/US2006/010911 to Policker et al., filed Mar. 24, 2006, entitled, "Wireless leads for gastrointestinal tract applications."

Each of the above applications is assigned to the assignee of the present patent application and is incorporated herein by reference.

FIELD OF THE INVENTION

The present invention relates generally to minimally-invasive surgical tools, methods, and apparatus, and specifically to minimally-invasive surgical tools and methods for implanting electrodes in a gastric wall.

BACKGROUND OF THE INVENTION

Various treatment techniques require the implantation of electrodes in, on, or around a portion of the gastrointestinal (GI) tract. Such electrodes are often implanted subserosally or submucosally.

U.S. Pat. No. 6,826,428 to Chen et al., which is incorporated herein by reference, describes a method for regulating gastrointestinal (GI) action in a subject using a stimulatory electrode and a sensor to provide retrograde feedback control of electrical stimulation to the GI tract. The '428 patent also describes a method which uses a needle to insert a device, such as an electrode, into the GI tract or the GI wall of a subject, from the exterior of the subject. The method for inserting the device in the GI wall includes inserting the needle until its end is positioned in the thickness of the GI wall, and inserting the device through an interior bore of the needle, such that engaging means of the device extends beyond the interior bore of the needle into the thickness of the wall. The needle is then removed, and the device is retracted until the engaging means engages the thickness of the wall.

US Patent Application Publication 2005/0251219 to Evans, which is incorporated herein by reference, describes endoscopic apparatus and methods for placement of electrodes in the gastric wall. The apparatus has one or more electrodes disposed on an elongated body having a pointed first end and a bolster disposed on a second end. When placed within the GI tract, the first end of the apparatus extends through the gastric and abdominal walls, extending outside of the patient's body with the bolster in contact against the inner lining of the gastric wall to retain the apparatus. Exposed electrodes contact the gastric smooth muscle. Insulated wires in electrical connection with the electrodes run the length of the apparatus body. Once the apparatus is placed, the first end of the apparatus body is removed to expose the wires, allowing electrical connection to an external electrical signal generator to provide electrical stimulus.

US Patent Application Publication 2005/0192615 to Torre et al., which is incorporated herein by reference, describes a space-occupying device for deployment within a patient's stomach and methods of deploying and removing the device. The device includes an expandable member and fasteners, such as sutures, that extend to least partially through the patient's stomach wall, and that anchor the device with the patient's stomach. The device can be deployed and/or removed through transesophageal approaches and/or through a combination of transesophageal and transabdominal approaches.

US Patent Application Publication 2005/0143784 to Imran, which is incorporated herein by reference, describes techniques for anchoring a device to a stomach. The anchor of the device is constructed to resist pull out forces.

U.S. Pat. No. 6,535,764 to Imran et al., which is incorporated herein by reference, describes techniques for diagnosing and treating gastric disorders. A functional device resides within the patient's stomach and is secured to the stomach wall by an attachment device. In an embodiment, the device comprises an anchor which comprises a screw connector, which includes an electrode.

U.S. Pat. No. 6,606,523 to Jenkins, which is incorporated herein by reference, describes apparatus for stimulating neuromuscular tissue of the gastrointestinal tract, and methods for installing the apparatus to the surface of the neuromuscular tissue. A pair of electrodes are supported by an electrode attachment member having a distal surface configured for attachment to the surface of the neuromuscular tissue. The electrodes are supported adjacent the distal surface to provide an interface between the electrodes and the surface of the neuromuscular tissue. The electrode attachment member may be flexible to pass through a laparoscopic surgical access opening in a compacted form and then returned to an uncompacted form for attachment to the surface of the neuromuscular tissue by the use of staples or sutures. In an embodiment, an electrode assembly is provided with a substantially helical or corkscrew-type attachment member protruding from a distal surface of a patch. The helical attachment member may also serve as an electrode for stimulating the neuromuscular tissue.

U.S. Pat. No. 6,041,258 to Cigaina et al., which is incorporated herein by reference, describes a handle for an implant device used in laparoscopic surgery. The implant device is used for electrostimulation and/or electrical monitoring of endo-abdominal tissue or viscera. The implant device has an elongated body equipped with devices to secure it to the tissue to be treated and two or more electric poles that are electrically connected to an electric connection terminal for connection to a power source, means to penetrate the tissue to be treated, and quick-release connecting devices to separate the penetration device from the elongated body. The handle, which is an elongated body, is attached to the proximal end of the implant device or other medical device and has a grasping means at its opposite end for manipulation with laparoscopic forceps.

US Patent Application Publication 2003/0195600 to Tronnes et al., which is incorporated herein by reference, describes an implantable intramuscular lead system, such as for use as a gastric lead, and method of use in which electrodes along the lead are imbedded in tissue. First and second anchors are mounted on an elongate lead. At least the second anchor is movable along the length of the lead relative to the first anchor to capture the tissue between the anchors so that the lead is retained in position. The system facilitates implantation of the lead in tissue, and is described as being particularly suited for minimally invasive implantation, such as laparoscopically.

US Patent Application Publication 2005/0209653 to Herbert et al., which is incorporated herein by reference, describes an intra-luminal device for gastrointestinal electrical stimulation that is self-powered and self-contained within a capsule-like housing, and is capable of non-surgical implantation within the patient. The device includes an implantable pulse generator and one or more electrodes mounted within a common device housing. The device housing is capable of endoscopic introduction to a desired location within the gastrointestinal tract, such as the stomach, via the esophagus. In an embodiment, a stimulation device is secured within the gastrointestinal tract with a fixation mechanism using a vacuum cavity and pin to secure tissue.

U.S. Pat. No. 6,952,613 to Swoyer et al., which is incorporated herein by reference, describes active fixation, gastrointestinal leads adapted to be implanted within the body at a site of the GI tract for performing electrical stimulation and sensing. Described active fixation mechanisms include one or more of hooks, and helixes extending from stops, e.g. plates, of an electrode head and functioning as stimulation/sense electrodes in unipolar and bipolar configurations or simply as fixation mechanisms.

US Patent Application Publication 2002/0103424 to Swoyer et al., which is incorporated herein by reference, describes a GI tract stimulator and/or monitor implantable medical device (IMD) comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

US Patent Application Publication 2005/0055038 to Kelleher et al., which is incorporated herein by reference, describes a device and method for selectively engaging or penetrating a layer of a luminal organ wall where the luminal organ wall has a plurality of layers including an outermost layer and an innermost layer adjacent to the lumen of the organ. The device and method select one of the plurality of layers of the organ wall other than the innermost layer and deploy from within the lumen of the organ a tissue device through the innermost layer to a specific depth to engage or penetrate the selected one of the plurality of layers. The device and method may be employed to create luminal pouches or restrictive outlets. In a stomach organ, the device and methods may be employed to treat obesity by forming a gastric pouch with or without a restrictive outlet. In an embodiment, a securement device comprises a hollow needle which passes through a stomach wall into a safety gap between the outer surface of the wall and the liver, and which deploys a thread having a T-anchor on its end. In another embodiment, a restrictive outlet to a gastric pouch is created using a mucosal bunching device which is generally egg shaped, and has (a) a distal anvil, (b) an interior space into which mucosa is sucked using suction applied through vacuum ports, (c) a radial array of staples, and a (d) staple pusher 546. By deploying the device into the outlet of a gastric pouch and applying suction through the ports, the mucosa is sucked into the stapling space, and the staples are then pushed through the mucosa and formed against the anvil.

U.S. Pat. No. 6,363,937 to Hovda et al., which is incorporated herein by reference, describes techniques for selectively applying electrical energy to a target location within the gastrointestinal tract, such as the lower esophageal sphincter (LES). In an embodiment, the electrosurgical instrument comprises a catheter designed for advancement through the patient's mouth, down the esophagus into the region of the lower sphincter. In this embodiment, the catheter may optionally include an endoscope, or the system may include a separate endoscope.

PCT Publication WO 05/037152 to Stack et al., which is incorporated herein by reference, describes techniques for retaining a medical implant within a body cavity.

PCT Publication WO 02/089655 to Imran et al., which is incorporated herein by reference, describes techniques for diagnosing and treating gastric disorders. A submucosal gastric implant device is placed within the submucosal layer of a patient's stomach wall. The device in one embodiment provides electrical stimulation of the stomach wall and may use multiple electrode pairs for sequential stimulation. The device may also have other functional aspects such as a sensor for sensing various parameters of the stomach or stomach environment, or a therapeutic delivery device.

PCT Publication WO 05/041749 to Imran, which is incorporated herein by reference, describes a fixation device for holding stimulating electrodes in electrical contact with the wall of a portion of the gastrointestinal tract. In one embodiment, the fixation device includes an expandable member that fixes the electrodes in electrical contact with the gastrointestinal tract wall. Also described is an implantable device and method for controlling the opening and/or closing of the pylorus. In particular, a device and method is described for stimulating the duodenum to control the closing/and or opening of the pylorus. Finally, a method is described for treating obesity by controlling the pylorus to retain food in the stomach for a desired period of time, among other things to provide a feeling of satiety and/or to reduce hunger. One aspect includes controlling the pylorus's contraction by electrical stimulation of the duodenum.

US Patent Application Publication 2004/0158138 to Kilcoyne et al., which is incorporated herein by reference, describes an ambulatory system for monitoring one or more physiological parameters in a body lumen, such as the esophagus. The system includes an implantable probe having a sensor for the physiological parameter and a transmitter for transmitting data to an external receiver. The probe may be used for monitoring any of various physiological parameters, including pH, temperature, and pressure, within the esophagus or other body lumens. Methods and deployment catheters are also disclosed, including a method for attaching a device to a tissue surface inside of a patient. The method comprises providing a device having a housing, a concavity on the housing, and a pin which is axially movable from a retracted position within the housing to an extended position which extends at least part way across the concavity. The device is carried on an introduction instrument into the body, and positioned at an attachment site, such that the concavity is adjacent the tissue surface at the attachment site. Tissue is drawn into the concavity, and the pin is advanced through the tissue to retain the device at the attachment site.

US Patent Application Publication 2005/0203500 to Saadat, which is incorporated herein by reference, describes techniques for mapping out endoluminal gastrointestinal surgery, including endoluminal gastric reduction. Mapping is achieved by locally marking the interior of the gastrointestinal lumen at specified locations.

US Patent Application Publication 2005/0075654 to Kelleher, which is incorporated herein by reference, describes techniques for soft tissue securement, and, in particular, tissue anchoring elements and deployment thereof. Such tissue anchoring elements may comprise a linkage element and an array of spreading elements. Endoscopic devices and methods are disclosed for deploying multiple anchoring elements to multiple sites and manipulating at least some of the associated linkage elements to approximate selected sites. Applications of such endoscopic devices and methods may include endoluminal therapy such as gastroplasty, which may be used for the treatment of obesity and gastroesophageal disease. Such devices and methods may also include the attachment of a foreign body to a tissue mass. Further aspects of the invention include devices and methods for the modification of mechanical properties of the anchoring sites so as to decrease the likelihood that anchoring elements will pull out. Such modification may include irritating or injuring the tissue within the anchoring sites, thereby causing a healing or scarification response, or may alternatively include deploying a solidifying agent within the anchoring sites.

US Patent Application Publication 2004/0193184 to Laufer et al., which is incorporated herein by reference, describes techniques for reconfiguring a tissue within a hollow body organ using an entirely endoscopic approach in order to effectively reduce flow of fluid contents into a second hollow body organ in fluid communication with the first.

U.S. Pat. No. 5,423,872 to Cigaina, which is incorporated herein by reference, describes a method for treating obesity and syndromes related to motor disorders of the stomach of a patient. The methods consists of artificially altering, by means of sequential electrical pulses and for preset periods of time, the natural gastric motility of the patient to prevent emptying or to slow down gastric transit. The '872 patent also describes a device including an electrical stimulator which is appropriately located subcutaneously in the abdominal wall, is anchored to the fascia of the musculus rectus abdominis, and is connected to the distal gastric antrum by means of an electrocatheter the terminal portion thereof of which is provided with metallic micro-barbs, for example two, which are angled so as to allow application of the tip of the catheter and prevent its extraction.

U.S. Pat. No. 5,837,006 to Ocel et al., which is incorporated herein by reference, describes an endocardial, active fixation, screw-in lead of the type having a fixation helix adapted to be rotated in a first, advancement direction out of an electrode head chamber and into cardiac tissue by rotation of a lead connector end and attached lead conductor with respect to an insulating sheath in the first direction and retracted into the chamber by rotation of the lead connector in the opposite, retraction direction. The lead includes a retraction stop mechanism for preventing over rotation of the helix in the retraction direction. The rotational motion of the lead conductor is transmitted to the helix by a connecting assembly and is translated into axial advancement and retraction of the helix by a guide cooperating with the helix turns. A retraction stop mechanism stops rotation of the helix in the retraction direction upon full retraction of the helix into the chamber and allows rotation of helix in the advancement direction. The retraction stop mechanism includes a fixed stop formed of a plurality of fixed cam and axial stop surfaces surrounding a proximal end bore of the chamber through which the lead conductor passes and a movable stop formed in the connecting mechanism of a like plurality of rotatable cam and axial stop surfaces aligned to face the fixed cam and axial stop surfaces adapted to engage in a locked relation of the stop surfaces upon full retraction of the fixation device into the chamber.

The following patents and patent application publications, all of which are incorporated herein by reference, may be of interest:

U.S. Pat. No. 6,918,871 to Schulze
U.S. Pat. No. 5,247,938 to Silverstein et al.
U.S. Pat. No. 6,754,536 to Swoyer et al.
U.S. Pat. No. 6,876,885 to Swoyer et al.
U.S. Pat. No. 6,745,079 to King
U.S. Pat. No. 6,852,110 to Roy et al.
U.S. Pat. No. 3,737,579 to Bolduc
U.S. Pat. No. 4,010,758 to Rockland et al.
U.S. Pat. No. 4,235,246 to Weiss
U.S. Pat. No. 4,452,254 to Goldberg et al.
U.S. Pat. No. 4,000,745 to Goldberg et al.
U.S. Pat. No. 4,357,946 to Dutcher et al.
U.S. Pat. No. 4,313,448 to Stokes
U.S. Pat. No. 4,177,818 to De Pedro
U.S. Pat. No. 6,510,332 to Greenstein
U.S. Pat. No. 6,321,124 to Cigaina
U.S. Pat. No. 6,477,423 to Jenkins
US Patent Application Publication 2005/0183732 to Edwards
US Patent Application Publication 2005/0107829 to Edwards et al.
US Patent Application Publication 2003/0220678 to Tronnes et al.
US Patent Application Publication 2004/0088023 to Imran et al.
US Patent Application Publication 2005/0065505 to Ryan
PCT Publication WO 04/069330 to Knudson et al.
PCT Publication WO 04/096337 to De Winter
PCT Publication WO 03/020365 to Swoyer et al.
European Patent Application Publication EP 1 447 052 A2
Japanese Patent Application Publication JP 2003/319945 to Schulze et al.

Swain et al., in "An endoscopically deliverable tissue-transfixing device for securing biosensors in the gastrointestinal tract", Gastrointestinal Endoscopy 40(6): 730-734 (1994), which is incorporated herein by reference, describe an attachment mechanism that uses suction to draw a fold of the stomach wall together, and inserts a preformed, Nylon, H-shaped tag through the fold of the stomach wall.

Wagh M S et al., in "Endoscopic transgastric abdominal exploration and organ resection: initial experience in a porcine model," Clin Gastroenterol Hepatol 3(9):892-6 (2005), which is incorporated herein by reference, describe a study which assessed the ability to systematically identify abdominopelvic organs using an endoscope via a per-oral transgastric route. A gastroscope was used to place a sterile over-tube into the esophagus of pigs. After antibacterial lavage, the gastric wall was incised, and a sterile dual-channel endoscope was advanced into the peritoneal cavity. Endoscopic abdominal exploration was performed, and the gastric incision was closed with endoclips.

The Following References, Which are Incorporated Herein by Reference, may be of Interest:

Kalloo A N et al. (2004) Flexible transgastric peritoneoscopy: a novel approach to diagnostic and therapeutic interventions. Gastrointest Endosc 60: 114-117.

Park P O et al. (2005) Experimental studies of transgastric gall bladder surgery: cholecystectomy and cholecystogastric anastomosis. Gastrointest Endosc 61: 601-606.

Kantsevoy S V et al. (2006) Transgastric endoscopic splenectomy: Is it possible? Surg Endosc 20:522-526.

Rattner D, Kalloo A, et al. (2006) White Paper: ASGE/SAGES Working Group on Natural Orifice Transluminal Endoscopic Surgery. Surg Endosc 20:329-333.

SUMMARY OF THE INVENTION

In embodiments of the present invention, tools and minimally-invasive surgical methods are provided for implanting electrode assemblies in a gastric wall of a subject. An implantation tool is advanced to a surface of the stomach, using either a combined endoscopic and transabdominal approach, or a per-oral endoluminal transgastric approach. Using the tool, an electrode assembly is implanted in the gastric wall, typically into a submucosal layer thereof, or, alternatively, into muscularis thereof. Typically, the tool is repositioned, and at least a second electrode is implanted at a second site of the gastric wall. Particular embodiments are described herein for implementing these techniques.

There is therefore provided, in accordance with an embodiment of the present invention, apparatus, including:

an electrode; and an implantation tool configured to be passed into an abdominal cavity of a patient, and to insert the electrode into a gastric wall of the patient, generally in parallel to the gastric wall.

In an embodiment, the implantation tool is configured to insert a length of the electrode that is at least 1 cm into the gastric wall, generally in parallel to the gastric wall.

In an embodiment, the implantation tool is configured to insert a length of the electrode that is at least 1.5 cm into the gastric wall, generally in parallel to the gastric wall.

In an embodiment, the implantation tool is configured to move the electrode in a proximal direction, with respect to the implantation tool, to place the electrode into the gastric wall.

In an embodiment, the implantation tool includes:

a securing device, which is configured to secure the implantation tool to a portion of the gastric wall; and an element which is configured to puncture and move through the portion of the gastric wall, and draw the electrode proximally through the portion of the gastric wall.

In an embodiment, the implantation tool includes:

a securing device, which is configured to secure the implantation tool to a portion of the gastric wall; and an element which is configured to puncture and move distally through the portion of the gastric wall, and subsequently draw the electrode proximally through the portion of the gastric wall.

In an embodiment, the securing device includes a suction applicator.

In an embodiment, the securing device includes first and second articulating pieces, the first piece configured to engage an inner surface of the gastric wall, and the second piece configured to engage an outer surface of the gastric wall.

In an embodiment, the implantation tool includes a screw having a distal tip configured for penetrating the gastric wall generally parallel to the gastric wall, and the electrode is wrapped around the screw.

In an embodiment, the electrode is wrapped around the screw in such a manner that it remains wrapped around the screw during screwing of the screw into the gastric wall, and remains in the gastric wall during unscrewing of the screw from the gastric wall.

In an embodiment, a distal portion of the electrode is looped around a distal portion of the screw, between the distal tip and threading of the screw, in a manner that maintains the wire wrapped around the screw during screwing of the screw into the gastric wall.

In an embodiment, the implantation tool includes:

a longitudinal element shaped to define a sharp distal tip that is configured to puncture the gastric wall; and a hooking assembly releasably coupled to the longitudinal element and coupled distally to the electrode, such that distal movement of the hooking assembly pulls the electrode in a distal direction.

In an embodiment, the hooking assembly is coupled to the longitudinal element in such a manner that proximal motion of the longitudinal element following insertion of the electrode into the gastric wall decouples the hooking assembly from the longitudinal element.

In an embodiment, the apparatus includes a stylet coupled to the longitudinal element, a distal tip of the stylet being proximal to the distal tip of the longitudinal element, and the hooking assembly is wrapped around the distal tip of the stylet.

In an embodiment, the apparatus includes a stylet coupled to the longitudinal element, a distal tip of the stylet being proximal to the distal tip of the longitudinal element, and the hooking assembly is shaped to define a loop, through which the distal tip of the stylet passes.

In an embodiment, the apparatus includes a stylet coupled to the longitudinal element, a distal tip of the stylet being proximal to the distal tip of the longitudinal element, and a cup-shaped portion of the hooking assembly engages the distal tip of the stylet.

In an embodiment, the longitudinal element includes a needle shaped to define a lateral opening, and the hooking assembly is configured to pass through the lateral opening following decoupling of the hooking assembly from the longitudinal element.

In an embodiment, the implantation tool includes a longitudinal element shaped to define a sharp distal tip that is configured to puncture the gastric wall, a distal portion of the electrode is parallel to a distal portion of the longitudinal element, the electrode is coupled to the implantation tool such that distal advancement of the implantation tool in the gastric wall advances the electrode in the gastric wall, and the implantation tool is configured to permit decoupling of the electrode from the implantation tool following implantation of the electrode in the gastric wall.

In an embodiment, the longitudinal element includes a rod.

In an embodiment, a proximal portion of the longitudinal element is shaped to define a bore, and a distal portion of the longitudinal element, proximal to the sharp distal tip, is not shaped to define a bore.

In an embodiment, a distal portion of the longitudinal element, proximal to the sharp distal tip, is shaped to define an arc when viewed in axial cross-section.

In an embodiment, the arc defines an angle between 250 and 290 degrees.

In an embodiment, the arc defines an angle greater than 180 degrees.

In an embodiment, the arc defines an angle less than 180 degrees.

In an embodiment, the distal portion of the electrode is disposed within the arc defined by the distal portion of the longitudinal element.

In an embodiment, the implantation tool includes a pushing element, configured to decouple the electrode from the longitudinal element by applying a pushing force to the electrode during proximal motion of the longitudinal element.

In an embodiment, the implantation tool includes one or more coupling rings, coupled to the distal portion of the longitudinal element, and the distal portion of the electrode is slidably coupled within the one or more coupling rings.

In an embodiment, the one or more coupling rings inhibit decoupling of the distal portion of the longitudinal element from the distal portion of the electrode due to relative lateral motion of the longitudinal element with respect to the electrode, but permit decoupling of the distal portion of the longitudinal element from the distal portion of the electrode due to relative axial motion of the longitudinal element with respect to the electrode.

In an embodiment, the implantation tool is configured to be secured to the gastric wall to facilitate the insertion of the electrode.

In an embodiment, the implantation tool includes a securing device, the securing device including first and second articulating pieces, the first piece configured to engage an inner surface of the gastric wall, and the second piece configured to engage an outer surface of the gastric wall.

In an embodiment, the first piece is configured to be inserted through the gastric wall from the abdominal cavity.

In an embodiment, the securing device is shaped to define a channel for passage of the electrode therethrough and thereby guide the electrode into the gastric wall.

In an embodiment, the apparatus includes a suction source, configured to hold the implantation tool in a desired orientation with respect to the gastric wall.

In an embodiment, the suction source is configured to maintain an alignment of the implantation tool with the gastric wall prior to and during insertion of the electrode into the gastric wall.

In an embodiment, the electrode includes two electrodes, and the implantation tool is configured to implant the electrodes in the gastric wall, without removing the implantation tool from a body of the patient between successive electrode implantations.

In an embodiment, the apparatus includes a cartridge, within which are disposed the two electrodes.

In an embodiment, the cartridge is generally cylindrical in shape, and the two electrodes are separated by 150-180 degrees with respect to an axis of the cartridge.

In an embodiment, the cartridge is configured to be rotated, following implantation of a first one of the electrodes, to facilitate implantation of a second one of the electrodes.

In an embodiment, the cartridge is configured to be secured to a site of implantation of the first electrode to facilitate the implantation of the first electrode and during rotation of the cartridge, and to subsequently be secured to a site of implantation of the second electrode to facilitate the implantation of the second electrode.

In an embodiment, the apparatus includes a source of suction, to secure the cartridge to the site of implantation of the first electrode.

In an embodiment, the apparatus includes a securing device, configured to secure the cartridge to the gastric wall by squeezing an inner surface and an outer surface of the gastric wall at the site of implantation of the first electrode.

There is further provided, in accordance with an embodiment of the present invention apparatus, including:
 a conductive metal tube;
 an electrode wire, coupled to an external surface of the tube and configured for implantation in contact with tissue of a subject;
 a conductor, coupled to the external surface of the tube; and
 a shaft, slidably coupled within the tube.

In an embodiment, the wire and conductor are crimped to the external surface.

In an embodiment, the wire and conductor are welded to the external surface.

In an embodiment, the electrode is configured for implantation within a gastric wall of a subject.

There is additionally provided, in accordance with an embodiment of the present invention, a method, including:
 introducing an endoscope via a mouth of a patient into a stomach of the patient;
 forming a hole in a wall of the stomach;
 pushing the endoscope through the hole;
 securing a portion of the endoscope to the gastric wall; and
 mechanically facilitated by the securing, performing a procedure while the portion of the endoscope is secured to the gastric wall.

In an embodiment, securing includes securing to the gastric wall a portion of the endoscope that is inside the stomach.

In an embodiment, securing includes securing to the gastric wall a portion of the endoscope that is outside the stomach.

In an embodiment, forming the hole includes dilating the hole by inflating a balloon to facilitate passage of the endoscope through the hole.

In an embodiment, securing the portion includes securing a portion of the gastric wall selected from the group consisting of: an exterior of a greater curve of the stomach, an exterior of an anterior wall of the stomach, and an exterior wall of the stomach on or in a vicinity of a lesser curvature of the stomach.

In an embodiment, introducing the endoscope includes:
 making a distal segment of the endoscope curve while it is in the stomach; and
 guiding the portion of the endoscope towards a location at an anterior wall near a greater curvature of the stomach.

In an embodiment, forming the hole includes forming the hole with a tool, and including discarding the tool after forming the hole.

In an embodiment, performing the procedure includes screwing a screw into the gastric wall generally in parallel to the wall.

In an embodiment, by screwing the screw, an electrode wrapped around threads of the screw is implanted in the wall, and performing the procedure includes subsequently unscrewing the screw from the gastric wall and leaving the electrode in the wall.

In an embodiment, performing the procedure includes advancing a strip within a layer of the stomach.

In an embodiment, the layer includes a submucosal layer of the stomach, and advancing the strip includes advancing the strip within the submucosal layer.

In an embodiment, advancing the strip includes causing bending of the strip with respect to a first of three axes of the strip, while substantially not causing bending of the strip with respect to the other two axes of the strip.

In an embodiment, causing the bending includes causing the bending during advancement of the strip around a less curvature of an antrum of the stomach.

In an embodiment, advancing the strip includes advancing the strip while it is within a sheath.

In an embodiment, performing the procedure includes retracting the strip from the sheath after advancing the sheath, and leaving the sheath in the layer of the stomach.

In an embodiment, performing the procedure includes advancing an electrode in the sheath, after retracting the strip.

In an embodiment, advancing the electrode includes advancing at least two electrodes in the sheath.

In an embodiment, securing the portion includes:
securing the portion with a securing device;
passing a guide through the gastric wall; and
coupling the guide to the securing device,
and performing the procedure includes utilizing the coupling of the guide to the securing device to facilitate placement of an electrode in the gastric wall.

In an embodiment, coupling the guide to the securing device includes inserting the guide into the securing device.

In an embodiment, securing the portion with the securing device includes applying suction by the securing device to hold a portion of the securing device against the gastric wall.

In an embodiment, securing the portion with the securing device is performed when the securing device is inside the stomach.

In an embodiment, securing the portion with the securing device is performed when the securing device is outside of the stomach.

In an embodiment, passing the guide through the gastric wall includes passing the guide from within the stomach to outside of the stomach.

In an embodiment, passing the guide through the gastric wall includes passing the guide from outside of the stomach to inside the stomach.

In an embodiment, the guide includes a guide needle, and passing the guide includes passing the guide needle.

In an embodiment, passing the guide through the gastric wall is performed before coupling the guide to the securing device.

In an embodiment, passing the guide through the gastric wall is performed after coupling the guide to the securing device.

In an embodiment, performing the procedure includes inserting a distal tip of a needle into a plurality of layers of the stomach, and identifying when the distal tip of the needle has reached a specified layer.

In an embodiment, the specified layer includes a submucosal layer of the stomach, and performing the procedure includes applying pressure to a liquid in the needle, and identifying includes identifying a pressure drop in the liquid due to the liquid being expelled into the submucosal layer.

In an embodiment, performing the procedure includes inserting an electrode into the specified layer subsequently to the identifying.

In an embodiment, pushing the endoscope includes guiding a distal tip of the endoscope to initially move away from the stomach after passing through the hole, and subsequently turn towards the stomach and move towards the stomach, and securing the portion includes securing the portion after the moving of the distal portion towards the stomach.

In an embodiment, guiding the distal tip includes orienting a longitudinal axis of the endoscope at the distal tip to be generally parallel to the gastric wall at a site of contact between the portion of the endoscope and the gastric wall.

In an embodiment, securing the portion includes securing the portion to the gastric wall by suction.

In an embodiment, performing the procedure includes inserting an electrode into the gastric wall generally parallel to a plane of the gastric wall.

In an embodiment, inserting the electrode includes inserting the electrode such that a length of at least 1 cm of the electrode remains within tissue of the gastric wall.

In an embodiment, securing the portion includes clamping the portion of the gastric wall between two securing members.

In an embodiment, at least one of the securing members is magnetic, and clamping the portion includes clamping the portion of the gastric wall using magnetic attraction between the securing members.

In an embodiment, clamping the portion includes clamping the portion of the gastric wall without using magnetic attraction between the securing members.

In an embodiment, clamping the portion of the stomach includes placing at least some of the gastric wall in tension.

In an embodiment, the two securing members articulate at a hinge, and clamping includes reducing an angle between the two securing members with respect to the hinge.

In an embodiment, the method includes inserting an electrode into tissue of the gastric wall, via at least one of the securing members.

In an embodiment, the method includes facilitating the clamping by advancing one of the securing members through the wall of the stomach.

In an embodiment, performing the procedure includes performing the procedure at least a first and a second time, and clamping the gastric wall at first and second sites of the gastric wall at the first and second times, respectively.

In an embodiment,
the endoscope includes a baby scope and a mother scope,
pushing the endoscope through the hole includes pushing the mother scope through the hole while the baby scope remains in the stomach, and
the method includes visualizing by at least the baby scope during the procedure.

In an embodiment, the method includes visualizing by the mother scope while the mother scope is outside of the stomach.

In an embodiment, visualizing by at least the baby scope includes visually confirming that the gastric wall is not unintentionally perforated during the procedure.

In an embodiment, the method includes stabilizing the baby scope during the procedure.

In an embodiment, stabilizing includes stabilizing the baby scope with an inflated balloon.

In an embodiment, securing includes applying suction to the gastric wall.

In an embodiment, applying suction includes applying suction from within the stomach.

In an embodiment, applying suction includes applying suction from outside of the stomach.

In an embodiment, performing the procedure includes performing the procedure at least a first and a second time, and applying suction to first and second sites of the gastric wall at the first and second times, respectively.

In an embodiment, forming the hole includes cutting tissue of the wall.

In an embodiment, the endoscope includes a working channel, and cutting includes (a) cutting using a surgical cutting device that is guided through the working channel of the endoscope, and (b) subsequently withdrawing the cutting device from the working channel.

In an embodiment, cutting includes cutting with a device selected from the group consisting of a scalpel, a harmonic scalpel, a laser, a CO2 laser, an ultrasound device, a diathermy device, an RF device, a sphincterotome, and an RF needle.

In an embodiment, cutting includes cutting tissue of an anterior wall of the stomach.

In an embodiment, the method includes closing the hole.

In an embodiment, closing the hole includes suturing the hole closed.

In an embodiment, closing the hole includes clipping the hole closed.

In an embodiment, closing the hole includes applying a biocompatible adhesive to the hole.

In an embodiment, closing the hole includes closing the hole with a tool, and the method includes discarding the tool after having closed only a single gastric wall hole using the tool.

In an embodiment, closing the hole includes stapling the hole.

In an embodiment, stapling includes stapling with a linear stapler.

In an embodiment, stapling includes stapling with a dedicated endoscopic stapling device.

In an embodiment, the method includes discarding the stapling device after having closed only a single gastric wall hole using the stapling device.

In an embodiment, performing the procedure includes implanting an electrode in the wall of the stomach.

In an embodiment, implanting includes inserting the electrode generally parallel to a plane of the wall of the stomach.

In an embodiment, the method includes magnetically stabilizing the electrode with respect to the endoscope at least prior to implanting the electrode in the wall of the stomach.

In an embodiment, implanting includes:
  implanting the electrode from a position outside of the stomach; and
  decoupling a lead of the electrode from the endoscope, such that the lead remains in the abdominal cavity.

In an embodiment, performing the procedure includes transabdominally accessing the lead to facilitate coupling of the lead to a control unit.

In an embodiment, transabdominally accessing the lead includes hooking the lead using a transabdominal approach, and pulling the lead in a superficial direction.

In an embodiment, implanting the electrode includes implanting in tissue of the wall of the stomach a length of the electrode that is at least three times a thickness of the wall at a site of implantation of the electrode.

In an embodiment, implanting in the tissue of the wall includes implanting a length of the electrode that is at least five times the thickness of the wall at the site of implantation.

In an embodiment, implanting in the tissue of the wall includes implanting a length of the electrode that is at least ten times the thickness of the wall at the site of implantation.

In an embodiment, implanting the electrode includes implanting a plurality of electrodes.

In an embodiment, implanting the plurality of electrodes includes implanting at least two of the electrodes without withdrawing the portion of the endoscope into the stomach between the implanting of a first one of the at least two electrodes and a second one of the at least two electrodes.

In an embodiment, the method includes rolling the portion of the endoscope between the implanting of a first one of the electrodes and the implanting of a second one of the electrodes.

In an embodiment, rolling includes rolling at least 90 degrees.

In an embodiment, rolling includes rolling at least 120 degrees.

In an embodiment, rolling includes rolling between 150 and 180 degrees.

There is yet additionally provided, in accordance with an embodiment of the present invention, a method, including:
  orienting an electrode to be generally parallel with a gastric wall of a stomach; and
  implanting in the gastric wall a length of the electrode that is at least three times a local thickness of the gastric wall such that following implantation, the length of electrode is generally parallel with the gastric wall.

In an embodiment, implanting includes inserting into the gastric wall a length of the electrode that is at least five times a local thickness of the gastric wall.

In an embodiment, implanting includes inserting into the gastric wall a length of the electrode that is at least ten times a local thickness of the gastric wall.

In an embodiment, implanting includes placing the length of the electrode substantially entirely within a single layer of the stomach.

There is still yet additionally provided, in accordance with an embodiment of the present invention, a method, including:
  orienting an axis of a helical electrode to be generally parallel with a gastric wall of a stomach; and
  screwing the helical electrode into the gastric wall, such that the axis of the helical electrode is generally parallel with the gastric wall.

In an embodiment, screwing the helical electrode includes screwing a screw around which the electrode is wrapped.

In an embodiment, the method includes unscrewing the screw to leave the electrode in the gastric wall.

There is further yet additionally provided, in accordance with an embodiment of the present invention, a method, including:
  orienting an electrode device including an electrode coupled to a distal anchor, to be generally parallel with a gastric wall of a stomach; and
  advancing the distal anchor and the electrode through an external surface of the gastric wall, and then advancing the distal anchor out of the external surface of the gastric wall, such that the electrode remains in and generally parallel with the gastric wall, and the anchor inhibits proximal withdrawing of the electrode.

There is also provided, in accordance with an embodiment of the present invention, a method, including:
  placing a helical electrode against an outer surface of a gastric wall, such that a longitudinal axis of the helical electrode is generally parallel to the wall; and
  rotating the electrode a plurality of times, such that on each rotation a distal tip of the electrode is inserted into and removed from the gastric wall.

In an embodiment, the method includes limiting a depth of insertion of the electrode into the gastric wall by placing a stylet within the helical electrode.

The present invention will be more fully understood from the following detailed description of embodiments thereof, taken together with the drawings, in which:

BRIEF DESCRIPTION OF THE DRAWINGS

FIGS. 2A-B are flow charts that schematically illustrate a method for implanting electrodes in the gastric wall using a combined endoscopic and transabdominal approach, in accordance with an embodiment of the present invention;

FIG. 5 is a schematic illustration of a transabdominal implantation tool, in accordance with an embodiment of the present invention;

FIG. 6 is a schematic illustration of a submucosal needle, in accordance with an embodiment of the present invention;

FIG. 7 is another view of the transabdominal implantation tool of FIG. 5, in accordance with an embodiment of the present invention;

FIGS. 8A-B are schematic illustrations of a coupling of the needle-guide cap of FIG. 4 and a guide needle of the implantation tool of FIG. 5 through the gastric wall, in accordance with an embodiment of the present invention;

FIGS. 9A and 9B are schematic cross-sectional and three-dimensional views, respectively, of the coupling of the needle-guide cap of FIG. 4 and the guide needle of the implantation tool of FIG. 5 through the gastric wall, in accordance with an embodiment of the present invention;

FIG. 10 is a schematic illustration of a flexible strip inserted into a sheath placed around the submucosal needle of FIG. 6, in accordance with an embodiment of the present invention;

FIGS. 13A-C are schematic illustrations of a transabdominal implantation tool, in accordance with an embodiment of the present invention;

FIG. 17 is a schematic illustration of an electrode assembly implantation endoscope, in accordance with an embodiment of the present invention;

FIG. 20 is a schematic illustration of a non-coaxial tine-coupling electrode device, in accordance with an embodiment of the present invention;

FIG. 21 is a schematic cross-sectional illustration of a coupling of a wire of an electrode assembly of the electrode device of FIG. 10 to a conductor, in accordance with an embodiment of the present invention;

FIG. 22 is a schematic illustration of the electrode device of FIG. 20 during an electrode implantation procedure, in accordance with an embodiment of the present invention;

FIGS. 23A-B are schematic illustrations of alternative configurations of a hook of a hooking assembly of the electrode assembly of the electrode device of FIG. 10, in accordance with respective embodiments of the present invention;

FIG. 24 is a schematic illustration of a non-coaxial rod-guided electrode device, in accordance with an embodiment of the present invention;

FIG. 25 is a schematic cross-sectional illustration of a distal portion of a rod of the electrode device of FIG. 24, in accordance with an embodiment of the present invention;

FIG. 28 is a schematic illustration of a non-coaxial screw-fixated electrode device, in accordance with an embodiment of the present invention;

FIG. 29 is a schematic cross-sectional illustration of a double-crimp tube of the electrode device of FIG. 28, in accordance with an embodiment of the present invention;

FIG. 30 is a schematic illustration of a coaxial screw-driven electrode device, in accordance with an embodiment of the present invention;

FIG. 31 is a schematic illustration of a coaxial screw-fixated electrode device, in accordance with an embodiment of the present invention;

FIGS. 34-36 are schematic illustrations of a T-anchor electrode device, in accordance with an embodiment of the present invention;

FIG. 37 is a schematic cross-sectional illustration of a rod of an implantation tool of the electrode device of FIGS. 34-36, in accordance with an embodiment of the present invention;

FIG. 38 is a schematic illustration of a stylet-guided corkscrew electrode device, in accordance with an embodiment of the present invention;

DETAILED DESCRIPTION OF EMBODIMENTS

Embodiments of the present invention include (a) minimally-invasive surgical methods for implanting electrode assemblies in a gastric wall of a subject, and (b) electrode assemblies for implantation in the gastric wall. The surgical methods include a combined endoscopic and transabdominal approach, and an endoluminal transgastric approach. These surgical methods, and their associated implantation tools, are useful for implanting the novel electrode assemblies described herein, or electrode assemblies known in the art.

Surgical Methods and Tools
Combined Endoscopic and Transabdominal Approach

Figure 1:
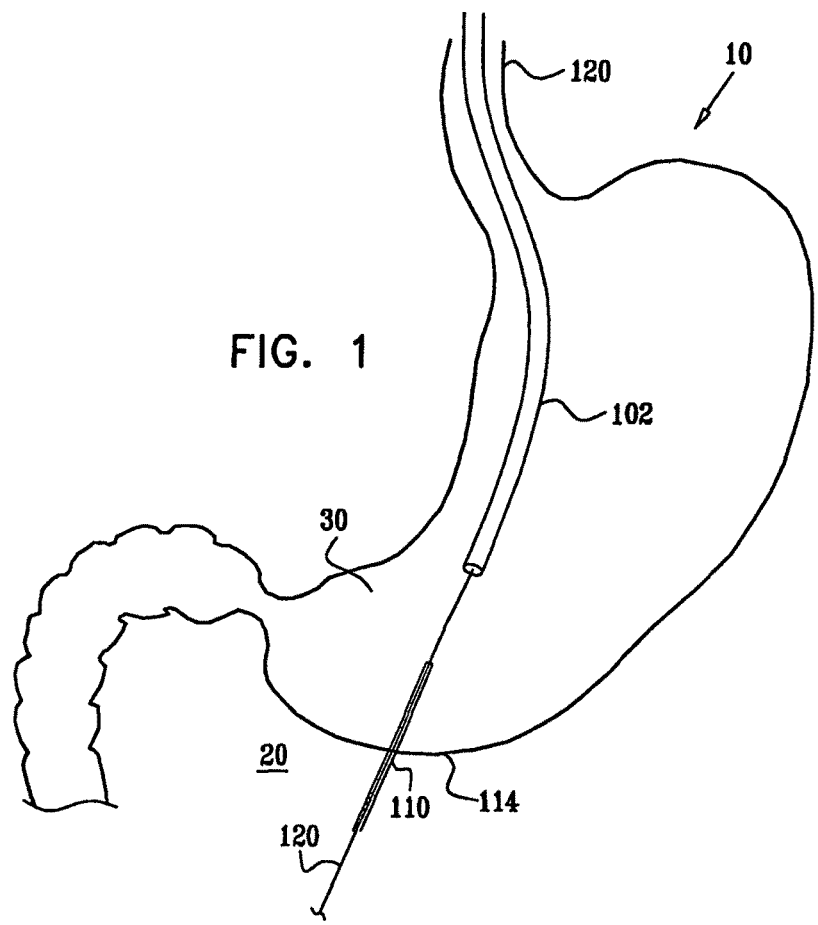
FIG. 1 is a schematic illustration of a stomach upon which is performed a minimally-invasive procedure using a combined endoscopic and transabdominal approach for implanting electrodes in a gastric wall, in accordance with an embodiment of the present invention.

FIG. 1 is a schematic illustration of a stomach 10 in an abdominal cavity 20, upon which is performed a minimally-invasive procedure using a combined endoscopic and transabdominal approach for implanting electrodes in a gastric wall 30, in accordance with an embodiment of the present invention. The procedure is typically performed while the patient is under sedation, rather than under general anesthesia. Insufflation of abdominal cavity 20 is typically not necessary. (Some embodiments described herein may be performed with insufflation.)

FIGS. 2A-B are flow charts that schematically illustrate a method for implanting electrodes in gastric wall 30 using a combined endoscopic and transabdominal approach, in accordance with an embodiment of the present invention. FIG. 2A illustrates a preparatory positioning stage of the method, and FIG. 2B illustrates an implantation stage of the method. At an endoscope introduction step 100 of the preparatory positioning stage (FIG. 2A), an endoscope 102 (FIG. 1) is introduced into stomach 10 via the mouth. A distal end of the endoscope comprises a light source, a tube connected to an external source of pressure, and, optionally, an image sensor. Using gas provided via the tube, stomach 10 is insufflated, at an insufflation step 104.

At an illumination step 106, the light source at the distal end of the endoscope is illuminated at an intensity great enough to be visible from outside of the abdomen. A needle 110 (FIG. 1) is inserted from outside the body through abdominal cavity 20 toward the illuminated light source, at a needle insertion step 112. Typically, the needle is inserted at the right side of the abdomen below the ribs, approximately above an antrum 114 of stomach 10. The needle typically has an outer diameter (OD) of 14 gauge (about 3 mm). At a guidewire insertion step 116, a guidewire 120 is inserted from outside the body, through needle 110, and into stomach 10. The distal end of the guidewire is coupled to the distal end of endoscope 102, and the endoscope is retracted from the body via the mouth, pulling the distal end of the guidewire through the mouth.

Figure 3:
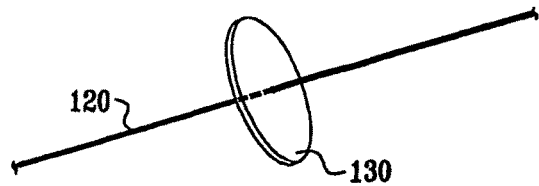
FIG. 3 is a schematic illustration of a flange, in accordance with an embodiment of the present invention.

Reference is made to FIG. 3, which is a schematic illustration of a flange 130, in accordance with an embodiment of the present invention. At a flange coupling step 132 of the method of FIG. 2A, flange 130 is coupled to guidewire 120. The guidewire is retracted transabdominally, pulling the flange through the mouth to the inner surface of the gastric wall. The guidewire is further pulled, such that flange 130 pulls the gastric wall towards the inner surface of abdomen 20, at a gastric wall pull step 134. While continuing to pull on the flange, a dilator is advanced over guidewire 120 via abdominal cavity 20, at a dilator advancement step 136. For example, the dilator may have an OD of 15 F (5 mm). At an over-tube advancement step 138, a stiff over-tube is advanced over the dilator, until the distal end of the over-tube reaches a vicinity of the outer surface of the gastric wall. For example, the over-tube may have an OD of 18 F (6 mm) The dilator is then withdrawn, at a dilator withdrawal step 140.

At a flange release step 142, the pulling force is released from flange 130, allowing the over-tube to follow the stomach as the stomach "falls" back towards the posterior side of abdominal cavity 20. The flange is withdrawn from the stomach by pulling the entire guidewire 120 through the mouth, at a flange withdrawal step 144.

The preparatory positioning stage of the method of FIGS. 2A-B has now been completed. The distal end of the stiff over-tube is now in a vicinity of the outer surface of the gastric wall. The steps of the implantation stage of the method, illustrated in FIG. 2B, are now performed.

Figure 4:
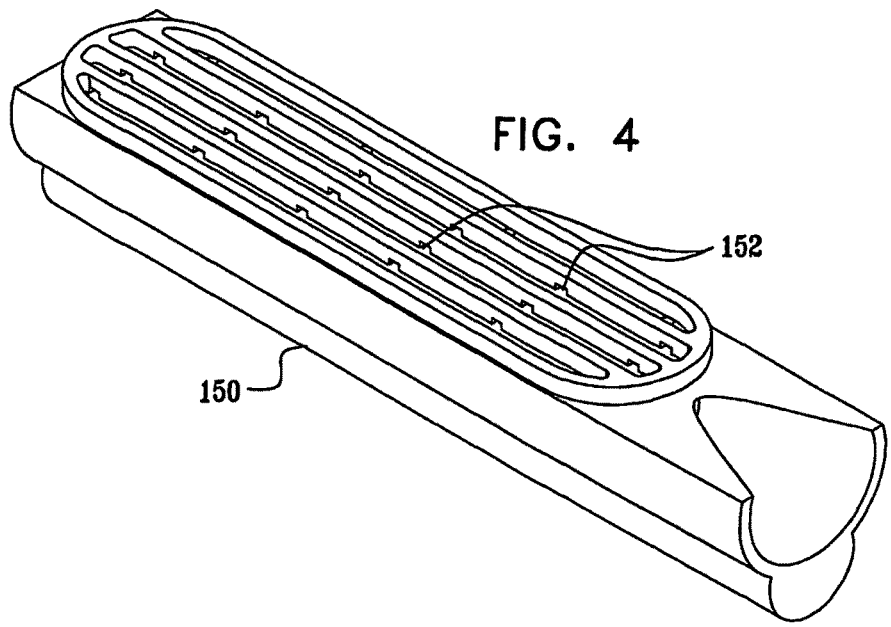
FIG. 4 is a schematic illustration of a needle-guide cap, in accordance with an embodiment of the present invention.

FIG. 4 is a schematic illustration of a needle-guide cap 150, in accordance with an embodiment of the present invention. Needle-guide cap 150 is adapted to be inserted into stomach 10 by endoscope 102, as described hereinbelow with reference to step 200 of the method of FIG. 2B. Needle-guide cap 150 comprises one or more suction vents 152, which are in fluid communication with a negative pressure source via a tube of endoscope 102 (for clarity of illustration, the tube is not shown in the figures).

FIG. 5 is a schematic illustration of a transabdominal implantation tool 170, in accordance with an embodiment of the present invention. Tool 170 comprises a mandrel 172, which typically is shaped so as to define (a) a submucosal guiding tube 174, (b) an imaging element tube 176, for passage therethrough of an imaging element and a light source (imaging element and light source not shown), and (c) and a guide needle tube 177. Submucosal guiding tube 174 is typically generally circular in cross-sectional shape, with two small protrusions 175 on opposite sides of the tube. Tool 170 comprises a guide needle 178, which passes through guide needle tube 177 of mandrel 172, and is adapted to be coupled to needle-guide cap 150, as described hereinbelow with reference to step 212 of the method of FIG. 2B. Guide needle 178 typically has a length of about 20 mm, and an OD of between about 0.8 and about 1.5 mm.

FIG. 6 is a schematic illustration of a submucosal needle 180, in accordance with an embodiment of the present invention. Submucosal needle 180 typically is circular in cross-section, and has an OD of between about 0.6 and about 1.5 mm. A sheath 182 is placed around a portion of needle 180. Typically, the sheath has a length of between about 30 and about 50 mm, and is placed around the needle such that the distal portion of the needle that protrudes from the sheath has a length of between about 2 and about 10 mm.

FIG. 7 is another view of transabdominal implantation tool 170, in accordance with an embodiment of the present invention. Prior to beginning the implantation procedure, submucosal needle 180 and sheath 182 are inserted into submucosal guiding tube 174, such that the tip of the submucosal needle remains in the guiding tube, as shown in FIG. 7. Submucosal needle 180 and guide needle 178 are generally parallel to one another.

At a needle-guide cap insertion step 200 of the method of FIG. 2B, needle-guide cap 150 is coupled to endoscope 102 and inserted into stomach 10 via the mouth (FIG. 1). At a tool advancement step 202, transabdominal implantation tool 170, including submucosal needle 180 and guide needle 178, is inserted into the stiff over-tube. As mentioned above with reference to step 138 of FIG. 2A, the distal end of the over-tube is in the vicinity of the outer surface of the gastric wall. Tool 170 is advanced through the over-tube until the tool reaches the outer surface of the gastric wall. The imaging element may be used to guide the positioning of the tool once it is in the vicinity of the gastric wall.

Reference is made to FIGS. 8A-B, which are schematic illustrations of a coupling of needle-guide cap 150 and guide needle 178 through gastric wall 30 of stomach 10, in accordance with an embodiment of the present invention. At a coupling step 212 of the method of FIG. 2B, guide needle 178 is inserted through gastric wall 30. Using endoscope 102 (and, typically, its image sensor), needle-guide cap 150 is brought into alignment with the guide needle. The guide needle is inserted into the needle-guide cap, thereby coupling transabdominal implantation tool 170 to needle-guide cap 150 across gastric wall 30, as shown in FIG. 8B.

Reference is made to FIGS. 9A and 9B, which are schematic cross-sectional and three-dimensional views, respectively, of the coupling of needle-guide cap 150 and guide needle 178 through gastric wall 30, in accordance with an embodiment of the present invention. (For clarity of illustration, the view in FIG. 9B does not include gastric wall 30.) In FIG. 9A, gastric wall 30 is shown including a serosal layer 214, muscularis 216, a submucosal layer 218, and a mucosal layer 220. At a suction application step 217 of the method of FIG. 2B, negative pressure is applied through suction vents 152 of needle-guide cap 150, thereby and/or in concert with rotating or aligning needle-guide cap 150 until it is stabilized, aligned with and in contact with a portion of an inner surface 222 of gastric wall 30 (i.e., the inner surface of mucosal layer 220 of gastric wall 30).

At a submucosal needle advancement step 230, submucosal needle 180 is advanced through the layers of gastric wall 30, while injecting (or attempting to inject) a biocompatible liquid, typically saline solution, into gastric wall 30 from the distal tip of submucosal needle 180. When the tip of submucosal needle 180 reaches submucosal layer 218 of the gastric wall, a pressure drop occurs, at which point the advancement is halted. The pressure drop occurs because it is easier to inject the liquid into submucosal layer 218 than into muscularis 216. A saline bubble has been created in submucosal layer 218. Submucosal needle 180 is withdrawn, leaving the distal end of sheath 182 in submucosal layer 218, at a needle withdrawal step 232.

Reference is made to FIG. 10, which is a schematic illustration of a flexible strip 240 inserted into sheath 182, in accordance with an embodiment of the present invention. For clarity of illustration, gastric wall 30 is not shown in the figure. At a strip insertion step 250 of the method of FIG. 2B, strip 240 is inserted into sheath 182, typically until a distal tip of the strip protrudes from the sheath into submucosal layer 218 of gastric wall 30.

In an embodiment, the thickness of strip 240 is up to about 1.5 mm (typically about 0.5-1 mm), and the width of strip 240 is about 2-5 mm (typically about 3 mm). The wall thickness of sheath 182 is about 0.05-1 mm (typically about 0.2-0.5 mm).

Figure 11A:
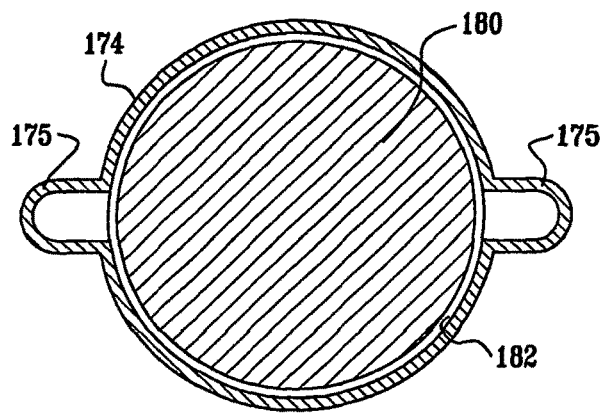
FIGS. 11A and 11B are schematic cross-sectional illustrations of the sheath of FIG. 10 and a submucosal guiding tube of the implantation tool of FIG. 5 during insertion of the submucosal needle of FIG. 6 and the strip of FIG. 10, respectively, in accordance with an embodiment of the present invention.
Figure 11B:
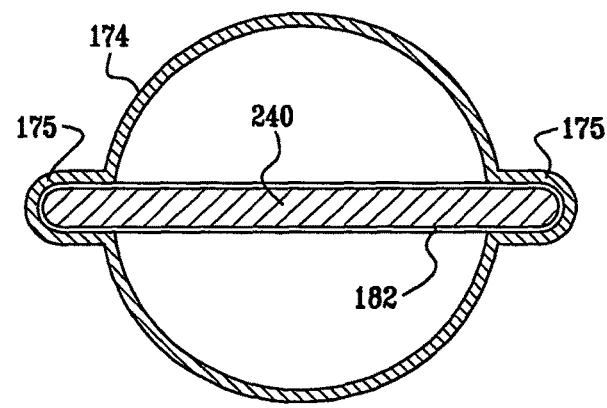

FIGS. 11A and 11B are schematic cross-sectional illustrations of sheath 182 and submucosal guiding tube 174 during insertion of submucosal needle 180 and strip 240, respectively, in accordance with an embodiment of the present invention. As can be seen in FIG. 11B, strip 240 is configured to advance through protrusions 175 of submucosal guiding tube 174, with sheath 182 fitting snugly around the strip. Protrusions 175 serve to align the flat sides of strip 240 with the section of gastric wall 30 into which sheath 182 has been inserted.

Figure 11C:
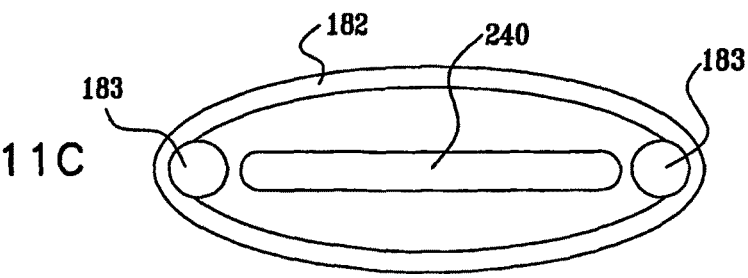
FIG. 11C is a schematic cross-sectional illustration of the sheath and strip of FIG. 10, in accordance with an embodiment of the present invention.

FIG. 11C is a schematic cross-sectional illustration of sheath 182 comprising, or coupled to, two channels 183, in accordance with an embodiment of the present invention. In this embodiment, electrodes are passed through the channels either prior to placement of sheath 182 in the patient's body, or after the sheath has been advanced to a desired location with respect to stomach 10 using techniques described with reference to FIG. 12. For some applications, the sheath remains in place chronically, in order to maintain the relative spacing of electrodes. Alternatively, the sheath is removed, and the electrodes maintain their relative spacing without such an external support.

Figure 12:
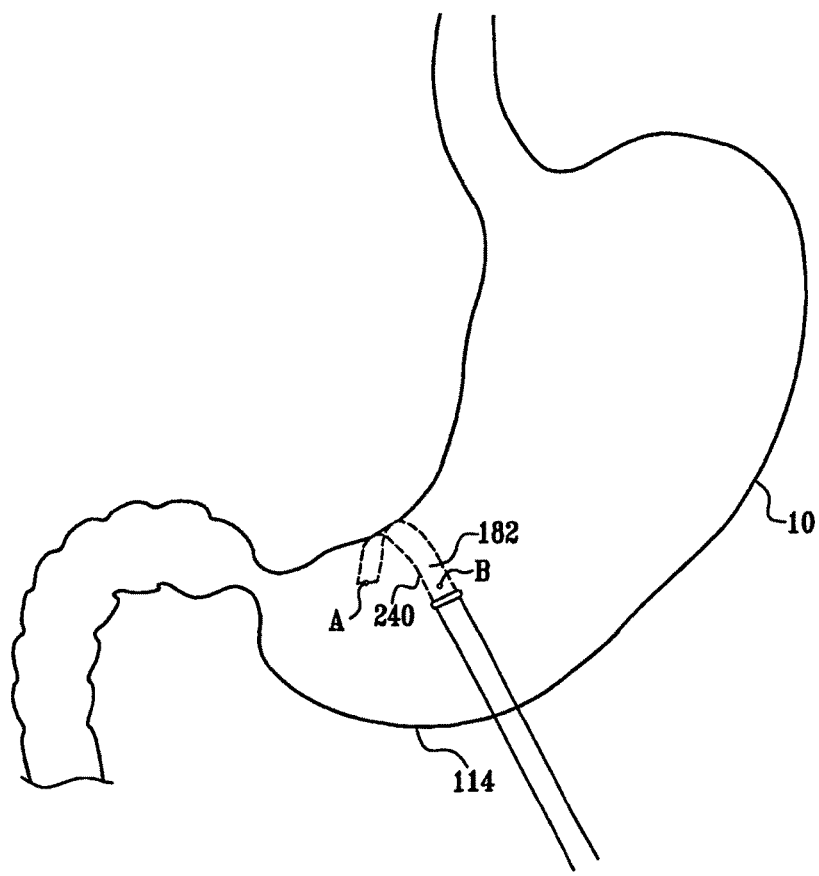
FIG. 12 is a schematic illustration of the advancement of the strip and sheath of FIG. 10 through a submucosal layer of the stomach, in accordance with an embodiment of the present invention.

FIG. 12 is a schematic illustration of the advancement of strip 240 and sheath 182 through submucosal layer 218 of stomach 10, in accordance with an embodiment of the present invention. At a submucosal advancement step 252 of the method of FIG. 2B, strip 240 and sheath 182 are advanced around a portion of stomach 10, typically around a lesser curvature of antrum 114, until the distal end of sheath 182 reaches the posterior antrum. In this manner, the strip and sheath are typically advanced between about 4 and about 10 cm, e.g., about 6 cm. Strip 240 is withdrawn, leaving sheath 182 in place in the submucosal layer, at a strip withdrawal step 254. Electrodes are advanced through sheath 182, and implanted in gastric wall 30 of stomach 210, at an electrode implantation step 256. Typically, a first set of one or more electrodes is implanted at the posterior antrum, as indicated by point "A" in FIG. 12, and a second set of one or more electrodes is implanted at the anterior antrum, as indicated by point "B". Alternatively, strip 240 and sheath 182 are advanced around a greater curvature of stomach 10 (configuration not shown). At a sheath removal step 258, sheath 182 is removed from the body, bringing the implantation procedure to a conclusion.

Reference is made to FIGS. 13A-C, which are schematic illustrations of a transabdominal implantation tool 300, in accordance with an embodiment of the present invention. In this embodiment, tool 300 is used instead of transabdominal implantation tool 170 for inserting submucosal needle 180 and sheath 182 into muscularis 216. Tool 300, while in the closed position shown in FIG. 13A, is laparoscopically advanced to an external surface of stomach 10.

Once at the external surface of the stomach, a puncturing element 302 is advanced distally over a base 304 of tool 300, such that a sharp distal tip 306 protrudes from the tool, as shown in FIG. 13B. Tip 306 is driven through gastric wall 30.

Once tip 306 has been driven through gastric wall 30, tool 300 is brought back into its initial closed position. Puncturing element 302 is positioned in the stomach, while base 304 is pressed against and substantially parallel to the outer surface of the stomach. Puncturing element 302 and base 304 are shaped so as to together define a channel 308. Submucosal needle 180 is introduced through the channel, and is advanced into muscularis 216. Submucosal needle 180 is withdrawn, and one or more electrodes are implanted in the muscularis, such as by using techniques described hereinabove with reference to steps 232-258 of the method of FIG. 2B.

Reference is again made to FIG. 13A. For some applications, tool 300 comprises a working channel 310. For example, a fiber optic cable or wires for a proximally-positioned imaging element may pass through the channel.

Figure 13D:
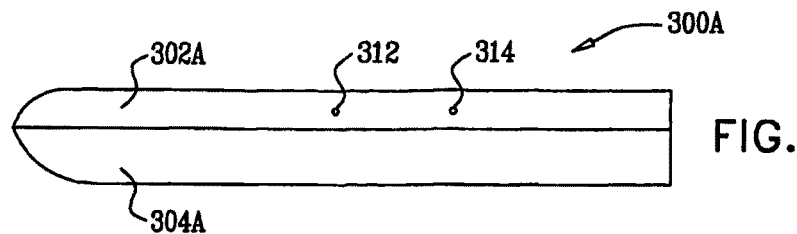
FIGS. 13D-G are schematic illustrations of a transabdominal implantation tool, in accordance with another embodiment of the present invention.
Figure 13E:
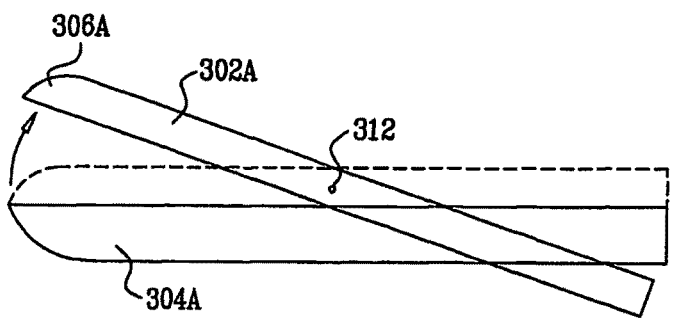
Figure 13F:
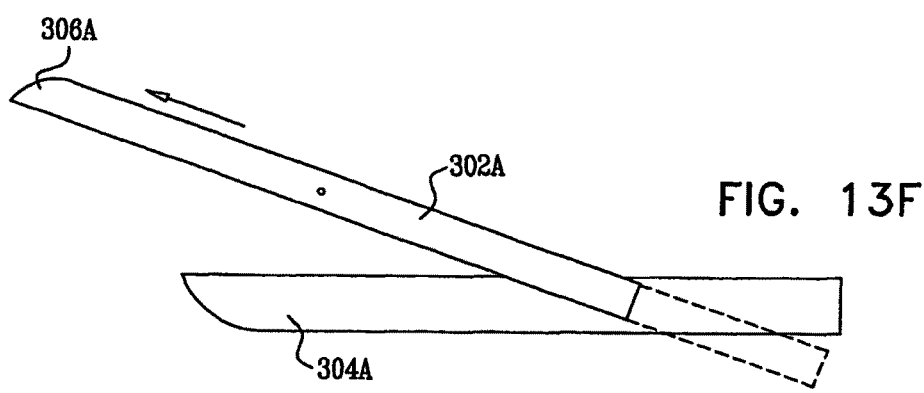
Figure 13G:
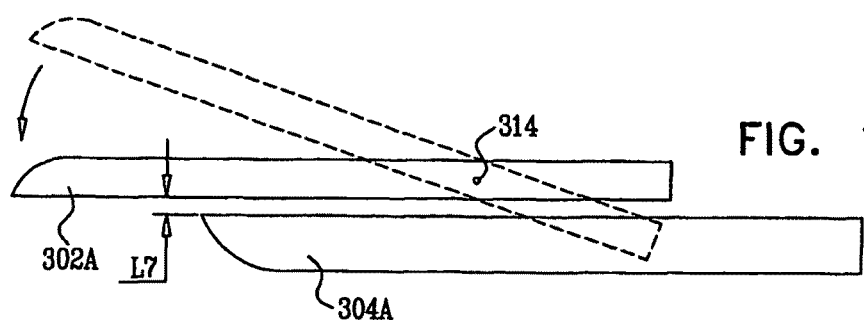

Reference is now made to FIGS. 13D-G, which are schematic illustrations of a transabdominal implantation tool 300A, in accordance with an embodiment of the present invention. Tool 300A is generally similar to and used in the same manner as tool 300 described hereinabove with reference to FIGS. 13A-C. Tool 300A comprises a puncturing element 302A, a sharp distal tip 306A, and a base 304A, which function generally similarly to corresponding parts of tool 300. FIG. 13D shows tool 300A in a closed position. In FIG. 13E, puncturing element 302A rotates around a hinge 312. In FIG. 13F, element 302A translates along its longitudinal axis, and in FIG. 13G, element 302A rotates around a hinge 314, so as to close upon gastric wall tissue.

Reference is now made to FIGS. 13A-G. A gap between opposing faces of element 302 and base 304, or between element 302A and base 304A, is typically selected to approximately match a local thickness of the gastric wall, or to be slightly smaller than the natural local thickness, so as to clamp the gastric wall. For example, the distance L7 between the two faces may be between about 2 and 5 mm (e.g., approximately 3 mm). In this manner, an electrode implanted using tool 300 or tool 300A is generally parallel to the gastric wall, and a significant length of the electrode (e.g., at least three times the thickness of the gastric wall) is implanted at a generally fixed depth within the wall.

It is to be appreciated that the general functionality achieved by tools 300 and 300A, or similar functionality, may be attained using a variety of mechanisms that will be obvious to a person of ordinary skill in the art having read the disclosure of the present patent application.

Figure 14:
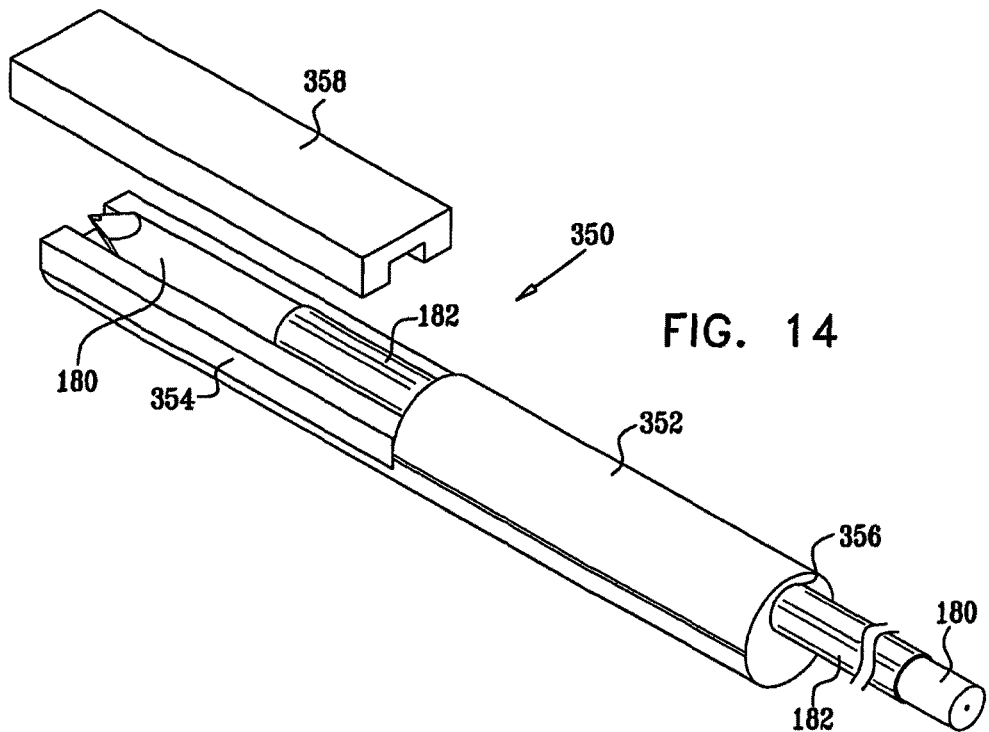
FIG. 14 is a schematic illustration of a gastric electrode implantation system, in accordance with an embodiment of the present invention.

Reference is made to FIG. 14, which is a schematic illustration of a gastric electrode implantation system 350, in accordance with an embodiment of the present invention. System 350 comprises a transabdominal implantation tool 352, which is used instead of transabdominal implantation tool 170 for inserting submucosal needle 180 and sheath 182 into submucosal layer 218 (FIG. 9A). Tool 352 comprises a first magnetic (typically electromagnetic) coupling element 354, and is shaped so as to define a channel 356 for receiving submucosal needle 180. System 350 further comprises a second magnetic coupling element 358, which is adapted to be placed in stomach 10.

During an electrode implantation procedure, tool 352 is laparoscopically advanced to an external surface of stomach 10. For example, techniques may be used that are described hereinabove with reference to steps 100-144 of FIG. 2A and steps 200-202 of FIG. 2B. Second coupling element 358 is endoscopically advanced to a location in the stomach in a vicinity of first coupling element 354, and so as to be in alignment therewith. The magnets attract each other, thereby drawing transabdominal implantation tool 352 against and substantially parallel to the outer surface of the stomach. Submucosal needle 180 is introduced through the channel, and is advanced into submucosal layer 218, such as by using the technique described hereinabove with reference to step 230 of the method of FIG. 2B. Submucosal needle 180 is withdrawn, and one or more electrodes are implanted in the gastric wall, such as by using techniques described hereinabove with reference to steps 232-258 of the method of FIG. 2B.

Endoluminal Transgastric Approach

Figure 15A:
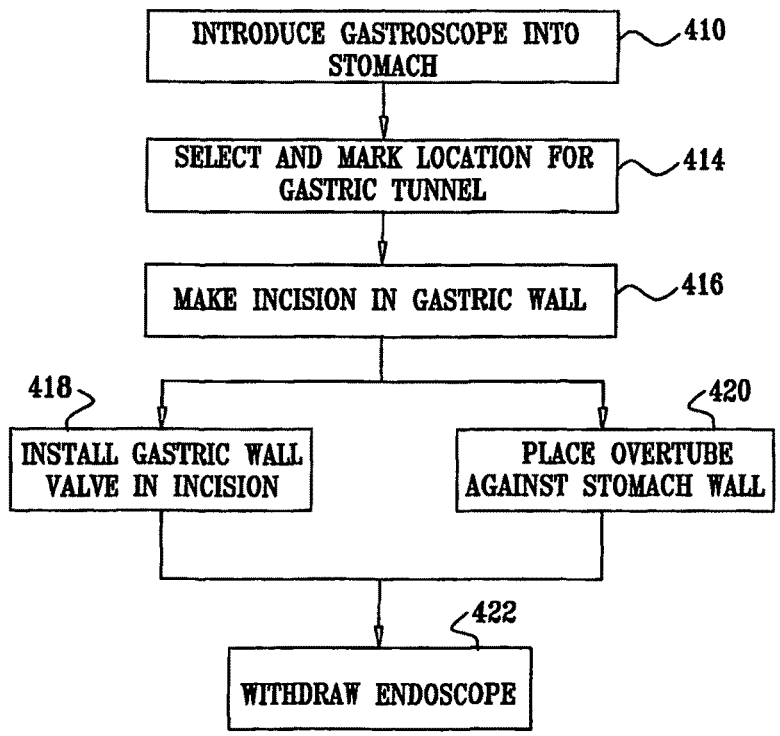
FIGS. 15A-B are flow charts that schematically illustrate a method for implanting electrodes in a gastric wall using a per-oral endoluminal transgastric approach, in accordance with an embodiment of the present invention.
Figure 15B:
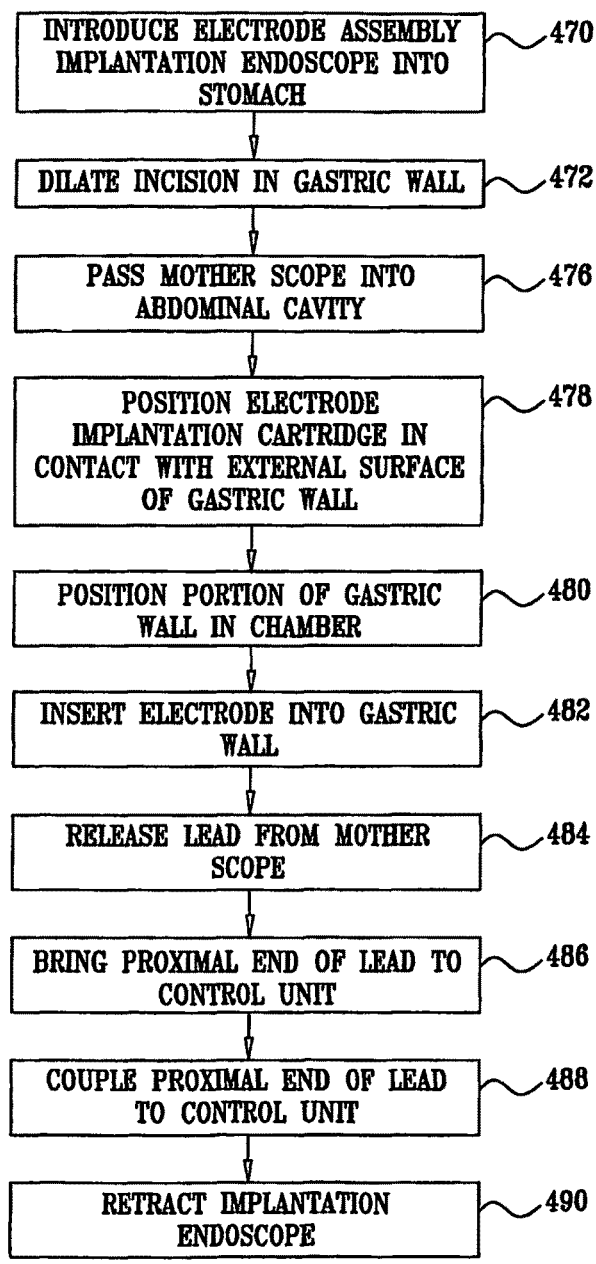

FIGS. 15A-B are flow charts that schematically illustrate a method for implanting electrodes in gastric wall 30 using a per-oral endoluminal transgastric approach, in accordance with an embodiment of the present invention. FIG. 15A illustrates a preparatory stage of the method, and FIG. 15B illustrates an implantation stage of the method. The method is typically performed under conscious sedation. Insufflation of abdominal cavity 20 is typically not necessary.

Figure 16:
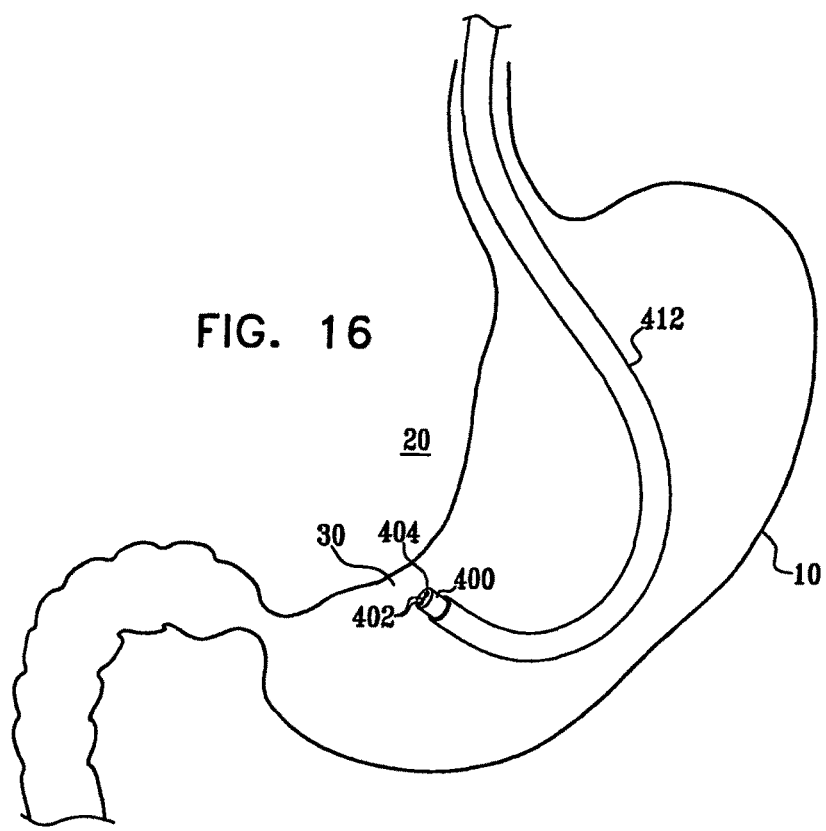
FIG. 16 is a schematic illustration of a gastroscope inserted into a stomach, in accordance with an embodiment of the present invention.

FIG. 16 is a schematic illustration of a gastroscope 400 inserted into stomach 10, in accordance with an embodiment of the present invention. Gastroscope 400 typically comprises a plurality of working channels 402, and an imaging system 404, which comprises a light source and an image sensor (e.g., a CCD or CMOS image sensor, or any visible band image sensor). The imaging system is typically configured to enable wide-angle (greater than about 130-degree) viewing.

Returning to FIG. 15A, at a gastroscope introduction step 410, transgastric tunneling endoscope 400 is introduced into stomach 10 via the mouth. (The stomach is typically at least partially insufflated.) In order to reduce the likelihood of peritoneal infection, the stomach is irrigated with an antibiotic solution. For some applications, gastroscope 400 is advanced through a sterile flexible over-tube 412 (FIG. 16), which extends from the mouth to at least the gastroesophageal junction. The use of such an over-tube isolates the gastroscope from the pharynx and esophagus, reducing the likelihood of cross-contamination of the peritoneal cavity.

Using the imaging (typically wide-angled) capabilities of the gastroscope, an examination of the stomach is performed in order to determine whether stomach conditions are suitable for the procedure, and to exclude other pathologies. At a location marking step 414, the stomach is fully insufflated, and a site for creating a gastric tunnel is selected, typically on the mid-anterior wall of the stomach, and is suitably marked (for example, using a removable clip). The wide-angle view of the imaging system facilitates the simultaneous viewing of the fundus and pylorus, which enables the accurate location of the mid-anterior wall of the stomach.

At a tunneling incision step 416, a transgastric incision tool is advanced through one of the working channels of the gastroscope. For example, the tool may comprise forceps and/or a grasper, and a cutting tool, such as a scalpel (e.g., a harmonic scalpel), a laser (e.g., a CO2 laser), an ultrasound device, a diathermy (RF) device, and/or a sphincterotome and an RF needle. The forceps are used to grasp tissue of gastric wall 30, and the cutting tool is used to make an incision in the wall. For some applications, a gastric wall valve is inserted into and coupled to the incision, at a gastric wall valve installation step 418. Alternatively, over-tube 412 is advanced until its distal end comes in contact with gastric wall 30, and the distal end is coupled in tight contact with the wall, at an over-tube placement step 420. This placement of the over-tube reduces the likelihood of contamination of the incision, and generally obviates the need to install a gastric wall valve. Endoscope 400 is withdrawn from the stomach, at a withdrawal step 422, completing the preparatory stage of the method.

Reference is made to FIG. 17, which is a schematic illustration of an electrode assembly implantation endoscope 450, in accordance with an embodiment of the present invention. Endoscope 450 comprises a mother scope 452, and, typically, a baby scope 454. Baby scope 454 is advanced through a channel of mother scope 452 until a distal portion of the baby scope exits the mother scope through an opening 456 in a vicinity of the distal end of the mother scope. Opening 456 is typically between about 5 and about 20 cm from the distal end of mother scope 452, e.g., about 15 cm. A distal end of baby scope 454 comprises an imaging system, which comprises an image sensor (e.g., a CCD) and a light source (e.g., one or more LEDs, a xenon light, a halogen light, a white light, and/or a metal halide lamp, and/or optical fibers to carry light). A distal end of mother scope 452 typically comprises an image sensor (e.g., a CCD) and a light source (e.g., one or more LEDs and/or other light sources described herein). Mother scope 452 typically has an outer diameter of between about 15 and about 18 mm, and baby scope 454 typically has an outer diameter of between about 2 and about 3.9 mm. An example of such a system is the Medigus Transgastric Mother video endoscope known as TR106, which has a 15.5 mm outer diameter and includes three 6 mm working channels and two 3.9 mm working channels. Baby scope 454 may comprise a baby scope also manufactured by Medigus, Ltd., known as TRB35, which has an outer diameter of 3.5 mm, and includes a 1.2 mm working channel. For some applications, both the TR106 and TRB35 are coupled to one or more suitable video processors and illumination systems, to enable the display of two separate video signals.

In a vicinity of a distal end thereof, mother scope 452 comprises an electrode implantation cartridge 458. Cartridge 458 holds and is adapted to implant one or more (typically two) electrodes 460 into gastric wall 30. Cartridge 458 is shaped so as to define at least one lateral chamber 462, which receives and positions a portion of gastric wall 30 for properly aligned insertion of electrode 460, as described hereinbelow with reference to step 480 of FIG. 15B. Typically, chamber 462 comprises one or more vacuum ports 463, which draw and hold the gastric wall in the chamber during insertion of the electrode, such that the distal end of mother scope 452 is substantially parallel to gastric wall 30 at the site of insertion of electrode 460, as shown. Alternatively or additionally, chamber 462 comprises a clamp that grasps the gastric wall (configuration not shown). For some applications, the clamp is shaped so as to facilitate proper insertion of the electrode, e.g., the clamp is shaped so as to define guiding threads.

Mother scope 452 is configured to hold one or more (typically two) electrode leads 464, which are coupled to respective electrodes 460. After each electrode is implanted in gastric wall 30, the corresponding lead is released from the mother scope, and the proximal end of the lead is coupled to a control unit, as described hereinbelow with reference to step 488 of FIG. 15B.

At an endoscope introduction step 470 of the method of FIG. 15B, electrode assembly implantation endoscope 450 is introduced into stomach 10 via the mouth, with baby scope 454 retracted within mother scope 452. Once the endoscope is in the stomach, baby scope 452 is extended from mother scope 452, as shown in FIG. 3017. The distal end of mother scope 452 is advanced to the site of the incision. If a gastric wall valve was installed at step 418 of FIG. 15A, the valve is removed. At an optional dilation step 472, a dilating mechanism is inserted into the incision made at step 416 of FIG. 15A. The dilating mechanism dilates the incision so that mother scope 452 can pass through the incision. For some applications, the dilating mechanism comprises a balloon that dilates the incision and weakens the lips thereof for a brief period, during which the mother scope passes through the incision. For some applications, a CO2 laser, electrocautery device, or other energy-based cutting tool makes the incision (e.g., a 5 mm incision), and, optionally, the dilating mechanism is not used.

The distal end of mother scope 452 is passed through the dilated incision into abdominal cavity 20 of the subject, at an abdominal passage step 476. At a cartridge positioning step 478, the mother scope is manipulated so that a lateral surface of electrode implantation cartridge 458 is brought into contact with the external surface of the gastric wall (e.g., such that a longitudinal axis of the cartridge is generally parallel with the gastric wall, as shown in FIG. 17, or is generally perpendicular with the gastric wall (configuration not shown)). A portion of the gastric wall is positioned in chamber 462, at a gastric wall chamber positioning step 480. For some applications, baby scope 454 is used to help obtain proper positioning at steps 478 and/or 480. For example, mother scope 452 may comprises one or more lights sources 481 (e.g., LEDs and/or other light sources described herein) in a vicinity of a distal end of the mother scope, as shown in FIG. 17. Light sources 481 produce illumination that can be seen through gastric wall 20 by the image sensor of baby scope 454. For some applications, light sources 481 comprise two or more light sources which emit different colors, or emit in respective characteristic spatial or temporal patterns. These light sources are viewed using the image sensor of the baby scope in order to confirm proper placement and orientation of cartridge 458. For applications in which chamber 462 comprises vacuum ports 463, negative pressure applied by the ports assists in drawing and holding the gastric wall in the chamber.

At an electrode insertion step 482, cartridge 458 inserts electrode 460 into tissue of the gastric wall, typically into a submucosal layer thereof. The imaging system of baby scope 454 is typically used to observe the electrode placement from within the stomach, so as to aid in the placement of the electrode in the desired location, and to detect any perforation of the gastric wall that may accidentally occur. In some embodiments of the present invention, techniques described hereinbelow with reference to FIGS. 20-39 are used for inserting and securing the electrode in the gastric wall.

After the electrode has been inserted, its lead 464 is released from mother scope 452, at a lead release step 484. At a lead placement step 486, the proximal end of lead 464 (i.e., the end not coupled to electrode 460) is brought through abdominal cavity 20 to the location of an external or implanted control unit, such as a pulse generator. Typically, the proximal end of the lead is brought into a vicinity of skin of the subject, where it is coupled to an external or subcutaneously-implanted control unit, at a lead coupling step 488. For some applications, the proximal end of the lead is brought into the vicinity of the skin by introducing a tool from outside the body, coupling the tool to the proximal end of the lead, and pulling the proximal end of the lead to the vicinity of the skin using the tool.

At a retraction step 490, implantation endoscope 450 is retracted into stomach 10, and then out of the stomach via the mouth. At a stapling step 492, a stapling device is introduced into the stomach and brought to a vicinity of the incision in the gastric wall made at step 416 of the method of FIG. 15A. The stapling device comprises a stapler and forceps. The stapler and forceps are introduced through working channels of gastroscope 400, described hereinabove with reference to FIG. 16, or using a separate gastroscope. The forceps are typically used to hold the tissue during stapling. The stapling is typically observed using an imaging system, in order to aid with the performance of the procedure and to confirm successful closure of the incision.

Figure 18A:
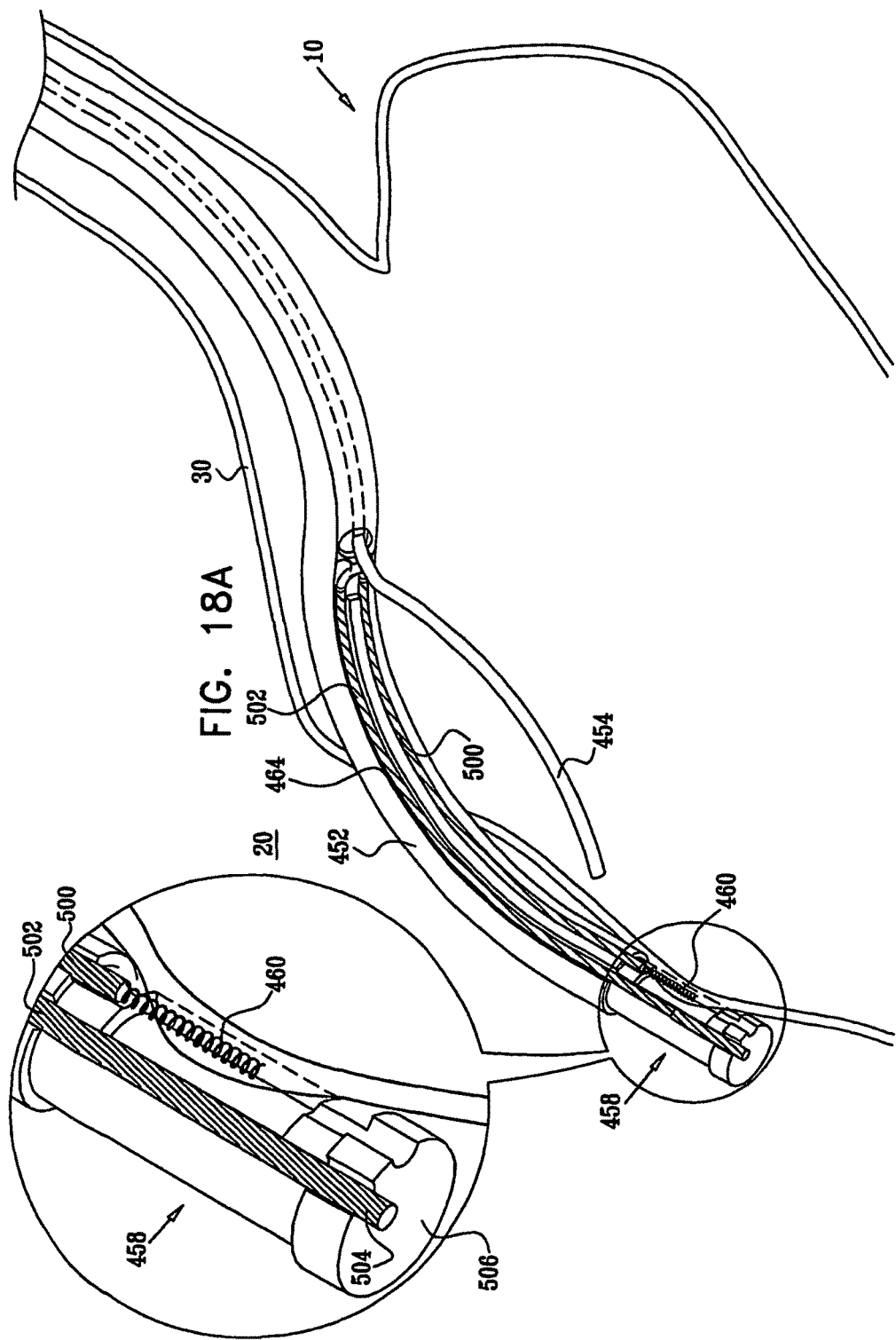
FIGS. 18A-B are schematic illustrations of a configuration of a mother scope of the endoscope of FIG. 17, in accordance with an embodiment of the present invention.
Figure 18B:
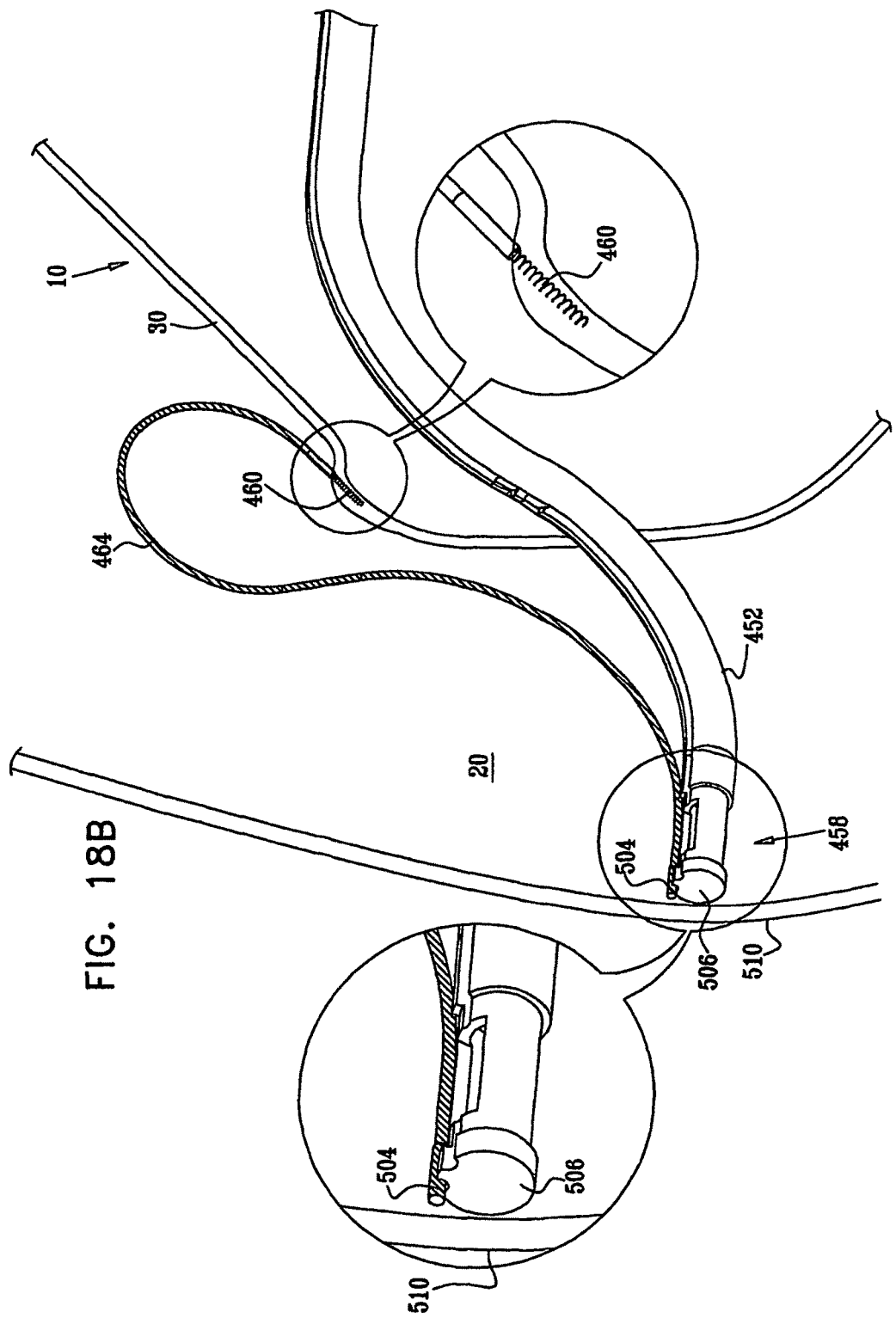

Reference is made to FIGS. 18A-B, which are schematic illustrations of a configuration of mother scope 452, in accordance with an embodiment of the present invention. In the configuration shown in FIG. 18A, electrode lead 464 is initially coupled to mother scope 452 such that it doubles back towards cartridge 458, i.e., first and second central portions 500 and 502 of the lead are arranged alongside one another on the mother scope. A coupling end 504 of lead 464 is positioned in a vicinity of a distal end 506 of mother scope 452.

As shown in FIG. 18B, after electrode 460 has been implanted in gastric wall 30, electrode lead 464 is released from mother scope 452, and distal end 506 of the mother scope is brought through abdominal cavity 20 towards a wall 510 of the abdomen. Coupling end 504 of lead 464 is coupled to an external or implanted control unit, and released from mother scope 452.

Figure 18C:
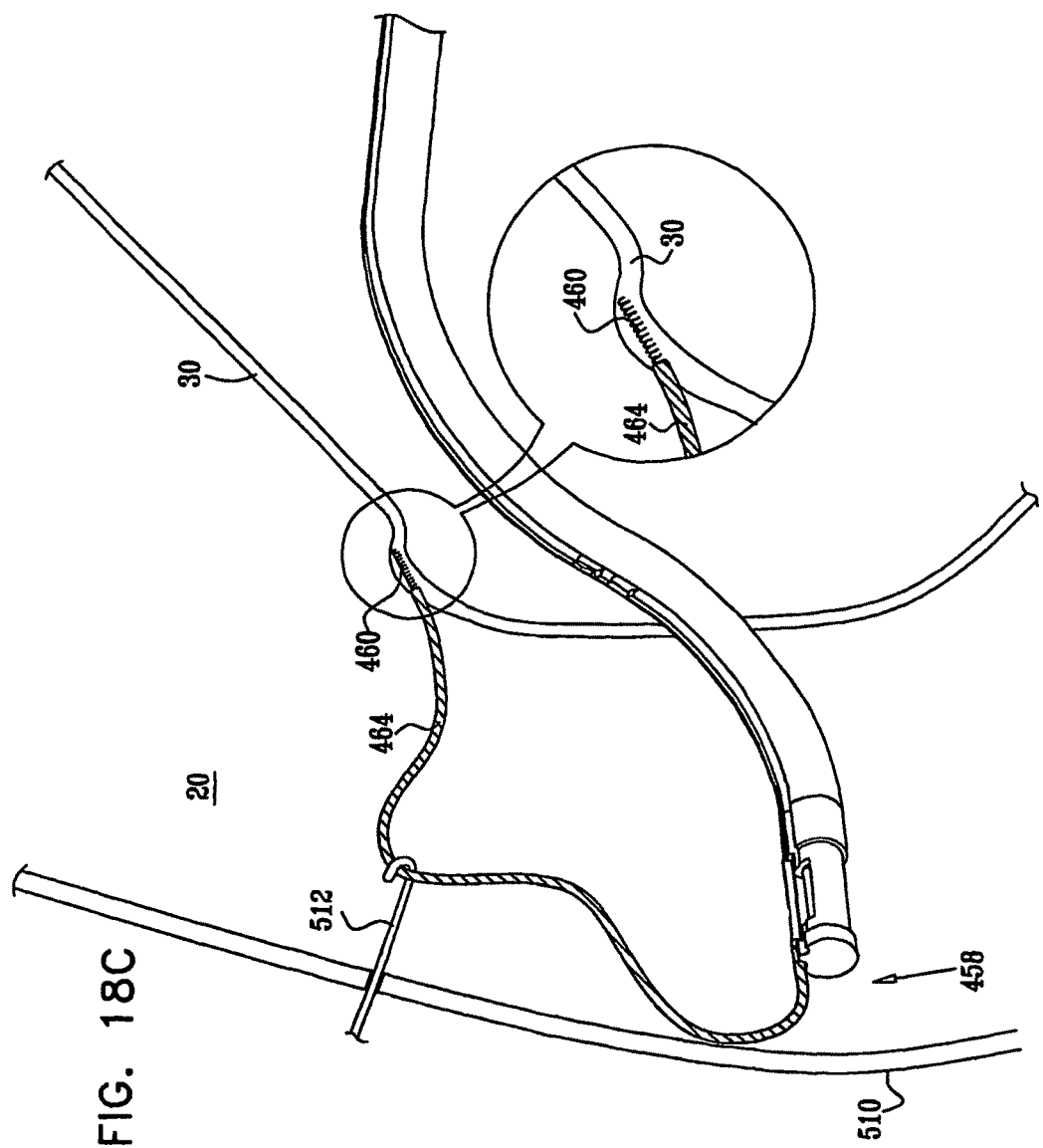
FIG. 18C is a schematic illustration of a configuration of a mother scope of the endoscope of FIG. 17, in accordance with another embodiment of the present invention.

Reference is made to FIG. 18C, which is a schematic illustration of a configuration of mother scope 452, in accordance with another embodiment of the present invention. The embodiment shown in FIG. 18C is generally similar to that described hereinabove with reference to FIGS. 18A-B. For some applications, the embodiment shown in FIG. 18C is practiced in combination with the embodiment described hereinbelow with reference to FIG. 39. Typically, a grabbing mechanism (such as a hook 512) is passed transabdominally, and grabs lead 464, in order to bring it towards a control unit (not shown) and facilitate coupling of the lead to the control unit.

Figure 19:
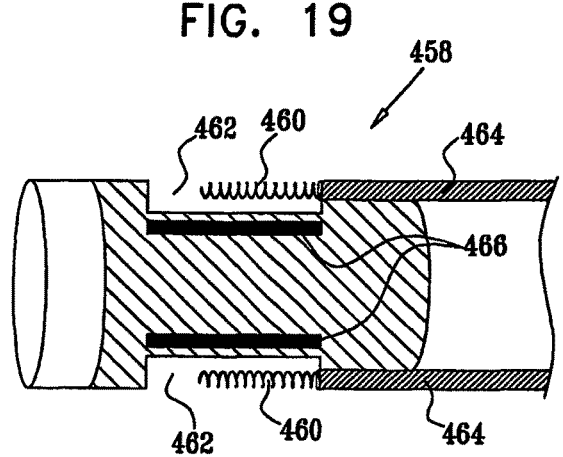
FIG. 19 is a schematic illustration of a distal portion of the mother scope of the endoscope of FIG. 17, in accordance with an embodiment of the present invention.

Reference is made to FIG. 19, which is a schematic illustration of a distal portion of mother scope 452, in accordance with an embodiment of the present invention. In this embodiment, implantation cartridge 458 of mother scope 452 is shaped so as to define a plurality of lateral chambers 462 (e.g., two lateral chambers spaced by 180 degrees (as shown)), which hold respective electrodes 460 coupled to respective electrode leads 464. During an implantation procedure, steps 478 through 488 of the method of FIG. 15B are repeated one or more times in order to implant the plurality of electrodes 460 in the gastric wall. A first one of lateral chambers 462 is brought into contact with the external surface of the gastric wall, its electrode 460 is implanted, and the respective lead is brought towards the wall of the abdomen for coupling to a control unit. Implantation cartridge 458 and/or the distal end of mother scope 452 is rotated, until a second one of the lateral chambers is brought into contact with the gastric wall, and its electrode is implanted. These rotation/implantation steps are repeated until all of the electrodes have been implanted.

For some applications, the use of this rotation technique results in the implantation of a plurality of electrodes in the gastric wall at respective distances from one another which are equal to the respective circumferential distances between the electrodes while they are held by the cartridge. In addition, the use of cartridge 458 enables two or more electrodes to be consistently implanted parallel to one another, and at a constant depth in the gastric wall. Alternatively or additionally, the use of a multiple-electrode implantation cartridge 458 facilitates an easier implantation procedure, in which tools and electrodes do not need to be advanced and withdrawn via mother scope 452 for each additional electrode that is implanted. Typically, the placement of a first electrode in this manner stabilizes cartridge 458 with respect to the gastric wall to some extent, to facilitate rotating of cartridge 458 (e.g., by 180 degrees) without loss of alignment with respect to the gastric wall in preparation for implanting a second electrode. Alternatively or additionally, suction applied at a site during implantation of the first electrode is applied at the same site during rotation of cartridge 458, until suction is applied at the site designated for implantation of the second electrode. For some applications, leads 464 are coupled to one another, or are enclosed in a single lead housing, along a portion thereof (configuration not shown).

Reference is still made to FIG. 19. In an embodiment of the present invention, implantation cartridge 458 comprises a magnet 466, e.g., a permanent magnet or electromagnet, in a vicinity of each chamber 462. Electrode 460 comprises a magnetically-attracted material, such as stainless steel. During an implantation procedure, electrode 460 is attracted to magnet 466, which stabilizes the electrode, preventing the electrode from deflecting away from the cartridge and thereby exiting gastric wall 30 into the lumen of the stomach.

Electrode Devices

Reference is made to FIGS. 20-38, which are schematic illustrations of electrode devices, in accordance with respective embodiments of the present invention. Most of these electrode devices comprise an electrode assembly, which is implanted in the gastric wall; an electrode lead; and an implantation tool, which is used to implant the electrode assembly, and is thereafter removed from the body of the subject. For some applications, these electrode devices are used in combination with cartridge 458 of mother scope 452, which is described hereinabove with reference to FIGS. 17-19. The electrode assembly and implantation tool are preloaded in the cartridge. After implanting the electrode assembly in the gastric wall, the tool is withdrawn into the cartridge. Alternatively, these electrode devices are used with other endoluminal (per oral) transgastric or intragastric approaches. Further alternatively, these electrode devices are used with the combined endoscopic and transabdominal approach described hereinabove with reference to FIGS. 1-14, such as with the techniques described with reference to FIGS. 13A-E or 14, or with other surgical approaches known in the art.

Non-Coaxial Electrode Devices

Reference is made to FIGS. 20-29, which are schematic illustrations of non-coaxial electrode devices, in accordance with respective embodiments of the present invention. In these embodiments, at least a portion of the electrode assembly and/or the electrode lead is not coaxial with the implantation tool. When these electrode devices are used with cartridge 458 of mother scope 452, such non-coaxial alignment generally facilitates the withdrawal of the implantation tool into the cartridge and the subsequent release of electrode lead 464 from the mother scope.

FIG. 20 is a schematic illustration of a non-coaxial tine-coupling electrode device 600, in accordance with an embodiment of the present invention. Electrode device 600 comprises an implantation tool 602, an electrode assembly 604, and an electrode lead 606. The electrode assembly and the lead are coaxial with one another, but not with the tool. Electrode assembly 604 and lead 606 together comprise a non-conductive shaft 610, which typically comprises nylon, polyethylene, polyester, or another suitable material. Electrode assembly 604 comprises a non-insulated wire 608 coiled around a portion of shaft 610, either in a clockwise or counterclockwise direction. Wire 608 typically comprises platinum-iridium with a titanium nitride (TiN) coating, titanium coated with iridium oxide, platinum-iridium coated with iridium oxide, or another suitable material. Wire 608 is fixed to shaft 610. At a distal end thereof, the electrode assembly comprises a coupling element 612, which typically comprises two or more tines 614. For some applications, tines 614 are flexible, and comprise, for example, silicone, polyurethane, ETFE, or PTFE. Alternatively, tines 614 are rigid, and comprise, for example, a metal. For some applications, tines 614 comprise rigid metallic barbs.

Coupling element 612 typically has a diameter D1 at its narrowest distal end of between about 0.7 and about 0.9 mm, e.g., about 0.8 mm, and a length L1 of between about 4 and about 6 mm, e.g., about 5 mm. Shaft 610 typically has a diameter D2 of between about 0.3 and about 0.5 mm, e.g., about 0.4 mm, and a total length L2 between the proximal end of coupling element 612 and the distal end of lead 606 of between about 20 and about 26 mm, e.g., about 23 mm. Wire 608 is coiled around a portion of shaft 610 at the proximal end of electrode assembly 604 typically having a length L3 of between about 15 and about 20 mm, e.g., about 18 mm. The coil formed by wire 608 typically has an outer diameter D3 of between about 0.5 and about 0.7 mm, e.g., about 0.6 mm.

Electrode assembly 604 further comprises, at a distal end thereof, a hooking assembly 616, which comprises an elongated flexible element 618, which typically has a diameter D4 of between about 0.2 and about 0.3 mm, e.g., about 0.25 mm. In a vicinity of a distal end thereof, hooking assembly 616 comprises a hook 620, which is adapted to be removably coupled to tool 602, as described hereinbelow. For some applications, hook 620 is formed by looping the distal end of flexible element 618, as shown in FIG. 20. Alternative configurations of hook 620 are described hereinbelow with reference to FIGS. 23A-B.

Lead 606 comprises an elongated conductor 630, e.g., comprising MP35N with a silver core or a Drawn Filled Tube (DFT), or 35N LT® with a silver core or a DFT. Conductor 630 is typically coiled around the portion of shaft 610 which lead 606 comprises. Lead 606 comprises a non-conductive sleeve or coating 632, which comprises, for example, silicone. Conductor 630 and coating 632 are typically not fixed to shaft 610, such that shaft 610 is able to slide with respect to the conductor and lead. The proximal end of shaft 610 comprises a handle 634, for assisting with the retraction of shaft 610, as described hereinbelow.

Reference is made to FIG. 21, which is a schematic cross-sectional illustration of a coupling of wire 608 of electrode assembly 604 to conductor 630, in accordance with an embodiment of the present invention. The wire is coupled to conductor 630 by coupling (e.g., crimping or welding) both the wire and the conductor to an external surface of a conductive metal tube 640. This configuration allows shaft 610 to slide with respect to tube 640, wire 608, and conductor 630.

Reference is again made to FIG. 20. Implantation tool 602 comprises a proximal base 642 coupled to a hollow distal needle 644, which comprises, for example, stainless steel. Needle 644 is shaped so as to define a sharp distal tip 645. Needle 644 typically has an external diameter D5 of between about 1 and about 1.4 mm, e.g., about 1.2 mm, and an internal diameter D6 of between about 0.7 and about 0.9 mm, e.g., about 0.8 mm. Tool 602 comprises a generally rigid stylet 646, which is typically non-slidably fixed to proximal base 642. Stylet 646 typically has a proximal portion that has a diameter greater than that of a distal portion thereof. For example, the proximal portion may have a diameter D7 of between about 0.3 and about 0.5 mm, e.g., about 0.4 mm, while the distal portion may have a diameter D8 of between about 0.1 and about 0.3 mm, e.g., about 0.2 mm. Stylet 646 typically has a total length L4 of between about 30 and about 40 mm, e.g., about 35 mm.

A distal portion of needle 644 typically comprises a plug 648, which comprises, for example, a polymer, e.g., Delrin® (DuPont). Plug 648 typically has a length L5 of between about 1.8 and about 2.2 mm, e.g., about 2 mm. A distance D9 of between about 0.8 and about 1.2 mm, e.g., about 1 mm, typically separates a distal tip of stylet 646 from the proximal end of plug 648. For some applications, at least a portion of needle 644 is slightly curved. For example, the distal portion of the needle (having length L5) may be slightly curved.

Needle 644 is shaped so as to define a lateral opening 650, through which flexible element 618 of hooking assembly 616 passes. Hook 620 is adapted to be removably coupled to stylet 646 in a vicinity of the distal tip of the stylet.

Reference is made to FIG. 22, which is a schematic illustration of electrode device 600 during an electrode implantation procedure, in accordance with an embodiment of the present invention. Implantation tool 602 is advanced through gastric wall 30 in a direction roughly parallel to the wall, such that the tool enters the wall at a first site on an external surface thereof in abdominal cavity 20, and exits at a second site on the external surface. The tool generally does not enter the lumen of stomach 10. As tool 602 is advanced through gastric wall 30, it pulls electrode assembly 604 alongside the tool through the gastric wall, until coupling element 612 exits the gastric wall at the second site thereon. The tool is then withdrawn proximally (i.e., to the right in FIG. 22). Hook 620 disengages from stylet 646 as the tool is withdrawn. Proximal handle 634 of shaft 610 is withdrawn proximally, pulling coupling element 612 against the tissue of the external surface of gastric wall 30. Tines 614 of coupling element 612 prevent the coupling element from reentering the gastric wall, thereby securing electrode assembly 604 to the gastric wall. Because shaft 610 is free to move with respect to wire 608, the wire remains in place in the tissue of the gastric wall as the shaft is withdrawn proximally.

For some applications, coupling element 612 comprises a coupling mechanism other than tines 614. For example, the coupling element may comprise T-anchor 1214 described hereinbelow with reference to FIGS. 34-36.

Reference is made to FIGS. 23A-B, which are schematic illustrations of alternative configurations of hook 620 of hooking assembly 616, in accordance with respective embodiments of the present invention. In the configuration shown in FIG. 23A, hook 620 comprises a loop 652, through which stylet 646 passes, thereby removably coupling the hook to the stylet. In the configuration shown in FIG. 23B, hook 620 comprises a cup-shaped element 654, which holds the distal end of stylet 646, thereby removably coupling the hook to the stylet. Other configurations of hook 620 will be evident to those skilled in the art who have read the present application, and are considered within the scope of the present invention.

FIG. 24 is a schematic illustration of a non-coaxial rod-guided electrode device 700, in accordance with an embodiment of the present invention. Electrode device 700 comprises an implantation tool 702, an electrode assembly 704, and an electrode lead 706. Tool 702 is shaped so as to define a proximal portion 750 and a distal portion 752. Prior to and during a portion of an implantation procedure, as described hereinbelow, a distal portion 708 of electrode assembly 704 is held within distal portion 752 of tool 702, such that distal portion 708 of electrode assembly 704 is generally coaxial with tool 702. In contrast, lead 706 and a proximal portion 709 of electrode assembly 704 remain outside tool 702 at all times, and are thus not coaxial with tool 702.

Electrode assembly 704 comprises a core 710. For some applications, core 710 is non-conductive and flexible. For these applications, core 710 typically comprises a suture, which may comprise, for example, nylon, polyethylene, polyester, or another suitable material. For other applications, core 710 is conductive and not insulated, and typically comprises a cable, which may comprise titanium. For applications in which core 710 is non-conductive, and, optionally, for applications in which core 710 is conductive, a non-insulated wire 711 is coiled around at least a portion of core 710. Wire 711 typically comprises platinum-iridium with a TiN coating, or another suitable material. At a distal end thereof, the electrode assembly comprises a coupling element 712, which typically comprises two or more tines 714. For some applications, tines 714 are flexible, and comprise, for example, silicone, polyurethane, ETFE, or PTFE. Alternatively, tines 714 are rigid, and comprise, for example, a metal. For some applications, tines 714 comprise rigid metallic barbs.

Coupling element 712 typically has a diameter D1 at its narrowest distal end of between about 0.7 and about 0.9 mm, e.g., about 0.8 mm, and a length L1 of between about 4 and about 6 mm, e.g., about 5 mm. Core 710 may be conductive or non-conductive, and typically has a diameter D2 of between about 0.8 and about 1.2 mm, e.g., about 1.0 mm. The coil formed by wire 711 typically has an outer diameter D3 of between about 0.5 and about 0.7 mm, e.g., about 0.6 mm, and wire 711 typically has a diameter of between about 0.075 and about 0.125 mm, e.g., about 0.1 mm.

Lead 706 comprises an elongated conductor 730, which is typically coiled around a core 731, which typically comprises a suture (e.g., 0.25 mm nylon) or a cable (e.g., 7×7 35N LT®). Lead 706 comprises a non-conductive sleeve or coating 732, which comprises, for example, silicone. Wire 711 of electrode assembly 704 and conductor 730 are typically coupled together in a vicinity of the distal end of lead 706 by a crimp tube 733.

Implantation tool 702 comprises a rod 744, which comprises, for example, stainless steel. Rod 744 is shaped so as to define a sharp distal tip 745. For some applications, at least a portion of rod 744 is slightly curved. For example, a distal portion of the rod may be slightly curved.

Proximal portion 750 of rod 744 typically is shaped so as to define a bore 751, which holds a generally rigid mandrel 746. Mandrel 746 typically has a distal portion that has a diameter greater than that of a proximal portion thereof. For example, the proximal portion may have a diameter D7 of between about 0.3 and about 0.7 mm, e.g., about 0.4 mm, while the distal portion may have a diameter D8 of between about 0.7 and about 0.9 mm, e.g., about 0.8 mm. Proximal portion 750 of rod 744 typically has an external diameter D5 of between about 1.0 and about 1.5 mm, e.g., about 1.2 mm, and an internal diameter D6 of between about 0.8 and about 1.2 mm, e.g., about 1.0 mm. Proximal portion 750 typically has a length L3 of between about 500 and about 1500 mm, e.g., about 1000 mm.

Reference is made to FIG. 25, which is a schematic cross-sectional illustration of distal portion 752 of rod 744, in accordance with an embodiment of the present invention. In cross section, distal portion 752 is shaped so as to define less than a complete 360-degree circle. In other words, distal portion 752 is not shaped so as to define a bore. Typically, the cross section of distal portion 752 defines an arc having an angle of between about 250 and about 290 degrees, e.g., about 280 degrees. Alternatively, the arc has an angle that is between 180 and 250 degrees, between 90 and 180 degrees, or between about 0 degrees (i.e., it is a simple rod) and 90 degrees. The resulting lateral opening 760 in distal portion 752 of rod 744 allows distal portion 708 of electrode assembly 704 to be laterally inserted and removed from distal portion 752 of rod 744. Distal portion 752 typically has a length L2 of between about 15 and about 30 mm, e.g., about 23 mm.

For some applications, electrode device 700 comprises one or more coupling rings 762. The rings are typically coupled to distal portion 708 of electrode assembly 704, such as by crimping, and help hold distal portion 708 of electrode assembly 704 in distal portion 752 of tool 702.

Reference is again made to FIG. 24. Prior to an implantation procedure performed with device 700, distal portion 708 of electrode assembly 704 is held within distal portion 752 of tool 702. Implantation tool 702 is advanced through gastric wall 30 in a direction roughly parallel to the wall, such that the tool enters the wall at a first site on an external surface thereof in abdominal cavity 20, and exits at a second site on the external surface. The tool generally does not enter the lumen of stomach 10. Tool 702 is advanced through gastric wall 30 until coupling element 712 exits the gastric wall at the second site thereon. At this point during the procedure, distal portion 708 of electrode assembly 704 is within gastric wall 30, and also within distal portion 752 of rod 744.

Tool 702 is then withdrawn proximally (i.e., to the right in FIG. 24). As the tool is withdrawn, pressure is applied by the surgeon to a proximal handle 734 of mandrel 746, such that the mandrel remains substantially stationary with respect to gastric wall 30 as the rest of the tool is withdrawn. The stationary distal end of the mandrel helps prevent distal portion 708 of electrode assembly 704 from being withdrawn with the tool. Rings 762 remain substantially stationary with respect to gastric wall 30 and distal portion 708 of electrode assembly 704. The rings, remaining attached to electrode assembly 704, slide through distal portion 752 of rod 744, and exit through the open distal end of rod 744 as the rod is withdrawn proximally.

For some applications, tool 702 comprises a proximal cap 766, which prevents accidental contact with proximal handle 734. The cap is removed prior to the withdrawal of tool 702, as described hereinabove.

For some applications, coupling element 712 comprises a coupling mechanism other than tines 714. For example, the coupling element may comprise T-anchor 1214 described hereinbelow with reference to FIGS. 34-36.

Figure 26:
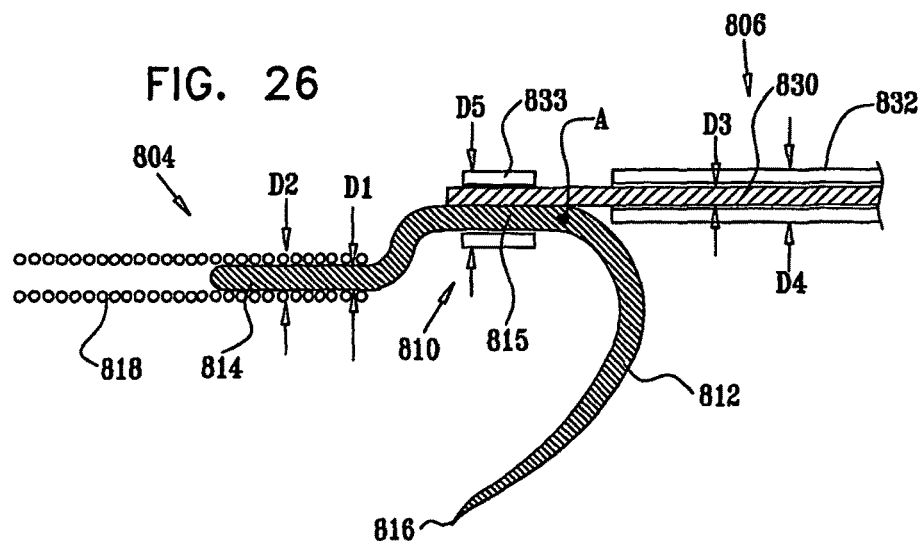
FIG. 26 is a schematic cross-sectional illustration of a non-coaxial electrode assembly and an electrode lead, in accordance with an embodiment of the present invention.

FIG. 26 is a schematic cross-sectional illustration of a non-coaxial electrode assembly 804 and an electrode lead 806, in accordance with an embodiment of the present invention. Electrode assembly 804 and electrode lead 806 are typically implanted using implantation tool 702, described hereinabove with reference to FIG. 24, mutatis mutandis. Electrode assembly 804 comprises a generally rigid hook assembly 810, which is shaped so as to define a hook 812, an electrode core 814 that is coaxial with tool 702, and a central portion 815 that is not coaxial with tool 702. Typically, hook assembly 810 is bent in a vicinity of a point. A between portion 815 and hook 812, such that hook 812 is oriented at an angle (e.g., 90 degrees) with respect to a plane defined by electrode assembly 804 and electrode lead 806 (i.e., the plane coinciding with the paper of FIG. 26). Hook 812 is shaped so as to define a sharp distal end 816. Typically, hook assembly 810 comprises a conductive material, such as titanium.

For some applications, a non-insulated wire 818 is coiled around at least a portion of electrode core 814. Wire 818 typically comprises platinum-iridium with a TiN coating, titanium with an iridium oxide coating, or another suitable material. Electrode core 814 typically has a diameter D1 of between about 0.2 and about 0.4 mm, e.g., about 0.3 mm. The coil formed by wire 818 typically has an outer diameter D2 of between about 0.4 and 0.6 mm, e.g., about 0.5 mm.

Lead 806 comprises an elongated conductor 830, which typically has a diameter D3 of between about 0.2 and about 0.4 mm, e.g., about 0.3 mm. Conductor 830 may comprise, for example, titanium, or 35N LT® with a silver core. For some applications, conductor 830 comprises a conductive cable, while for other applications the conductor comprises a wire coiled around a non-conductive or conductive core. Lead 806 comprises a non-conductive sleeve or coating 832, which comprises, for example, silicone. Sleeve 832 typically has an outer diameter D4 of between about 0.35 and about 0.45 mm, e.g., about 0.4 mm. Electrode core 814 and conductor 830 are typically coupled together by a crimp tube 833 in a vicinity of central portion 815 of hook assembly 810 and a distal end of conductor 830, such that the hook assembly is fixed with respect to conductor 830. Crimp tube 833 typically has an outer diameter D5 of between about 0.8 and about 1.2 mm, e.g., about 1 mm, and typically comprises titanium.

Prior to an implantation procedure, electrode core 814 and wire 818 are held within distal portion 752 of tool 702, as described hereinabove with reference to FIG. 24, mutatis mutandis. Implantation tool 702 is advanced through gastric wall 30 in a direction roughly parallel to the wall, such that the tool enters the wall at a site on an external surface thereof in abdominal cavity 20, and does not exit the gstric wall. At this point during the procedure, electrode core 814 and wire 818 are within gastric wall 30, and also within distal portion 752 of rod 744. Hook 812 is rotated until sharp distal end 816 anchors the hook into tissue of gastric wall 30. Tool 702 is then withdrawn proximally (i.e., to the right in FIG. 26), leaving electrode assembly 804 and electrode lead 806 implanted in the subject.

For some applications, electrode assembly 804 and electrode lead 806 are implanted endoscopically via stomach 10, or using a trocar via a laparoscopic transabdominal approach.

The endoscope or trocar typically provide separate channels for implantation tool 702 and hook 812.

Figure 27:
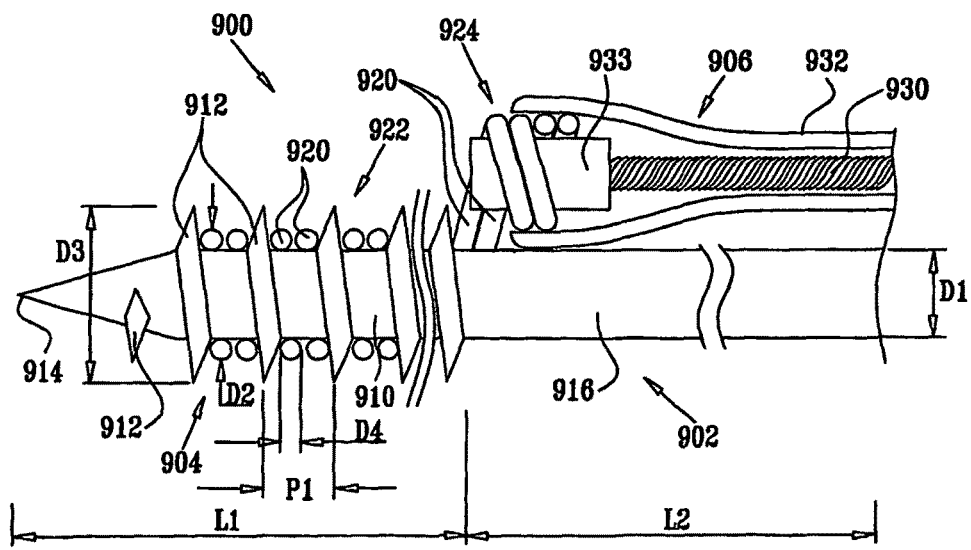
FIG. 27 is a schematic illustration of a non-coaxial screw-driven electrode device, in accordance with an embodiment of the present invention.

FIG. 27 is a schematic illustration of a non-coaxial screw-driven electrode device 900, in accordance with an embodiment of the present invention. Electrode device 900 comprises an implantation tool 902, an electrode assembly 904, and an electrode lead 906. Electrode assembly 904 is generally coaxial with tool 902, while electrode lead 906 is not coaxial with tool 902.

Tool 902 comprises: (a) a proximal shank 916; and (b) a distal screw 910, which is shaped so as to define a sharp distal tip 914 and a plurality of screw threads 912 (i.e., as with any standard screw, a single "master" thread appears to constitute the plurality of screw threads that are seen when the physical screw is viewed). Screw 910 enables insertion of device 900 into gastric wall 30. Electrode assembly 904 comprises at least one non-insulated wire 920, a distal portion 922 of which is coiled around screw 910 between threads 912. (In the embodiment shown in FIG. 27, electrode assembly 904 comprises two wires 920 coiled around screw 910 between threads 912.) A proximal portion 924 of wire 920 is coupled to an elongated conductor 930 of lead 906 using a weld or crimp tube 933. Typically, elongated conductor 930 comprises a cable or a wire coiled around a core, which typically comprises a suture (e.g., 0.25 mm nylon). Lead 906 further comprises a non-conductive sleeve or coating 932, which comprises, for example, silicone.

Screw 910 and shank 916 typically have a diameter D1 of between about 0.25 and about 0.5 mm, e.g., about 0.3 mm. Screw 910 typically has a length L1 of between about 10 and about 25 mm, e.g., about 18 mm, and shank 916 typically has a length L2 of between about 500 and about 1500 mm, e.g., about 1000 mm. The coil formed by wire 920 typically has an outer diameter D2 of between about 0.4 and about 0.8 mm, e.g., about 0.7 mm. Wire 920 typically has a diameter D4 of between about 0.075 and about 0.125 mm, e.g. about 0.1 mm. Screw threads 914 typically define an outer diameter D3 of between about 1.1 and about 1.5 mm, e.g., about 1.3 mm, and a thread pitch P1 of between about 0.4 and about 0.8 mm, e.g., about 0.6 mm.

During an implantation procedure performed with device 900, distal screw 910 of implantation tool 902 is advanced through gastric wall 30 in a direction roughly parallel to the wall, such that the tool enters the wall at a site on an external surface thereof in abdominal cavity 20, and does not exit the gastric wall. To advance screw 910, the entire electrode device is typically rotated (e.g., clockwise), including tool 902 and electrode lead 906. Rotation of the electrode device may be induced by the physician manually rotating the device, or by the release of a pre-loaded spring (not shown), whose energy is directed to inducing the desired rotation.

Tool 902 is then withdrawn proximally (i.e., to the right in FIG. 27), by rotating proximal shank 916 (e.g., counterclockwise), but not lead 906. As a result, screw 910 unscrews from wire 920, leaving wire 920 implanted in gastric wall 30.

For some applications, electrode assembly 904 comprises a cable in place of wire 920, which generally increases the flexibility of the electrode assembly, allowing it to withstand greater deformation.

In an embodiment, a distal portion of wire 920 extends distally a small distance further than as is shown in FIG. 27, and is shaped to define a loop (not shown) immediately proximal to sharp distal tip 914, but distal to the distal end of screw threads 912. The loop allows the screw to rotate within it, and prevents the wire from unintentionally being unwound from the screw during clockwise rotation of the screw if local material properties of the gastric wall resist entry of the wire into the tissue (even though the material properties of the gastric wall would be unable to resist entry of the screw).

FIG. 28 is a schematic illustration of a non-coaxial screw-fixated electrode device 1000, in accordance with an embodiment of the present invention. Electrode device 1000 comprises an electrode assembly 1004 and an electrode lead 1006.

Electrode assembly 1004 is not coaxial with electrode lead 1006. Electrode assembly 1004 comprises a distal screw 1008 coupled to a generally rigid shaft 1010, such as by a crimp tube 1011. Screw 1008 enables insertion and coupling of device 1000 in gastric wall 30. For some applications, shaft 1010 is non-conductive, and comprises, for example, nylon, polyethylene, polyester, or another suitable material. For other applications, shaft 1010 is conductive, and comprises, for example, titanium, MP35N, 35N LT®, or another suitable material. For some applications in which shaft 1010 is conductive, the shaft is coated with an insulator, such as parylene. For applications in which shaft 1010 is non-conductive (or is coated with a non-conductive coating), and, optionally, for applications in which core 1010 is conductive and non-insulated, a non-insulated wire 1020 is coiled around at least a portion of shaft 1010. Wire 1020 typically comprises platinum-iridium with a TiN coating, or another suitable material.

Electrode assembly 1004 further comprises a screwdriver head 1022, which is coupled to a proximal end of shaft 1010. Alternatively, the proximal end of shaft 1010 is shaped so as to define screwdriver head 1022. A proximal end 1024 of screwdriver head 1022 is shaped so as to enable releasable coupling with a screwdriver (screwdriver not shown in FIG. 28). For example, end 1024 may be square in cross-section, or may be shaped so as to define one or more notches. For some applications, the screwdriver used to rotate screwdriver head 1022 is flexible, for remote torque transmission, such as screwdriver 1240 described hereinbelow with reference to FIG. 32. Alternatively, mechanical, hydraulic or pneumatic pressure is used to rotate screwdriver head 1022.

At a site 1026 distal to screwdriver head 1022 and proximal to electrode assembly 1004, electrode device 1000 is coupled to electrode lead 1006 by a coupling assembly 1028. Coupling assembly 1028 typically comprises a double-crimp tube 1030, which is crimped (a) at a first location 1026, to wire 1020, and (b) at a second location 1034, to an elongated conductor 1040 of lead 1006. Typically, crimp tube 1030 comprises a crimp support element 1033, which enables shaft 1010 to rotate with respect to crimp tube 1030, as described hereinbelow. Double-crimp tube 1030 may comprise, for example, titanium or platinum/iridium.

Typically, elongated conductor 1040 comprises a cable or a wire coiled around a core, which may comprise a suture (e.g., 0.25 mm nylon). Lead 1006 further comprises a non-conductive sleeve or coating, which comprises, for example, silicone. A proximal end of conductor 1040 (i.e., the end not coupled to double-crimp tube 1030) is coupled to a connector pin 1042, e.g., by crimping and/or welding. A silicone sleeve 1044 is optionally placed around the area of coupling.

Distal screw 1008 typically has (a) an inner diameter D1 of between about 0.25 and about 0.5 mm, e.g., about 0.4 mm, (b) an outer diameter D2 of between about 0.8 and about 1.3 mm, e.g., about 1 mm, (c) a length L1 of between about 3 and about 4 mm, e.g., about 3.5 mm, and (d) a thread pitch P1 of between about 0.6 and about 0.8 mm, e.g., about 0.7 mm Shaft 1010 typically has a diameter D3 of between about 0.2 and about 0.3 mm, e.g., about 0.25 mm, and the coil formed by wire 1020 typically has an outer diameter D4 of between about 0.4 and about 0.6 mm, e.g., about 0.5 mm. Shaft 1010 typically has a length L2 between crimp tube 1011 and coupling assembly 1028 of between about 0.5 and about 0.8 mm, e.g., about 0.7 mm, and a length L3 between coupling assembly 1028 and the proximal end of the shaft of between about 3 and about 8 mm, e.g., about 5 mm.

Coupling element 1028 typically has a longitudinal length L4 of between about 1.8 and 2.2 mm, e.g., about 2 mm. Device 1000 typically has a length L5 between coupling assembly 1028 and proximal end 1024 of screwdriver head 1022 of between about 4 and about 10 mm, e.g., about 5 mm. Distal end 1024 typically has a length L6 of between about 0.8 and about 1.2 mm, e.g., about 1 mm.

For some applications, one or more insulating spacers 1046 are provided between distal screw 1008 and shaft 1010, and/or between coupling assembly 1028 and screwdriver head 1022. Such spacers may enable, for example, electrode device 1000 to be used for sensing, because screw 1008 and wire 1020 (together with shaft 1010 for applications in which the shaft is conductive) serve as separate electrodes. For example, electrode device 1000 may be used to detect muscle contraction.

Reference is made to FIG. 29, which is a schematic cross-sectional illustration of double-crimp tube 1030, in accordance with an embodiment of the present invention. Double-crimp tube 1030 typically has a cross-section that is elliptical in shape, with a major axis having a length A1 of between about 1.8 and about 2.2 mm, e.g., about 2 mm, and a minor axis having a length A2 of between about 1 and about 1.4 mm, e.g., about 1.2 mm. Support element 1033 of tube 1030 is shaped so as to define a first longitudinal opening 1050, through which shaft 1010 passes. Wire 1020 is crimped to an external surface of support element 1033. Opening 1050 typically has a diameter D5 of between about 0.7 and about 0.9 mm, e.g., about 0.8 mm. Double-crimp tube 1030 is also shaped so as to define a second opening 1052, into which elongated conductor 1040 of lead 1006 is coupled and crimped. Opening 1052 typically has a diameter D6 of between about 0.4 and about 0.6 mm, e.g., about 0.5 mm.

Reference is again made to FIG. 28. During an implantation procedure performed with device 1000, distal screw 1008 is advanced through gastric wall 30 in a direction roughly parallel to the wall, such that the tool enters the wall at a site on an external surface thereof in abdominal cavity 20, and does not exit the gastric wall. For some applications, to advance screw 1008, screwdriver head 1022 is rotated (e.g., clockwise) using a screwdriver (not shown), causing shaft 1010 and screw 1008 to rotate with respect to electrode assembly 1028 and the coil formed by wire 1020. Alternatively, the entire electrode device is rotated (e.g., clockwise), including screw 1008, shaft 1010, and electrode lead 1006, which are coupled to one another to prevent relative rotation with respect to one another. The screwdriver is withdrawn, leaving electrode assembly 1004, including screw 1008, implanted in gastric wall 30, and the remainder of electrode device 1000, including electrode lead 1006, implanted in the body of the subject. Lead 1006 is coupled to an implanted or external control unit, using connector pin 1042.

Coaxial Electrode Devices

Reference is made to FIGS. 30-38, which are schematic illustrations of coaxial electrode devices, in accordance with respective embodiments of the present invention. In these embodiments, the electrode assembly, electrode lead, and implantation tool are generally coaxial with one another.

FIG. 30 is a schematic illustration of a coaxial screw-driven electrode device 1100, in accordance with an embodiment of the present invention. Electrode device 1100 comprises an implantation tool 1102, an electrode assembly 1104, and an electrode lead 1106. Tool 1102, electrode assembly 1104, and electrode lead 1106 are generally coaxial with one another.

Implantation tool 1102 comprises a shaft 1110, a distal portion 1112 of which is shaped so as define a screw 1108 having a plurality of screw threads 1114, and a sharp distal tip 1116. Screw 1108 enables insertion of device 1100 into gastric wall 30. Electrode assembly 1104 comprises at least one non-insulated wire 1120, a distal portion of which is coiled around distal portion 1112 of shaft 1110 between threads 1114. (In the embodiment shown in FIG. 30, electrode assembly 1104 comprises two wires 1020 coiled around distal portion 1112 of shaft 1110 between threads 1114.) Wire 1120 may comprise, for example, titanium with a TiN coating, platinum-iridium with a TiN coating, titanium with an iridium oxide coating, or platinum-iridium with an iridium oxide coating.

A proximal portion of wire 1120 is coupled to an elongated conductor 1130 of lead 1106 using a crimp tube 1133, which may comprise, for example, titanium. Typically, elongated conductor 1130 comprises a cable or wire 1131 (which may comprise 35NLT (MP35N without titanium), for example), coiled around a flexible tube 1134, which may comprise, for example, silicone. Lead 1106 further comprises a non-conductive sleeve or coating 1132, which comprises, for example, silicone. For some applications, tool 1102 comprises a stop ring 1136 fixed to shaft 1110. The stop ring is sized so as to prevent passage of the ring through a distal blocking element 1138 of crimp tube 1133, thereby limiting the maximum distal advancement of shaft 1110. Stop ring 1136 may comprise, for example, titanium.

Shaft 1110 typically has a diameter D1 of between about 0.2 and about 0.4 mm, e.g., about 0.3 mm. Screw threads 1114 typically define an outer diameter D2 of between about 0.6 and about 0.8 mm, e.g., about 0.7 mm, and a thread pitch P1 of between about 0.3 and about 0.6 mm, e.g., about 0.5 mm. The coil formed by wire 1120 typically has a length L1 of between about 15 and about 25 mm, e.g., about 20 mm, and an outer diameter D3 of between about 0.5 and about 0.7 mm, e.g., about 0.6 mm. Wire 1120 typically has a diameter D4 of between about 0.075 and about 0.125 mm, e.g., about 0.1 mm.

Blocking element 1138 of crimp tube 1133 typically has an inner diameter D5 of between about 0.5 and about 0.7 mm, e.g., about 0.6 mm, while stop ring 1136 has an outer diameter D6 of between about 0.65 and about 0.85 mm, e.g., about 0.75 mm. Crimp tube 1133 typically has an inner diameter D7 of between about 0.6 and about 1.0 mm, e.g., about 0.8 mm, and an outer diameter D8 which is substantially equal to an inner diameter D8 of flexible tube 1134 of lead 1106, which is between about 0.8 and about 0.12 mm, e.g., about 1 mm. Flexible tube 1134 typically has a thickness T1 of between about 0.1 and about 0.2 mm, e.g., about 0.15 mm, and an outer diameter D9 of between about 1.2 and about 1.4 mm, e.g., about 1.3 mm. Sleeve 1132 typically has an inner diameter D10 of between about 1.4 and about 1.8 mm, e.g., about 1.6 mm, and an outer diameter D11 of between about 1.8 and about 2.2, e.g., about 2 mm. Cable or wire 1131 typically has a diameter D12 of between about 0.05 and about 0.1 mm, e.g., about 0.075 mm.

During an implantation procedure performed with device 1100, screw 1108 is advanced through gastric wall 30 in a direction roughly parallel to the wall, such that the tool enters the wall at a site on an external surface thereof in abdominal cavity 20, and does not exit the gastric wall. The insertion is typically performed by rotating only shaft 1110 (e.g., clockwise), which causes the corresponding rotation of the entire electrode lead 1106. Screw 1108 is then withdrawn proximally (i.e., to the right in FIG. 30), by rotating shaft 1110 (e.g., counterclockwise). Because wire 1120 is fixed in the tissue of gastric wall, screw 1110 unscrews from wire 1120, leaving wire 1120 implanted in gastric wall 30. In addition, such rotation of shaft 1110 does not generally result in the corresponding rotation of electrode lead 1106, even if electrode lead 1106 is not actively prevented from rotating.

In an embodiment of the present invention, electrode device 1100 further comprises a rigid corkscrew 1140, which may comprise, for example, titanium. A proximal portion 1142 of corkscrew 1140 is coupled to a distal portion of crimp tube 1133, and a distal portion 1144 of the corkscrew extends around a proximal portion of the coil formed by wire 1120, without coming in contact with the coil. During the implantation procedure, a portion of corkscrew 1140 enters gastric wall 30, thereby anchoring crimp tube 1133 to the tissue of gastric wall 30, and strengthening the connection between wire 1120 and crimp tube 1133. Typically, corkscrew 1140 is shaped so as define between 1 and 3 rotations, has a length L2 of between about 1 and about 3 mm, e.g., about 2 mm, has a cross-sectional diameter D12 of between about 0.2 and about 0.3 mm, e.g., about 0.25 mm, and has a pitch P2 of between about 1 and about 3 mm, e.g., about 2 mm.

For some applications, electrode assembly 1104 comprises a cable in place of wire 1120, which generally increases the flexibility of the electrode assembly, allowing it to withstand greater deformation.

FIG. 31 is a schematic illustration of a coaxial screw-fixated electrode device 1200, in accordance with an embodiment of the present invention. Electrode device 1200 comprises an electrode assembly 1204 and an electrode lead 1206. Electrode assembly 1204 is coaxial with electrode lead 1206.

Electrode assembly 1204 comprises a distal screw 1208 coupled to a rigid or flexible shaft 1210, such as by a crimp tube 1211. Screw 1208 enables insertion and coupling of device 1200 in gastric wall 30. Thread 1209 of screw 1208 is typically wound clockwise around shaft 1210, as viewed from the proximal end of the screw. For some applications, shaft 1210 is non-conductive, and comprises, for example, nylon, polyethylene, acetal, polyamide, polyurethane, or another suitable material. For other applications, shaft 1210 is conductive, and comprises, for example, titanium, MP35N, or another suitable material. For some applications in which shaft 1210 is conductive, the shaft is coated with an insulator, such as parylene. For applications in which shaft 1210 is non-conductive (or is coated with a non-conductive coating), and, optionally, for applications in which core 1210 is conductive and non-insulated, a non-insulated wire 1220 is coiled around at least a portion of shaft 1010. Wire 1220 typically comprises platinum-iridium with a TiN coating, titanium with a TiN coating, titanium with an iridium oxide coating, platinum-iridium with an iridium oxide coating, or another suitable material, and is typically wound around shaft 1210 in a direction opposite to that of the winding of thread 1209.

Electrode assembly 1204 further comprises a screwdriver head 1222, which is coupled to a proximal end of shaft 1210. Alternatively, the proximal end of shaft 1210 is shaped so as to define screwdriver head 1222. A proximal end 1024 of screwdriver head 1022 is shaped so as to enable releasable coupling with a screwdriver, such as screwdriver 1240 described hereinbelow with reference to FIG. 32. For example, end 1224 may be square in cross-section, or may be shaped so as to define one or more notches.

Electrode assembly 1204 is coupled to electrode lead 1206 by a coupling assembly, which typically comprises a crimp tube 1230, which may comprise, for example, titanium or platinum/iridium. Shaft 1210 of electrode lead 1206 is conductive, and is typically short and rigid.

Distal screw 1208 typically has (a) an inner diameter D1 of between about 0.7 and about 1.1 mm, e.g., about 0.9 mm, (b) an outer diameter D2 of between about 1.1 and about 1.5 mm, e.g., about 1.3 mm, (c) a length L1 of between about 5 and about 6 mm, e.g., about 5.5 mm, and a thread pitch P1 of between about 0.5 and about 1.0 mm, e.g., about 0.7 mm. A proximal portion 1236 of screw 1208 that is coupled to electrode assembly 1204 typically has a length L2 of between about 1.5 and about 2.5 mm, e.g., about 2 mm. Shaft 1210 typically has a diameter D3 of between about 0.3 and about 0.5 mm, e.g., about 0.4 mm. The coil formed by wire 1220 typically has an outer diameter D4 of between about 0.52 and about 0.57 mm, e.g., about 0.545 mm, and wire 1220 typically has a diameter of between about 0.075 and about 0.125 mm, e.g., about 0.1 mm. Crimp tube 1230 typically has an outer diameter D5 of between about 0.8 and about 1 mm, e.g., about 0.9 mm, and a length L3 of between about 4 and about 6 mm, e.g., about 5 mm. Screwdriver head 1222 typically has a diameter D6 of between about 0.5 and about 0.7 mm, e.g., about 0.6 mm.

Figure 32:
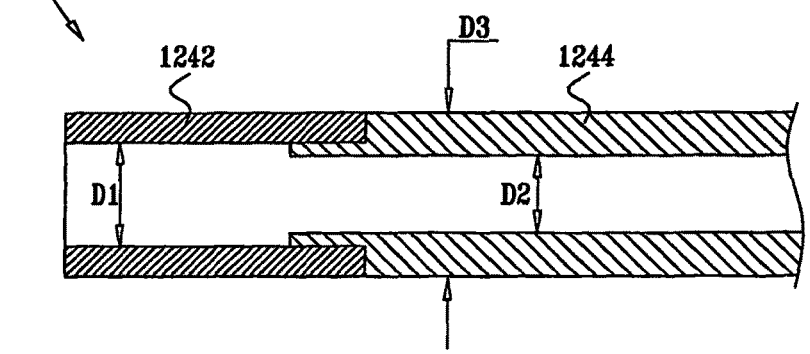
FIG. 32 is a schematic illustration of a screwdriver, in accordance with an embodiment of the present invention.

Reference is made to FIG. 32, which is a schematic illustration of a screwdriver 1240, in accordance with an embodiment of the present invention. Screwdriver 1240 comprises a coupling tube 1242, which is shaped so as to couple with proximal end 1024 of screwdriver head 1022 (FIG. 28) or another screwdriver head. Coupling tube 1242 may comprise, for example, stainless steel. Coupling tube 1242 typically has an inner diameter D1 of between about 0.8 and about 1.1 mm, e.g., about 0.95 mm. Screwdriver 1240 further comprises a flexible tube 1244, which, for some applications, is braided. The flexibility of tube 1244 generally enables the tube to remotely transmit torque regardless of orientation. Screwdriver 1240 is typically coupled to screwdriver head 1022 or 1222 (described hereinbelow) near the gastric wall. Tube 1244 typically has an inner diameter D2 of between about 0.6 and about 0.9 mm, e.g., about 0.75 mm, and an outer diameter D3 of between about 1.1 and about 1.7 mm, e.g., about 1.4 mm.

Figure 33:
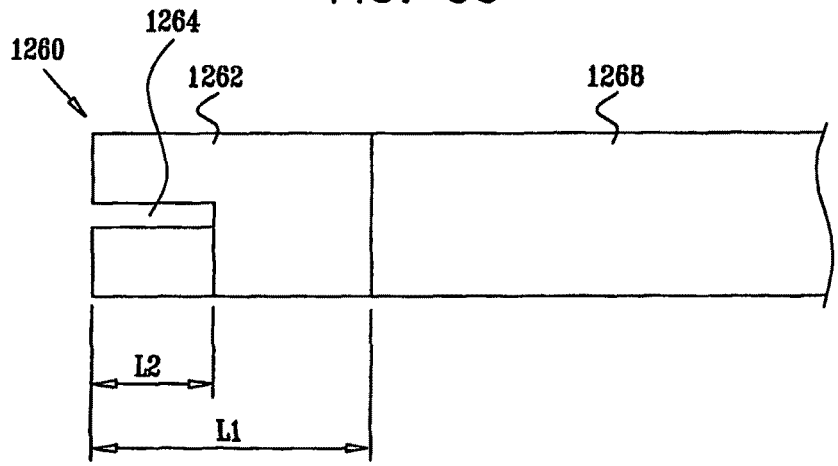
FIG. 33 is a schematic illustration of a driver, in accordance with an embodiment of the present invention.

Reference is made to FIG. 33, which is a schematic illustration of a driver 1260, in accordance with an embodiment of the present invention. Driver 1260 comprises a distal coupling element 1262 which is shaped so as to define a distal slot 1264, which is configured to engage, in a vicinity of the gastric wall, a pin 1266 defined by crimp tube 1230 (FIG. 31). Driver 1260 also comprises a proximal torque-carrying member 1268, fixed to coupling element 1262. Rotation of proximal member 1268 thus causes the rotation of electrode assembly 1204, including distal screw 1208. Coupling element 1262 typically has a length L1 of between about 4 and about 6 mm, e.g., about 5 mm, and slot 1264 typically has a length L1 of between about 1.5 and about 2.5 mm, e.g., about 2 mm. Pin 1266 of crimp tube 1230 typically has a length L4 (FIG. 31) perpendicular to the longitudinal axis of electrode device 1200 of between about 0.15 and about 0.25 mm, e.g., about 0.2 mm.

Reference is again made to FIG. 31. During an implantation procedure performed with device 1200, distal screw 1208 is advanced through gastric wall 30 in a direction roughly parallel to the wall, such that the tool enters the wall at a site on an external surface thereof in abdominal cavity 20, and does not exit the gastric wall. To advance screw 1208, screwdriver head 1222 is rotated (e.g., clockwise), such as by using screwdriver 1240 (FIG. 32), causing shaft 1210 and screw 1208 to rotate. Alternatively, crimp tube 1230 is rotated (e.g., clockwise), such as by using driver 1260 (FIG. 33), causing shaft 1210 and screw 1208 to rotate. Screwdriver 1240 or driver 1260 is withdrawn, leaving electrode assembly 1204, including screw 1208, implanted in gastric wall 30, and the remainder of electrode device 1200, including electrode lead 1206, implanted in the body of the subject. Lead 1206 is coupled to an implanted or external control unit.

In an embodiment of the present invention, electrode device 1200 further comprises a rigid corkscrew 1280, which may comprise, for example, titanium. A proximal portion 1282 of corkscrew 1280 is coupled to a distal portion of crimp tube 1230, and a distal portion 1284 of the corkscrew extends around a proximal portion of the coil formed by wire 1220, without coming in contact with the coil. During the implantation procedure, a portion of corkscrew 1280 enters gastric wall 30, thereby anchoring crimp tube 1230 to the tissue of gastric wall 30, and strengthening the connection between wire 1220 and crimp tube 1230. Typically, corkscrew 1280 is shaped so as define between 2 and 3 rotations, has a length L5 of between about 1 and about 3 mm, e.g., about 2 mm, has a cross-sectional diameter of between about 0.2 and about 0.3 mm, e.g., about 0.25 mm, and has a pitch P2 of between about 1 and about 3 mm, e.g., about 2 mm.

For some applications, electrode assembly 1204 comprises a cable in place of wire 1220, which generally increases the flexibility of the electrode assembly, allowing it to withstand greater deformation.

Reference is now made to FIGS. 34-36, which are schematic illustrations of a T-anchor electrode device 1300, in accordance with an embodiment of the present invention. As shown in FIGS. 34 and 36, electrode device 1300 comprises an electrode assembly 1304 and an electrode lead 1306. As shown in FIG. 35, electrode device 1300 additionally comprises an implantation tool 1302. Tool 1302, electrode assembly 1304, and electrode lead 1306 are generally coaxial with one another.

Electrode assembly 1304 comprises a core 1310, which typically is non-conductive and flexible. Core 1310 typically comprises a non-conductive suture, which may comprise, for example, nylon, polyethylene, polyester, or another suitable material. Alternatively, core 1310 is conductive and not insulated, and typically comprises a cable, which may comprise titanium. For applications in which core 1310 is non-conductive, and, optionally, for applications in which core 1310 is conductive, a non-insulated wire 1311 is coiled around at least a portion of core 1310. Wire 1311 typically comprises platinum-iridium with a TiN coating, titanium with a TiN coating, titanium with an iridium oxide coating, platinum-iridium with an iridium oxide coating, or another suitable material. At a distal end thereof, the electrode assembly comprises a coupling element 1312, which typically comprises a T-anchor 1314. T-anchor 1314 is generally similar to T-anchors commonly used for attaching tags to apparel, and may comprise, for example, nylon or polyethylene. For some applications, T-anchor 1314 and core 1310 are fabricated as an integrated unit.

Core 1310 may be conductive or non-conductive, and typically has a diameter of between about 0.3 and about 0.5 mm, e.g., about 0.4 mm. The coil formed by wire 1311 typically has an outer diameter D2 of between about 0.4 and about 0.6 mm, e.g., about 0.5 mm, and wire 1311 typically has a diameter D3 of between about 0.75 and about 1.25 mm, e.g., about 1 mm.

Lead 1306 comprises an elongated conductor 1330, which is typically coiled around core 1310 (the same core as that of electrode assembly 1304). The coil formed by conductor 1330 typically has an outer diameter D4 of between about 0.7 and about 1.0 mm, e.g., about 0.9 mm, and conductor 1330 typically has a diameter D5 of between about 0.6 and about 0.9 mm, e.g., about 0.75 mm. Lead 1306 typically further comprises a proximal crimp tube 1331, which couples a proximal portion of conductor 1330 to core 1310.

Wire 1311 of electrode assembly 1304 and conductor 1330 are typically coupled together in a vicinity of the distal end of lead 1306 by a crimp tube 1333, which typically has an outer diameter D6 of between about 0.7 and about 1.1 mm, e.g., about 0.9 mm. A non-conductive sleeve or coating 1332, which comprises, for example, silicone, surrounds lead 1306, crimp tube 1333, and a proximal portion of electrode assembly 1304. The portion of sleeve 1332 that surrounds crimp tube 1333 typically has an outer diameter D7 of between about 1.2 and about 1.6 mm, e.g., about 1.4 mm.

Reference is again made to FIG. 35. Implantation tool 1302 comprises a rod 1344, which comprises, for example, stainless steel. Rod 1344 is shaped so as to define a sharp distal tip 1345. For some applications, at least a portion of rod 1344 is slightly curved. For example, a distal portion of the rod may be slightly curved.

Reference is made to FIG. 37, which is a schematic cross-sectional illustration of rod 1344, in accordance with an embodiment of the present invention. In cross section, rod 1344 is shaped so as to define less than a complete 360-degree circle. In other words, rod 1344 is not shaped so as to define a bore. Typically, the cross section of rod 1344 defines an arc having an angle of between about 260 and about 300 degrees, e.g., about 280 degrees. The resulting lateral opening 1360 in rod 1344 allows electrode assembly 1304 and lead 1306 to be laterally inserted and removed from rod 1344.

Reference is again made to FIG. 35. Prior to an implantation procedure performed with device 1300, electrode assembly 1304 and lead 1306 are held within rod 1344 of implantation tool 702. Rod 1344 is advanced through gastric wall 30 in a direction roughly parallel to the wall, such that rod 1344 enters the wall at a first site on an external surface thereof in abdominal cavity 20, and exits at a second site on the external surface. Rod 1344 generally does not enter the lumen of stomach 10. Rod 1344 is advanced through gastric wall 30 until coupling element 1312 exits the gastric wall at the second site thereon. At this point during the procedure, electrode assembly 1304 is within gastric wall 30, and also within rod 1344.

Rod 1344 is then withdrawn proximally (i.e., to the right in FIG. 35). As rod 1344 is withdrawn, coupling element 1312 prevents electrode assembly 1304 from being withdrawn with the rod. In FIG. 36, electrode assembly 1304 is shown implanted in gastric wall 30 after the rod has been fully withdrawn.

For some applications, one or more features of electrode device 1300 are combined with one or more features of other electrode devices described herein, mutatis mutandis. For example, electrode assembly 1304 and lead 1306 may be used with implantation tool 702, described hereinabove with reference to FIG. 24, mutatis mutandis, such that lead 1306 and a portion of electrode assembly 1304 are not coaxial with tool 702. Alternatively, one of the branches of T-anchor 1314 is coupled to loop 1534 described hereinbelow with reference to FIG. 39, such that the T-anchor generally serves the function otherwise served by tines 1536.

FIG. 38 is a schematic illustration of a stylet-guided corkscrew electrode device 1400, in accordance with an embodiment of the present invention. Electrode device 1400 comprises a stylet 1410 and a corkscrew-shaped electrode 1412 coiled around a portion of the stylet. Both the corkscrew electrode and the stylet may be, but are not necessarily generally flexible but stiff. The stylet is typically straight, and shaped so as to define a sharp or dull distal tip 1414. Electrode device 1400 further comprises an electrode lead 1420, which is coupled to corkscrew electrode 1412, as described hereinbelow. Stylet 1410 is able to slide with respect to the corkscrew electrode and the electrode lead.

Electrode lead 1420 typically comprises a wire coil 1422, surrounded by a non-conductive sleeve or coating 1424, which comprises, for example, silicone. A distal portion of wire coil 1422 is coupled to a proximal end of corkscrew electrode 1412, typically by welding both the wire coil and the corkscrew electrode to an outside surface of a weld tube 1426. Stylet 1410 is able to slide through weld tube 1426.

Stylet 1410 typically has a diameter D1 of between about 0.3 and about 1.0 mm, e.g., about 0.9 mm. The coil formed by electrode 1412 typically has an outer diameter D2 of between about 1.5 and about 2.8 mm, e.g., about 2.2 mm, an inner diameter D3 of between about 1.1 and about 2.1 mm, e.g., about 1.6 mm, and a pitch P1 of between about 0.5 and about 1.5 mm, e.g., about 1.0 mm. A ratio of coil inner diameter D3 to diameter D1 of stylet 1410 is typically between about 1.5 and about 3.0. Electrode 1412 typically has a diameter D4 of between about 0.2 and about 0.4 mm, e.g., about 0.3 mm.

For some applications, stylet 1410 comprises an inner wire and an outer wire tightly wrapped around the inner wire. The inner wire typically has a diameter of between about 0.1 and about 0.3 mm, and the outer wire typically has a diameter of between about 0.7 and about 0.9 mm. Such a configuration generally provides the stylet with flexibility.

During an implantation procedure, stylet 1410 is advanced distally through corkscrew electrode 1412 until a portion of the stylet protrudes from the distal end of the corkscrew electrode. The stylet is then placed in contact with a surface of gastric wall 30 (e.g., an outer surface thereof) at a first site of the wall, with the outer side of corkscrew electrode 1412 touching the gastric wall. Corkscrew electrode 1412 is rotated, so that a distal tip 1428 of the corkscrew electrode repeatedly enters and leaves gastric wall 30. The electrode is thereby advanced along the gastric wall, such that a portion 1430 of each coil of the corkscrew electrode remains in the gastric wall, while the remainder 1432 of each coil protrudes from the wall. Stylet 1410 prevents corkscrew electrode 1412 from penetrating beyond a certain depth into gastric wall 30. After the corkscrew electrode has been implanted along a desired length of the gastric wall, the stylet is withdrawn from corkscrew electrode 1412 and electrode lead 1420 by sliding the stylet in a proximal direction. The corkscrew electrode remains implanted in the gastric wall.

In an embodiment of the present invention, a suturing device comprises a stylet and corkscrew. The stylet is placed along tissue requiring suturing, and the corkscrew is advanced along and rotated around the stylet, as described hereinabove regarding corkscrew electrode 1412 of FIG. 38, such that the corkscrew sutures the tissue. The stylet is then removed. In this case, the tissue may be skin of a patient, or an internal tissue, e.g., tissue of an organ to be sutured during a minimally-invasive procedure.

Figure 39:
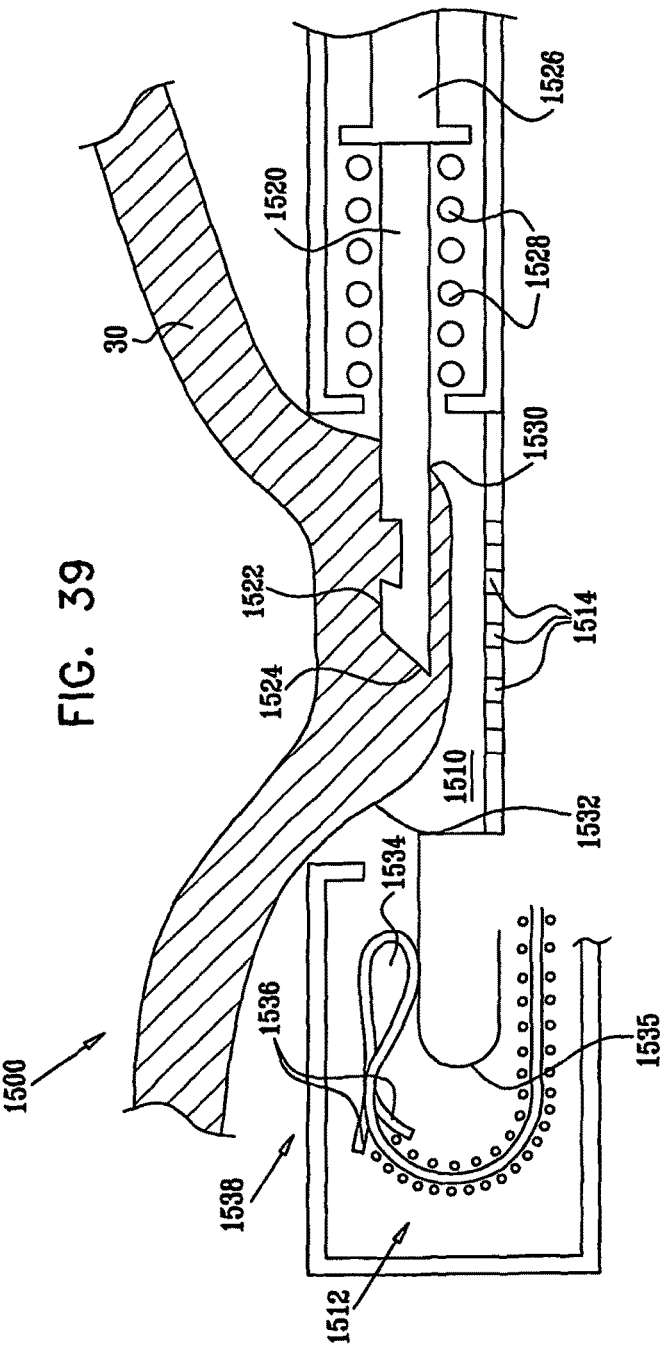
FIG. 39 is a schematic illustration of a hook-assisted electrode implantation cartridge, in accordance with an embodiment of the present invention.

Reference is made to FIG. 39, which is a schematic illustration of a hook-assisted electrode implantation cartridge 1500, in accordance with an embodiment of the present invention. Cartridge 1500 operates on principles similar to those of cartridge 458, described hereinabove with reference to FIGS. 17-19. Cartridge 1500 is shaped so as to define at least one lateral chamber 1510, which receives and positions a portion of gastric wall 30 for properly aligned insertion of an electrode assembly 1512. Typically, chamber 1500 comprises one or more vacuum ports 1514, which draw and hold the gastric wall in the chamber during insertion of electrode assembly 1512.

Cartridge 1500 comprises a hooking element 1520, which is shaped so as to define a hook 1522 and a sharp distal tip 1524. A shaft 1526 controls the longitudinal movement of hooking element 1520. Cartridge 1500 typically comprises a spring 1528, which is configured to either aid with the insertion of hooking element 1520 into gastric wall 30, or its subsequent withdrawal therefrom.

During an implantation procedure, gastric wall 30 is positioned within chamber 1510. Hooking element 1520 is advanced distally from cartridge 1500 into chamber 1510, such that the hooking element enters the gastric wall at a first site 1530 on an external surface thereof, and exits at a second site 1532 on the external surface. Hooking element 1520 then reenters cartridge 1500, and hook 1522 engages a loop 1534 of electrode assembly 1512. The hooking element is withdrawn proximally (i.e., to the right in FIG. 39), pulling electrode assembly 1512 through gastric wall 30. For some applications, the hooking element is subsequently distally advanced slightly (i.e., to the left in the figure) and rotated, in order to disengage hook 1522 from loop 1534.

For some applications, within cartridge 1500 electrode assembly 1512 is drawn in a curved path around a guiding element 1535 of cartridge 1500, which may comprise Teflon, for example. Guiding element 1535 may be disposed within the endoscope (as shown), or, alternatively, guiding element 1535 may constitute the distal end of the endoscope, whereby electrode assembly 1512 exits the endoscope, curves backwards, and reenters the endoscope (at least in part, e.g., by entering an exterior open channel of the endoscope), in order to be engaged by hooking element 1520. For some applications, in order to facilitate this behavior, electrode assembly 1512 has a shape memory which induces the curving backwards towards the hooking element. In the configuration shown in FIG. 39, tines 1536 of a coupling element 1538 exit gastric wall in a vicinity of first site 1530, and engage the wall, thereby holding the electrode assembly in place within the gastric wall. Alternatively, coupling element 1538 uses other techniques, such as a T-anchor, as described hereinabove with reference to FIGS. 34-36.

In an embodiment of the present invention, a corkscrew electrode is implanted in gastric wall 30 by aligning the corkscrew electrode generally perpendicular with the wall and rotating the corkscrew electrode so that it enters the wall.

Reference is made to Tables 1-3 below, which show pull force experimental results measured in accordance with respective embodiments of the present invention. Table 1 shows the pull forces necessary to dislodge a 1.3 mm diameter screw having approximately 5 turns from fresh chicken breast, as measured during three tests.

TABLE 1

| Test # | Pull force [newtons] |
| --- | --- |
| 1 | 0.55 |
| 2 | 0.45 |
| 3 | 0.5 |

Table 2 shows the pull forces necessary to dislodge a 1.3 mm diameter screw having approximately 5 turns from fresh chicken breast/connective tissue, as measured during three tests.

TABLE 2

| Test # | Pull force [newtons] |
|---|---|
| 1 | 0.9 |
| 2 | 0.65 |
| 3 | 0.85 |

Table 3 shows the results of an experiment performed using a wire having a set of four silicone tines at the distal end thereof. The wire was inserted in a distal direction into one side of a piece of fresh chicken, until the tines and a portion of the wire protruded from the opposite side of the piece of chicken. As the wire was subsequently retracted in a proximal direction, pull forces were measured (a) as the wire slid through the chicken before the tines lodged against the surface of the chicken, and (b) as the tines were pulled through the chicken and dislodged therefrom. The table shows the forces measured during two tests.

TABLE 3

| Test # | Pull force to slide [newtons] | Pull force to dislodge [newtons] |
|---|---|---|
| 1 | 0.1 | 0.2 |
| 2 | 0.05 | 0.15 |

By way of comparison, the pull force measured to dislodge a 6.4 cm coarse dry wall screw from 2.0 lb density polyester foam was 20 newtons, and the pull force measured to dislodge a 1.5 mm diameter, 2 mm length corkscrew electrode from cardiac tissue was 136 grams.

Figure 40:
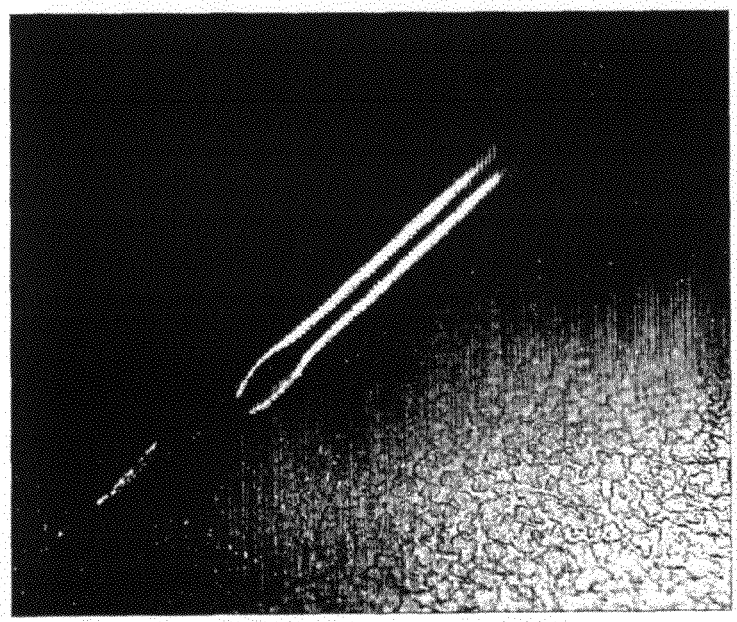
FIGS. 40-43D are photographs of mockups of several of the electrode devices of the present invention, in accordance with respective embodiments of the present invention.

FIG. 40 is a photograph of a mockup of distal portion 709 of electrode assembly 704 and distal portion 752 of tool 702, as described hereinabove with reference to FIGS. 24 and 25, in accordance with an embodiment of the present invention.

Figure 41A:
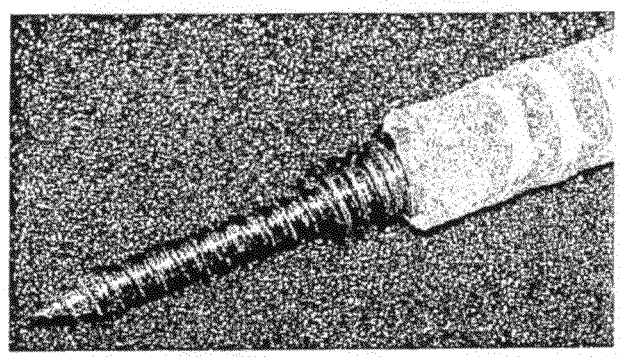
Figure 41B:
Figure 41C:
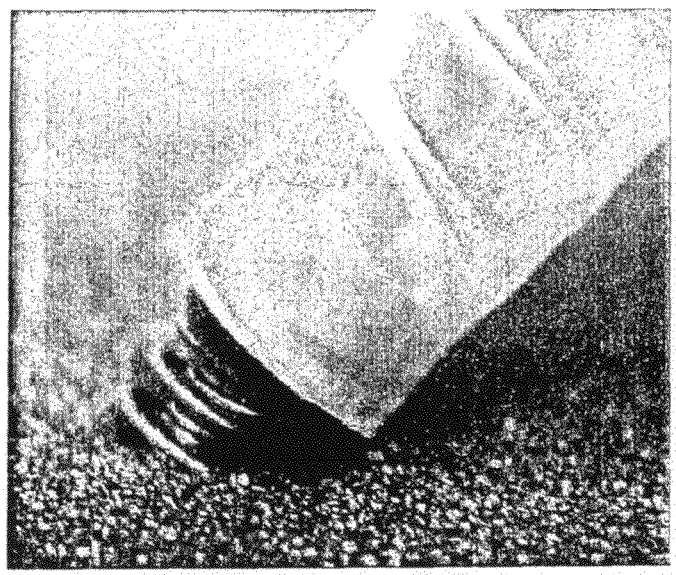
Figure 41D:
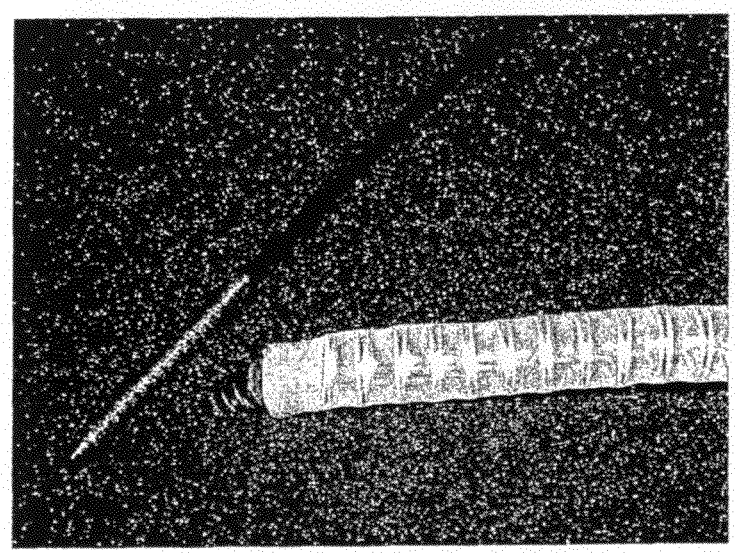

FIGS. 41A-D are photographs of a mockup of coaxial screw-driven electrode device 1100, as described hereinabove with reference to FIG. 30, in accordance with an embodiment of the present invention. In the embodiment shown in FIGS. 41A-D, electrode device 1100 comprises corkscrew 1140, as described hereinabove with reference to FIG. 30. FIG. 41A shows the electrode device prior to implantation. FIG. 41B shows the electrode device after a portion of electrode assembly 1104 has entered simulated tissue (modeled by sponge). FIG. 41C shows the electrode device after corkscrew 1140 has been coupled to the simulated tissue. FIG. 41D shows the electrode device after the completion of the implantation procedure, and the removal of implantation tool 1102.

Figure 42:
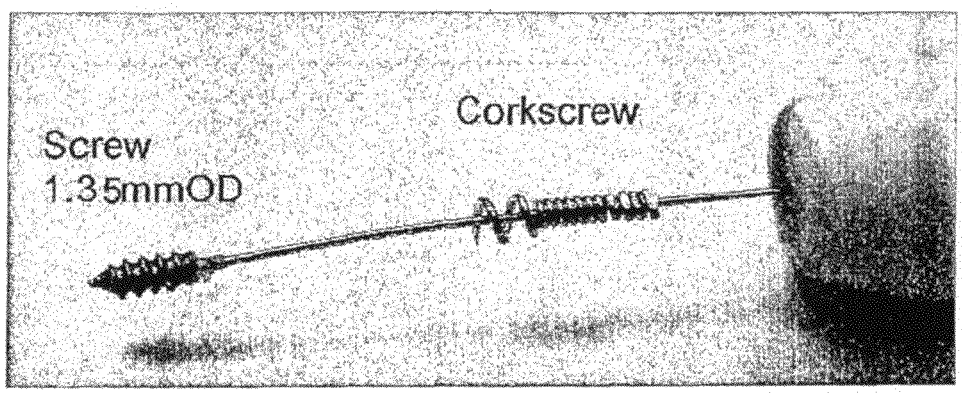

FIG. 42 is a photograph of a mockup of coaxial screw-fixated electrode device 1200, as described hereinabove with reference to FIG. 31, in accordance with an embodiment of the present invention. In the embodiment shown in FIG. 42, electrode device 1200 comprises corkscrew 1280, as described hereinabove with reference to FIG. 31.

Figure 43A:
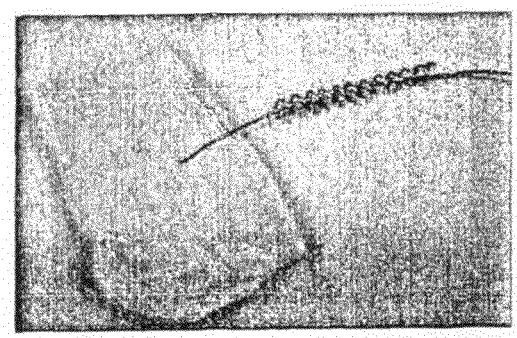
Figure 43B:
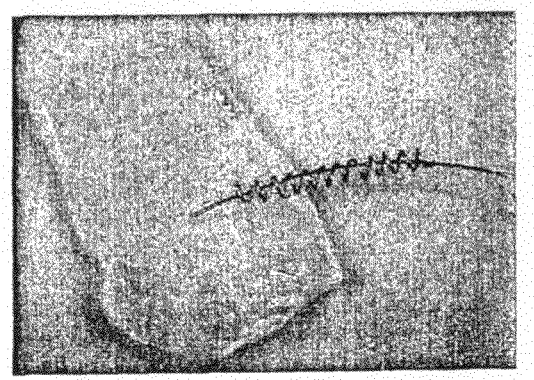
Figure 43C:
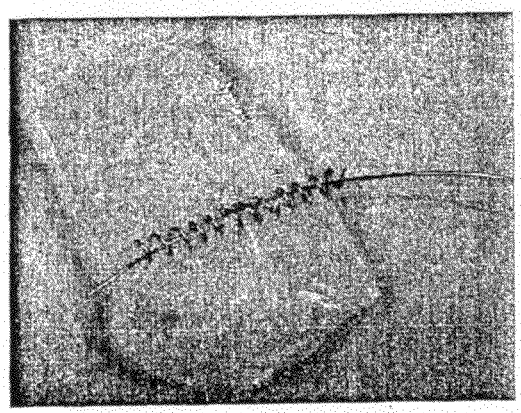
Figure 43D:
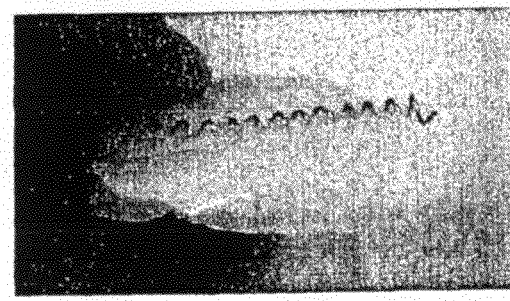

FIGS. 43A-D are photographs of a mockup of stylet-guided corkscrew electrode device 1400, as described hereinabove with reference to FIG. 38, in accordance with an embodiment of the present invention. In FIGS. 43A-D, only stylet 1410 and corkscrew-shaped electrode 1412 are shown. Two percent agarose was used to simulate gastric tissue. FIG. 43A shows the electrode device after stylet 1410 has been placed against the simulated tissue. FIG. 43B shows the electrode device after corkscrew electrode 1412 has been partially implanted in the simulated tissue. FIG. 43C shows the electrode device after the corkscrew electrode has been fully implanted, but prior to withdrawal of the stylet. FIG. 43D shows the corkscrew electrode fully implanted after withdrawal of the stylet.

Electrode devices described hereinabove are typically implanted using one of the following implantation approaches:
- the combined endoscopic and transabdominal approach described hereinabove with reference to FIGS. 1-14;
- the endoluminal transgastric approach described hereinabove with reference to FIGS. 15A-19;
- an endoscopic approach via stomach 10;
- a laparoscopic trans-abdominal approach using a trocar;
- invagination, whereby the electrode is placed on the surface of the gastric wall, tissue of the gastric wall is wrapped around the electrode, and the invagination is sutured closed; or
- a surgical approach in which a shallow incision is made in the gastric wall, the electrode is placed through the incision, and the incision is closed.

In an embodiment of the present invention, one or more of the following techniques is used to reduce tissue resistance to the insertion of the electrode devices described herein:
- the electrode device is at least partially coated with a low friction material such as Teflon or Parylene;
- the electrode device is inserted quickly in order to pass through the serosal and other connective tissue layers, e.g., using a rapid advancement mechanism (such as a pre-loaded spring), instead of or in addition to physician-mediated insertion of the electrode device;
- vibration is applied to implantation tools;
- ultrasound is applied to the tissue, in order to weaken the tissue, thereby reducing the counter force applied by the tissue;
- pulsed diathermia is applied to the tissue; and/or
- a pulsed jet of water or saline solution is applied to the tissue.

It is noted that although some embodiments of the present invention are described hereinabove with respect to implanting gastric electrodes using a per-oral approach, the scope of the present invention includes implanting electrodes on the small intestine, using a per-oral approach, or implanting electrodes on the colon or small intestine using a per-rectum approach. The scope of the present invention additionally includes implanting electrodes using a transvascular approach, e.g., to implant electrodes in the heart. Alternatively or additionally, it is noted that the scope of the present invention includes implanting other apparatus (e.g., a biosensor, such as a glucose sensor or a pressure sensor), in addition to or instead of electrodes.

The scope of the present invention includes embodiments described in PCT Patent Publication WO 2006/129321 to Policker et al., which:

(a) claims priority from U.S. 60/687,099, filed Jun. 2, 2005, and (b) is a continuation-in-part of PCT Patent Application PCT/US2006/010911, filed Mar. 24, 2006, which claims priority from U.S. 60/665,320, filed Mar. 24, 2005.

The '321, '099, '911, and '320 patent applications are assigned to the assignee of the present patent application and are incorporated herein by reference. For some applications, techniques described herein are carried out in combination with methods and apparatus described in one or more of these patent applications. Such methods and apparatus may include, for example, some or all of the following six methods and apparatus:

1. An implantation system, comprising:
  an electrode, configured for implantation at a gastric implantation site of a patient; and
  an endoscope configured to provide access to the gastric implantation site, to stabilize itself and the site with respect to each other by using suction, and to facilitate insertion of the electrode into the gastric implantation site.
  In an embodiment, the electrode is disposed within the endoscope prior to being inserted into the gastric implantation site.
  In an embodiment, a distal tip of the endoscope is configured to be within the stomach, adjacent to the implantation site, when the electrode is inserted into the implantation site.
2. A method, comprising:
  passing into a stomach of a patient an endoscope having electrode apparatus, the electrode apparatus including at least one electrode;
  pushing the electrode apparatus through a wall of the stomach to a site outside of the stomach;
  moving the electrode apparatus while it is outside of the stomach in a manner that places the electrode in contact with the stomach wall; and
  leaving the electrode in the stomach wall.
  In an embodiment, the stomach wall includes a muscular layer, and leaving the electrode comprises leaving the electrode in the muscular layer.
  In an embodiment, the stomach wall includes a submucosal layer, and leaving the electrode comprises leaving the electrode in the submucosal layer.
3. A method, comprising:
  passing electrode apparatus into a stomach of a patient, the electrode apparatus including at least one electrode;
  pushing the electrode apparatus through a wall of the stomach to a site outside of the stomach;
  moving the electrode apparatus while it is outside of the stomach in a manner that places the electrode in contact with the stomach wall; and
  leaving the electrode in the stomach wall.
  In an embodiment, the stomach wall includes a muscular layer, and leaving the electrode comprises leaving the electrode in the muscular layer.
  In an embodiment, the stomach wall includes a submucosal layer, and leaving the electrode comprises leaving the electrode in the submucosal layer.
  In an embodiment, passing the electrode apparatus comprises passing an endoscope to which the electrode apparatus is coupled.
  In an embodiment, the electrode apparatus includes at least one needle electrode, and leaving the electrode comprises leaving the needle electrode in the stomach wall.
4. A method for implanting gastric leads, comprising:
  applying positive gas pressure through one lumen of an endoscope;
  applying negative gas pressure through another lumen of the endoscope; and
  implanting the leads using the endoscope.
5. An implantation system, comprising:
  transluminal apparatus configured to provide access to a gastric implantation site of a patient and to apply pressure to the gastric implantation site;
  an electrode, configured for implantation at the implantation site; and
  abdominal cavity apparatus configured to be positioned within an abdomen of the patient, outside of the stomach,
  wherein the system is configured such that application of the pressure by the transluminal apparatus facilitates insertion of the electrode into the wall by the abdominal cavity apparatus.
  In an embodiment, the transluminal apparatus is configured to apply the pressure in a manner that brings the site adjacent to an abdominal wall of the patient.
  In an embodiment, the transluminal apparatus comprises at least one endoscope.
  In an embodiment, prior to the insertion of the electrode, the transluminal apparatus and the abdominal cavity apparatus are independently manipulatable.
  In an embodiment, the transluminal apparatus is configured to apply suction to the gastric implantation site.
  In an embodiment, the electrode comprises a needle electrode.
  In an embodiment, the abdominal cavity apparatus is configured to be passed through an abdominal wall of the patient, towards the stomach.
  In an embodiment, a distal tip of the transluminal apparatus is configured to be within the stomach, adjacent to the implantation site, when the abdominal cavity apparatus inserts the electrode into the wall.
  In an embodiment, the transluminal apparatus is configured to apply the pressure by inflating the stomach.
  In an embodiment, a physical portion of the transluminal apparatus is configured to apply the pressure to the gastric implantation site.
  In an embodiment, the physical portion of the transluminal apparatus comprises a tip of the transluminal apparatus.
  In an embodiment, the abdominal cavity apparatus is configured to be coupled to the transluminal apparatus at least during the insertion of the electrode.
  In an embodiment, the abdominal cavity apparatus is in contact with the transluminal apparatus at least during the insertion of the electrode.
6. A method, comprising:
  physically contacting a gastric implantation site of a stomach via a transluminal approach;
  physically contacting the site via a transabdominal approach; stabilizing the site; and
  implanting an electrode at the site based on the physical contact provided by the transluminal and transabdominal approach.
  In an embodiment, stabilizing the site comprises inflating the stomach, applying pressure to the stomach, and/or applying suction.

The scope of the present invention includes embodiments described in PCT Patent Publication WO 06/102626 to Policker et al., which claims priority from U.S. 60/665,320, filed Mar. 24, 2005. The '626 and '320 applications are assigned to the assignee of the present patent application and are incorporated herein by reference. For some applications, techniques described herein are carried out in combination with methods and apparatus described in one or both of these patent applications. Such methods and apparatus may include, for example, some or all of the following:
1. Apparatus, comprising:
  an endoscope; and
  a plurality of electrode cartridges within the endoscope, each cartridge comprising at least one electrode for implantation in a patient.
2. Apparatus, comprising:
  an endoscope; and
  an insertion head coupled to the endoscope and comprising an electrode, the insertion head being adapted to be pushed through a wall of a stomach to a site outside of the stomach and to be subsequently moved by the endoscope in a manner that places the electrode in contact with a muscular layer of the stomach.

In an embodiment, the insertion head is adapted to be rotated by the endoscope to place the electrode in contact with the muscular layer.

In an embodiment, the insertion head is adapted to be pulled by the endoscope to place the electrode in contact with the muscular layer.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. In particular, the scope of the present invention includes combinations of the various features of electrode devices described hereinabove, and combinations of the various electrode devices with the various surgical implantation techniques described hereinabove. Additionally, the scope of the present invention includes performing in the abdominal cavity activities described as being performed in the stomach, and performing in the stomach activities described as being performed in the abdominal cavity.

The invention claimed is:

1. Apparatus comprising:
an electrode;
a lead, coupled to the electrode; and
an implantation tool, which comprises:
    a securing device, which is configured to secure the implantation tool to a portion of a gastric wall of a patient; and
    an element which is configured to puncture and move distally through the portion of the gastric wall, and subsequently draw the electrode proximally through the portion of the gastric wall to insert the electrode into the gastric wall generally in parallel to the gastric wall,
wherein the implantation tool is configured to be removed from a body of the patient after implanting the electrode, such that only the electrode and the lead remain in the body.

2. The apparatus according to claim 1, wherein the implantation tool is configured to insert a length of the electrode that is at least 1 cm into the gastric wall, generally in parallel to the gastric wall.

3. The apparatus according to claim 1, wherein the securing device comprises a suction applicator.

4. The apparatus according to claim 1, wherein the securing device comprises first and second articulating pieces, the first piece configured to engage an inner surface of the gastric wall, and the second piece configured to engage an outer surface of the gastric wall.

5. Apparatus, comprising:
an electrode;
a lead, coupled to the electrode; and,
an implantation tool, which comprises a longitudinal element shaped to define a sharp distal tip that is configured to puncture a gastric wall of a patient,
wherein a distal portion of the electrode is parallel to a distal portion of the longitudinal element,
wherein the electrode is coupled to the implantation tool such that distal advancement of the implantation tool in the gastric wall advances the electrode in the gastric wall generally in parallel to the gastric wall,
wherein the implantation tool is configured to permit decoupling of the electrode from the longitudinal element defining the sharp tip following implantation of the electrode in the gastric wall, and
wherein the implantation tool is configured to be removed from a body of the patient after implanting the electrode, such that only the electrode and the lead remain in the body.

6. The apparatus according to claim 5, wherein the longitudinal element comprises a rod.

7. The apparatus according to claim 5, wherein a proximal portion of the longitudinal element is shaped to define a bore, and wherein a distal portion of the longitudinal element, proximal to the sharp distal tip, is not shaped to define a bore.

8. The apparatus according to claim 5, wherein a distal portion of the longitudinal element, proximal to the sharp distal tip, is shaped to define, an arc when viewed in axial cross-section.

9. The apparatus according to claim 8, wherein the distal portion of the electrode is disposed within the arc defined by the distal portion of the longitudinal element.

10. The apparatus according to claim 9, wherein the implantation tool comprises a pushing element, configured to decouple the electrode from the longitudinal element by applying a pushing force to the electrode during proximal motion of the longitudinal element.

11. The apparatus according to claim 9, wherein the implantation tool comprises one or more coupling rings, coupled to the distal portion of the longitudinal element, and wherein the distal portion of the electrode is slidably coupled within the one or more coupling rings.

12. The apparatus according to claim 11, wherein the one or more coupling, rings inhibit decoupling of the distal portion of the longitudinal element from the distal portion of the electrode due to relative lateral motion of the longitudinal element with respect to the electrode, but permit decoupling of the distal portion of the longitudinal element from the distal portion of the electrode due to relative axial motion of the longitudinal element with respect to the electrode.

13. The apparatus according to claim 5, wherein the implantation tool is configured to decouple the electrode from the longitudinal element defining the sharp tip by proximal withdrawal of the implantation tool.

14. Apparatus, comprising:
two electrodes; and
an implantation tool, which (a) is configured to implant the electrodes in a gastric wall of a patient, without removing the implantation tool from a body of the patient between successive electrode implantations, and (b) comprises a cartridge, within which are removably disposed the two electrodes,
wherein the cartridge is generally cylindrical in shape, and is configured (a) to implant a first one of the electrodes, (b) subsequently to be rotated, and (c) subsequently to implant a second one of the electrodes.

15. The apparatus according to claim 14, wherein the two electrodes are separated by 150-180 degrees with respect to an axis of the cartridge.

16. The apparatus according to claim 14, wherein the cartridge is configured to be secured to a site of implantation of the first electrode to facilitate the implantation of the first electrode and during rotation of the cartridge, and to subsequently be secured to a site of implantation of the second electrode to facilitate the implantation of the second electrode.

17. The apparatus according to claim 16, comprising a source of suction, to secure the cartridge to the site of implantation of the first electrode.

18. The apparatus according to claim 16, comprising a securing device, configured to secure the cartridge, to the gastric wall by squeezing an inner surface and an outer surface of the gastric wall at the site of implantation of the first electrode.

19. The apparatus according to claim 14, wherein the cartridge, by being rotated following the implantation of the first electrode, is configured to facilitate implantation of the second electrode at a distance from the first electrode that is equal to a circumferential distance between the first and second electrodes while the first and second electrodes are disposed within the cartridge.

20. The apparatus according to claim 14, wherein the cartridge is configured to implant the electrodes in the gastric wall generally in parallel to the gastric wall.

21. The apparatus according to claim 14, further comprising two leads, which are coupled to the two electrodes, respectively, wherein the implantation tool is configured to be removed from a body of the patient after implanting the two electrodes, such that only the two electrodes and the two feuds remain in the body.

22. The apparatus according to claim 14, wherein the cartridge is shaped so as to define two lateral chambers, within which are removably disposed the two electrodes, respectively.

23. A method comprising:
providing an electrode and a lead coupled to the electrode;
using a securing device of an implantation tool, securing the implantation tool to a portion of a gastric wall of a patient;
puncturing and moving distally an element of the implantation tool through the portion of the gastric wall, and subsequently using the element to draw the electrode proximally through the portion of the gastric wall, thereby inserting the electrode into the gastric wall generally in parallel to the gastric wall; and
removing the implantation tool from a body of the patient after implanting the electrode, such that only the electrode and the lead remain in the body.

24. A method comprising:
providing an electrode and a lead coupled to the electrode;
providing an implantation tool, which includes a longitudinal element shaped to define a, sharp distal tip that is configured to puncture a gastric wall of a patient, wherein a distal portion of the electrode is parallel to a distal portion of the longitudinal element;
distally advancing the implantation tool in the gastric wall so as to advance the electrode in the gastric wall generally in parallel to the gastric wall;
decoupling the electrode from the longitudinal element defining the sharp tip following implantation of the electrode in the gastric wall; and
removing the implantation tool from a body of the patient after implanting the electrode, such that only the electrode and the lead remain in the body.

25. The method according to claim 24, wherein decoupling comprises decoupling the electrode from the longitudinal element defining the sharp tip by proximally withdrawing the implantation tool.

26. A method comprising:
providing two electrodes;
providing an implantation tool, which (a) Is configured to implant the electrodes in a gastric wall of a patient, without removing the implantation tool from a body of the patient between successive electrode implantations, and (b) includes a generally cylindrically-shaped cartridge: within which are removably disposed the two electrodes;
implanting a first one of the electrodes using the cartridge;
thereafter, rotating the cartridge; and
thereafter, implant a second one of the electrodes using the cartridge.

27. The method according, to claim 26, wherein implanting the first and the second electrodes comprises implanting the first and the second electrodes in the gastric wall generally in parallel, to the gastric wall, using the cartridge.

28. The method according to claim 26, further comprising:
providing two leads, which are coupled to the two electrodes, respectively; and
removing the implantation tool from a body of the patient after implanting the two electrodes, such that only the two electrodes and the two leads remain in the body.

* * * * *

UNITED STATES PATENT AND TRADEMARK OFFICE
CERTIFICATE OF CORRECTION

| | |
|---|---|
| PATENT NO. | : 8,463,404 B2 |
| APPLICATION NO. | : 12/160616 |
| DATED | : June 11, 2013 |
| INVENTOR(S) | : Tamir Levi et al. |

Page 1 of 1

It is certified that error appears in the above-identified patent and that said Letters Patent is hereby corrected as shown below:

In the Claims:

Column 45, line 58, Claim 5, line 3, "and," should read -- and --.
Column 46, line 17, Claim 8, line 3, "define," should read -- define --.
Column 46, line 20, Claim 9, line 2, "are" should read -- arc --.
Column 46, line 33, Claim 12, line 2, "coupling," should read -- coupling --.
Column 47, line 5, Claim 18, line 2, "cartridge," should read -- cartridge --.
Column 47, line 24, Claim 21, line 5, "feuds" should read -- leads --.
Column 48, line 4, Claim 24, line 4, "a," should read -- a --.
Column 48, line 22, Claim 26, line 3, "Is" should read -- is --.
Column 48, line 27, Claim 26, line 8, "tridge:" should read -- tridge, --.
Column 48, line 35, Claim 27, line 4, "parallel," should read -- parallel --.

Signed and Sealed this
Third Day of September, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,463,404 B2
APPLICATION NO. : 12/160616
DATED : June 11, 2013
INVENTOR(S) : Levi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1340 days.

Signed and Sealed this
Eighth Day of September, 2015

Michelle K. Lee
*Director of the United States Patent and Trademark Office*